(12) United States Patent
Salamini et al.

(10) Patent No.: US 11,707,206 B2
(45) Date of Patent: Jul. 25, 2023

(54) DEVICES AND METHODS FOR VASCULAR NAVIGATION, ASSESSMENT AND/OR DIAGNOSIS

(71) Applicant: Piccolo Medical, Inc., San Francisco, CA (US)

(72) Inventors: Alexey Salamini, San Francisco, CA (US); Jonathan Silberstein, San Francisco, CA (US); John Mckenzie, San Carlos, CA (US); Daniel R. Burnett, San Francisco, CA (US); Eric Yu, San Francisco, CA (US)

(73) Assignee: Piccolo Medical, Inc., San Francisco, CA (US)

(*) Notice: Subject to any disclaimer, the term of this patent is extended or adjusted under 35 U.S.C. 154(b) by 271 days.

(21) Appl. No.: 16/790,379

(22) Filed: Feb. 13, 2020

(65) Prior Publication Data
US 2020/0281503 A1 Sep. 10, 2020

Related U.S. Application Data

(63) Continuation of application No. PCT/US2018/049177, filed on Aug. 31, 2018.
(Continued)

(51) Int. Cl.
*A61B 5/06* (2006.01)
*A61B 5/00* (2006.01)
*A61B 5/318* (2021.01)

(52) U.S. Cl.
CPC .............. *A61B 5/065* (2013.01); *A61B 5/318* (2021.01); *A61B 5/7257* (2013.01); *A61B 2562/02* (2013.01)

(58) Field of Classification Search
CPC ........................... A61B 5/065; A61B 2562/02
See application file for complete search history.

(56) References Cited

U.S. PATENT DOCUMENTS

| | | | | |
|---|---|---|---|---|
| 4,572,206 A | * | 2/1986 | Geddes ................ | A61B 5/0275 600/505 |
| 5,531,679 A | * | 7/1996 | Schulman ............ | A61N 1/0568 604/65 |

(Continued)

FOREIGN PATENT DOCUMENTS

| | | |
|---|---|---|
| JP | 2008-541799 | 11/2008 |
| JP | 2013-502269 | 1/2013 |
| WO | WO 2019/046769 | 3/2019 |

*Primary Examiner* — Rochelle D Turchen
(74) *Attorney, Agent, or Firm* — Levine Bagade Han LLP

(57) ABSTRACT

Devices and methods for vascular navigation, assessment and/or diagnosis are disclosed where a location detection system generally includes an elongate body defining a lumen at least partially along a length of the elongate body. One or more sensors are positioned near or at a distal tip of the elongate body and one or more openings are defined along the elongate body in proximity to the one or more sensors. The one or more openings are configured to control a boundary distance between the one or more sensors and a fluid with a parameter of a known initial value when emitted from the one or more openings. A controller is in communication with the one or more sensors and is configured to track a change in the parameter relating to concentration over the one or more sensors and determine a position of the one or more sensors within a body.

38 Claims, 66 Drawing Sheets

Related U.S. Application Data

(60) Provisional application No. 62/580,238, filed on Nov. 1, 2017, provisional application No. 62/563,604, filed on Sep. 26, 2017, provisional application No. 62/553,023, filed on Aug. 31, 2017.

(56) References Cited

U.S. PATENT DOCUMENTS

| | | |
|---|---|---|
| 9,743,994 B2 | 8/2017 | Wenzel et al. |
| 2006/0229589 A1* | 10/2006 | Itou .................... A61M 25/005 604/526 |
| 2007/0137296 A1 | 6/2007 | Krivitski et al. |
| 2007/0219441 A1 | 9/2007 | Carlin et al. |
| 2010/0076320 A1 | 3/2010 | Petersen et al. |
| 2011/0060229 A1 | 3/2011 | Hulvershorn et al. |
| 2012/0291943 A1 | 11/2012 | Curry |
| 2015/0018762 A1* | 1/2015 | Fierens ............... A61M 1/3621 604/99.02 |
| 2016/0067449 A1 | 3/2016 | Misener et al. |
| 2016/0256224 A1 | 9/2016 | Wenzel et al. |
| 2016/0374612 A9 | 12/2016 | Hulvershorn et al. |
| 2017/0231573 A1* | 8/2017 | Reiner ................. A61B 5/6861 600/301 |

* cited by examiner

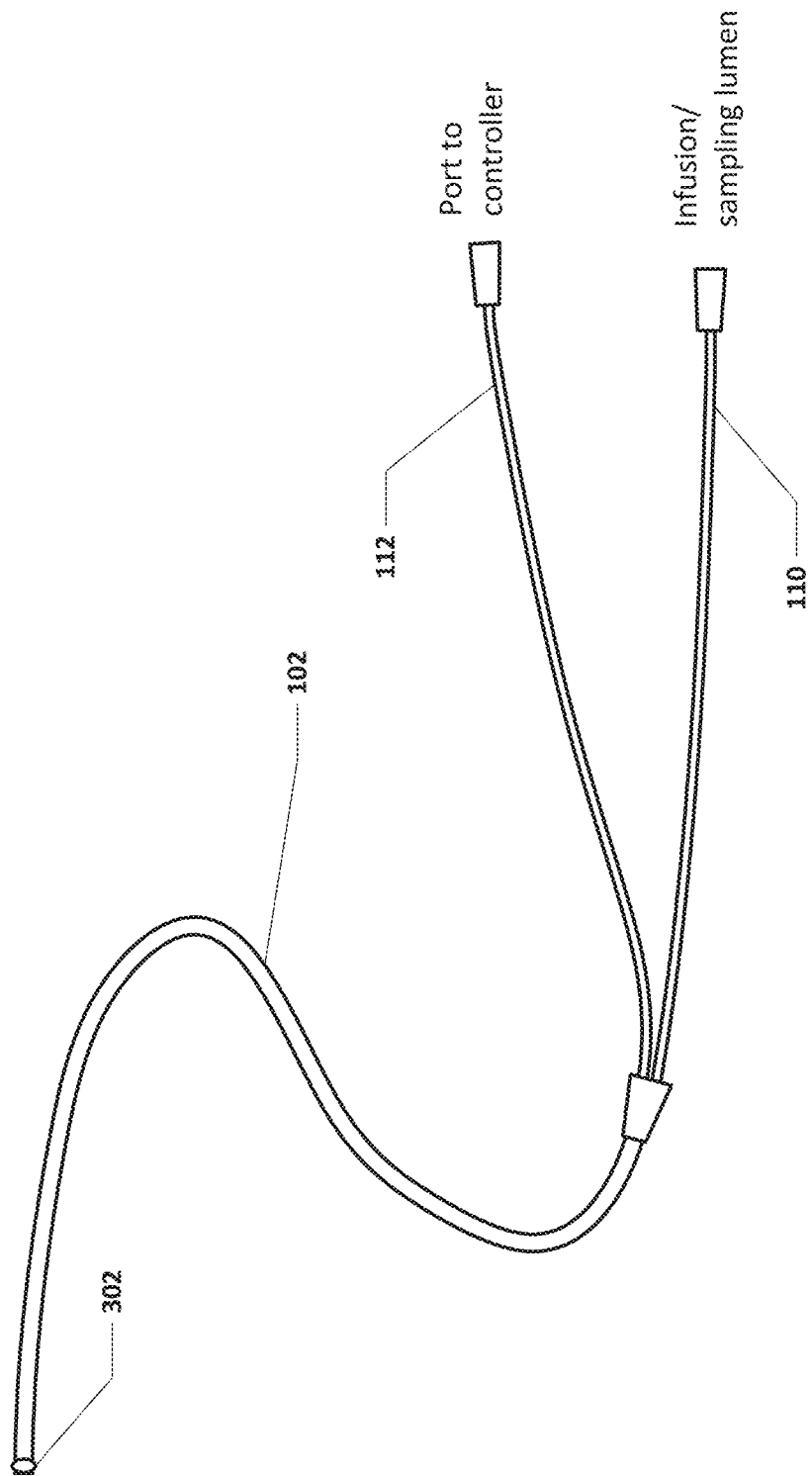

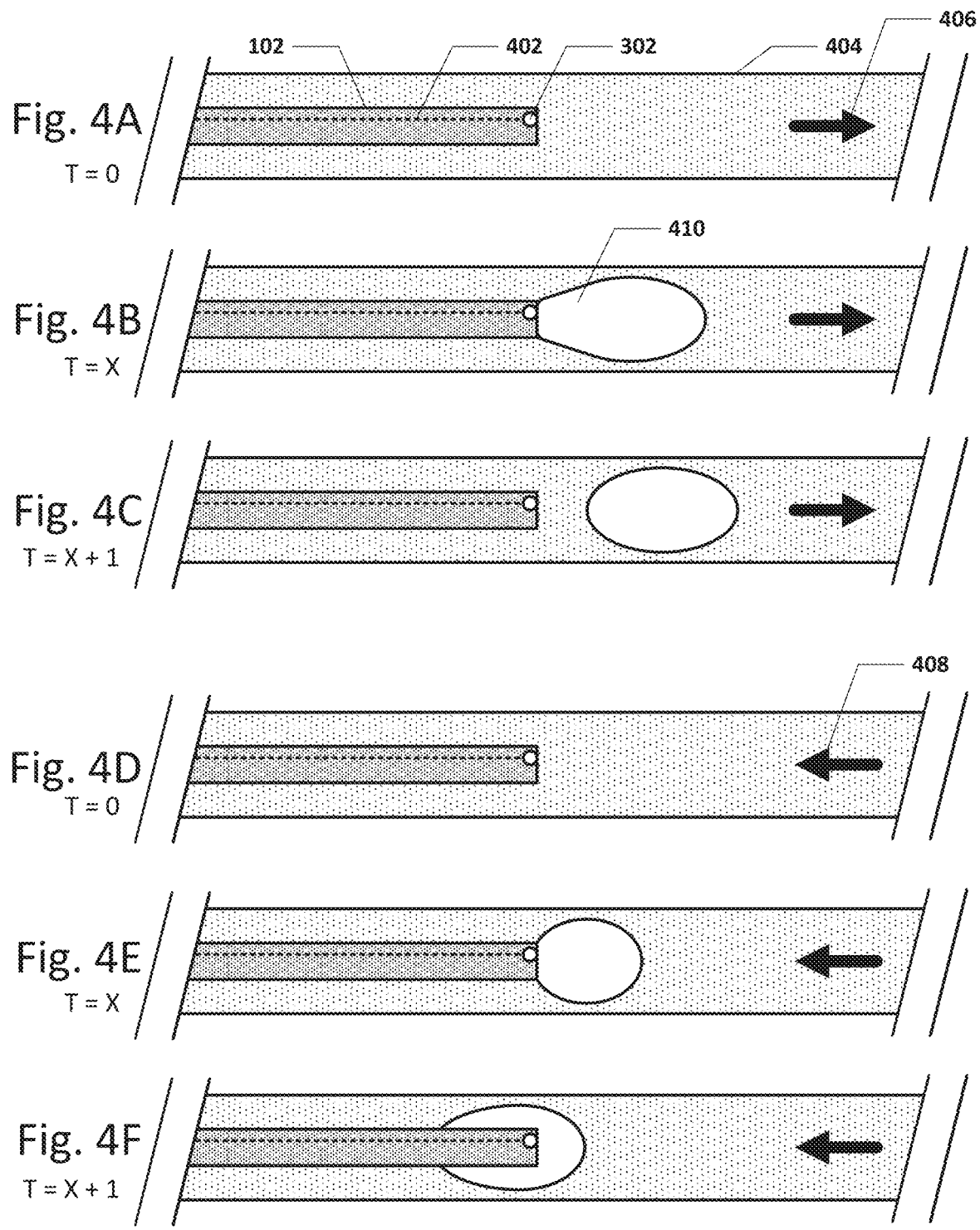

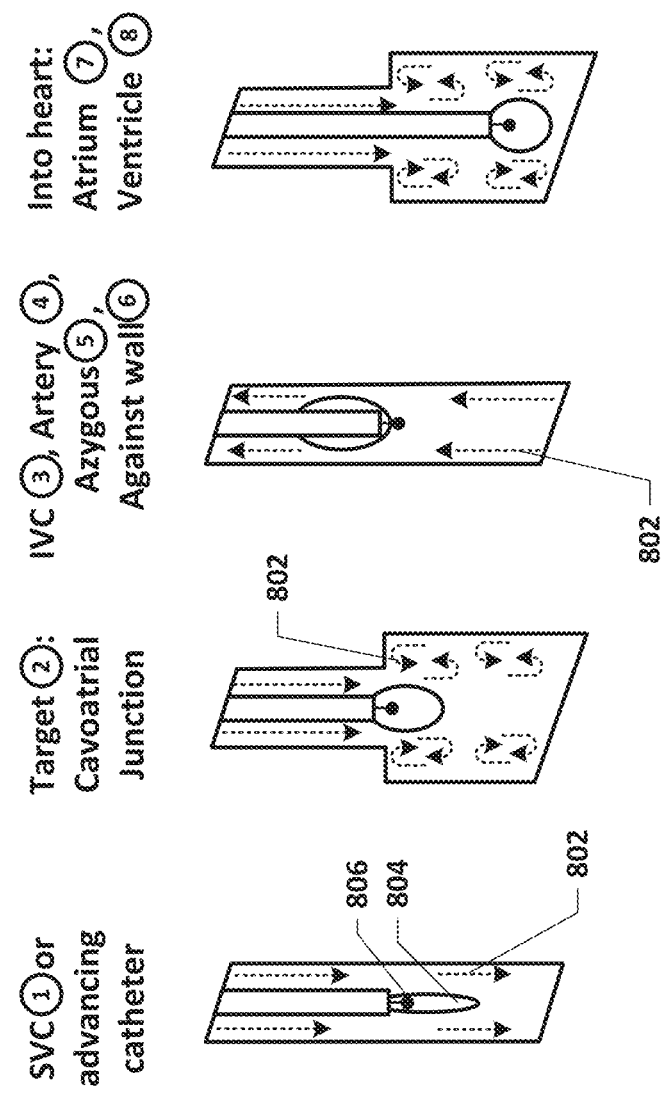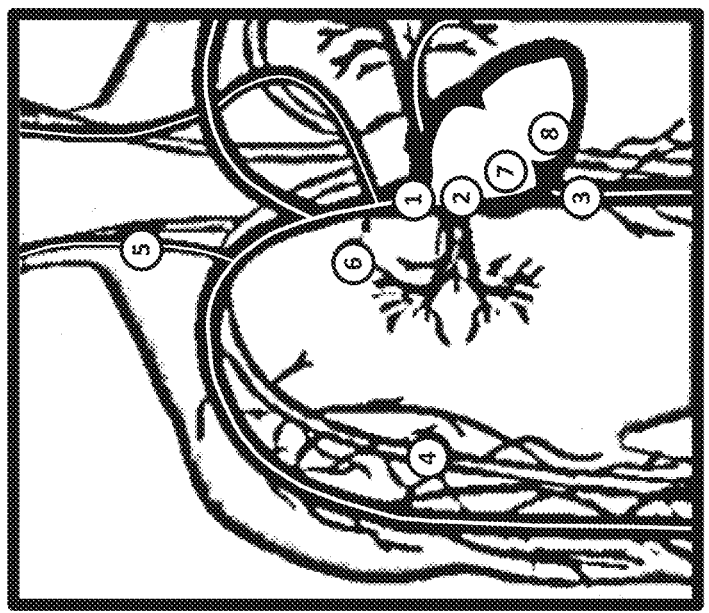
Fig. 8

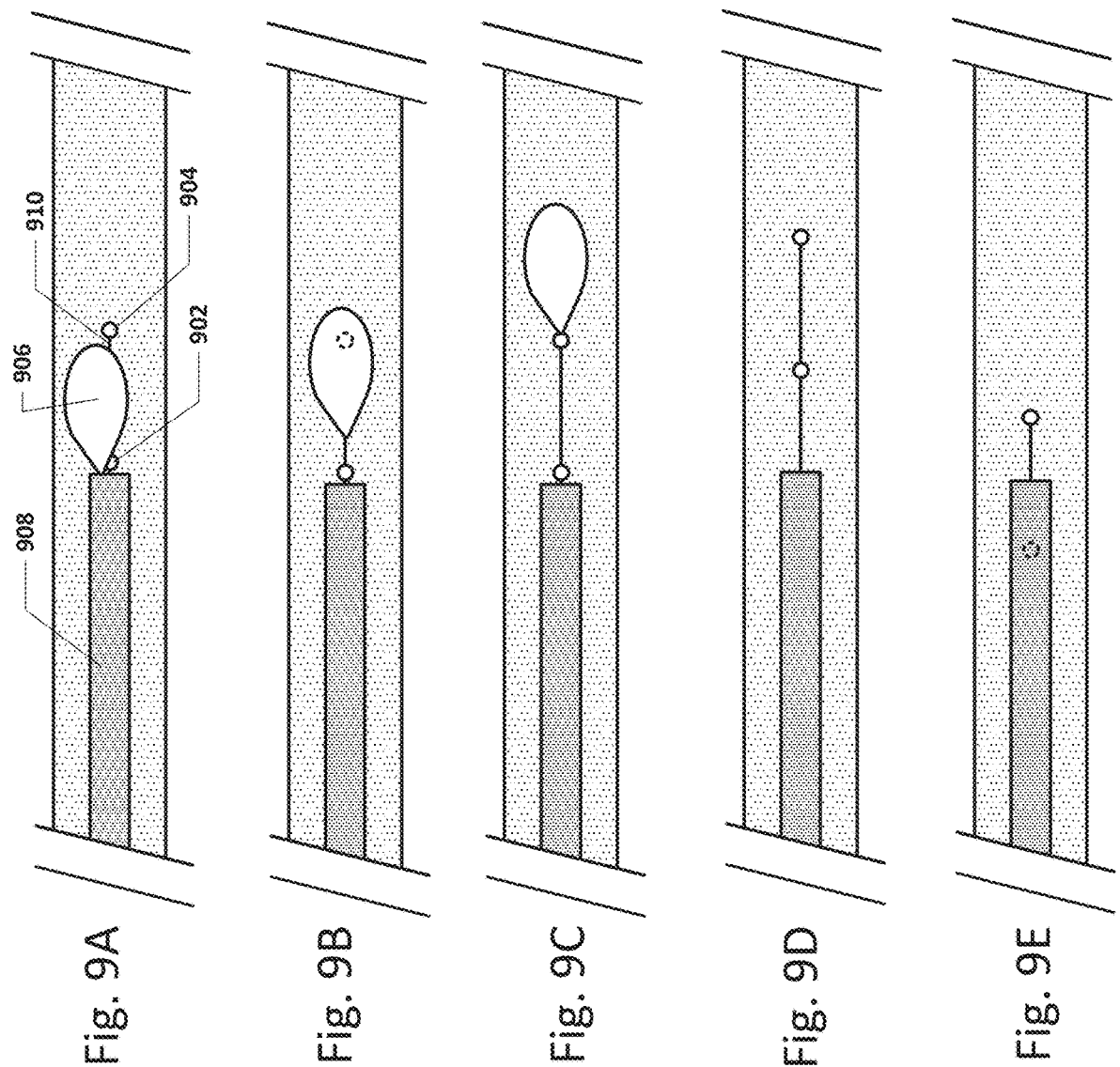

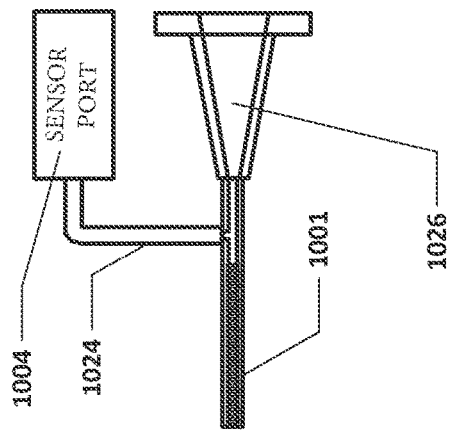
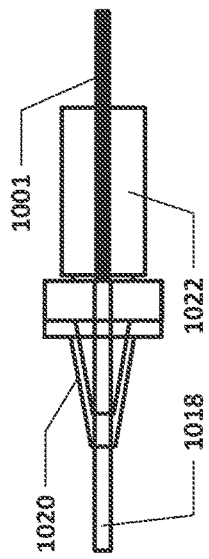
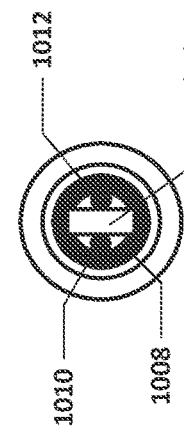
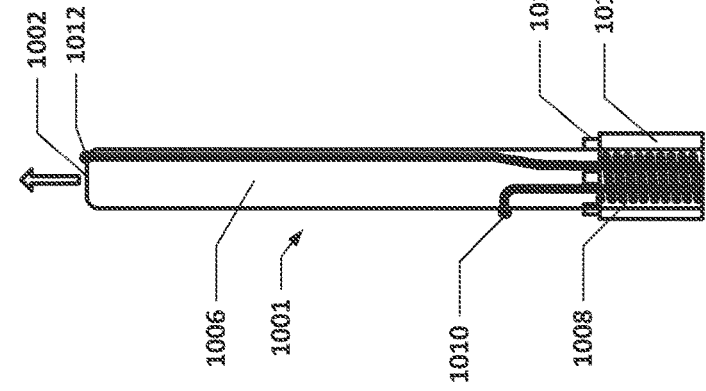
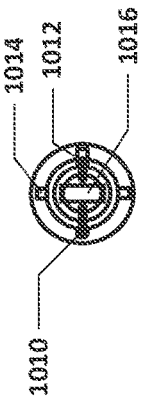

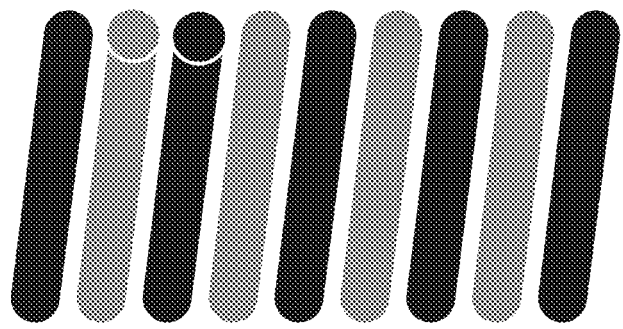
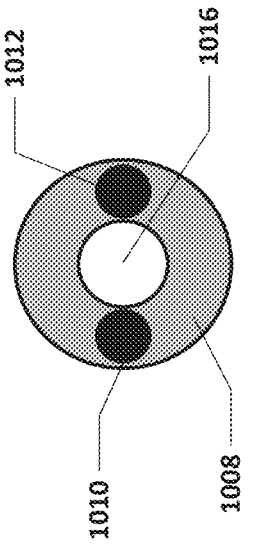
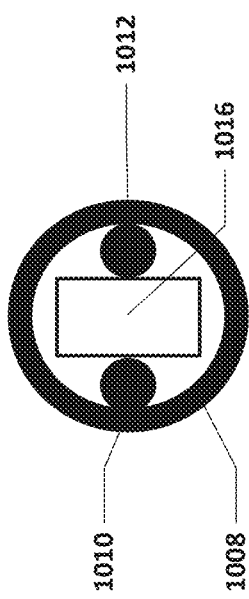
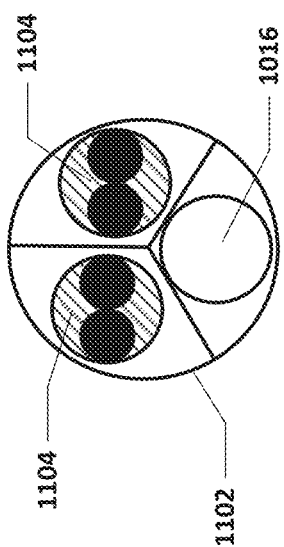

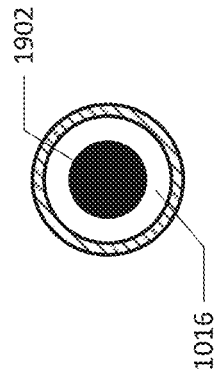
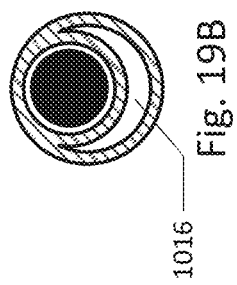
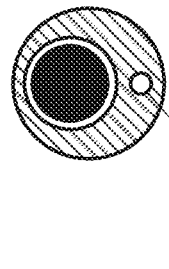
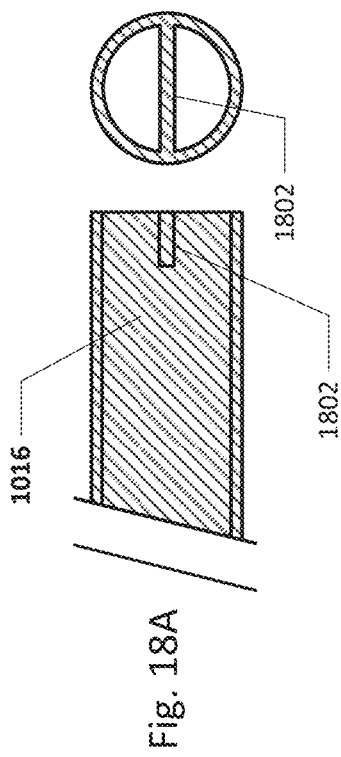
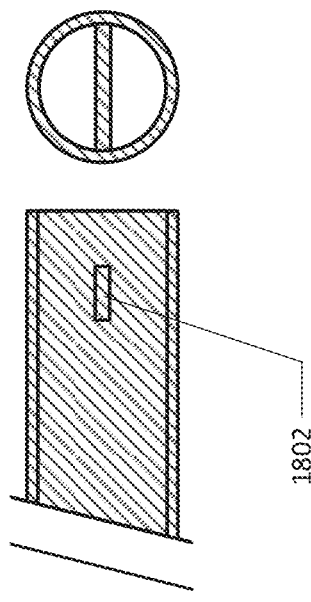

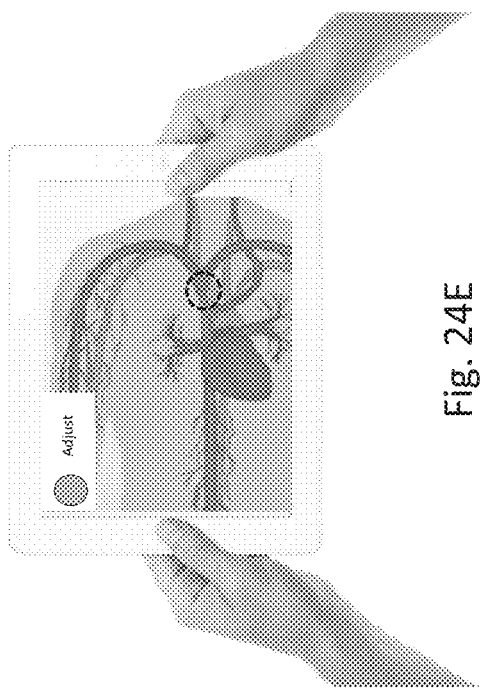

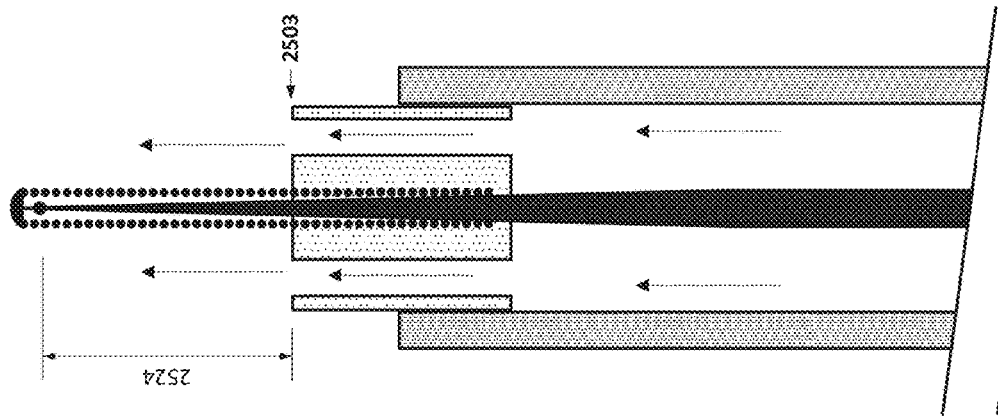
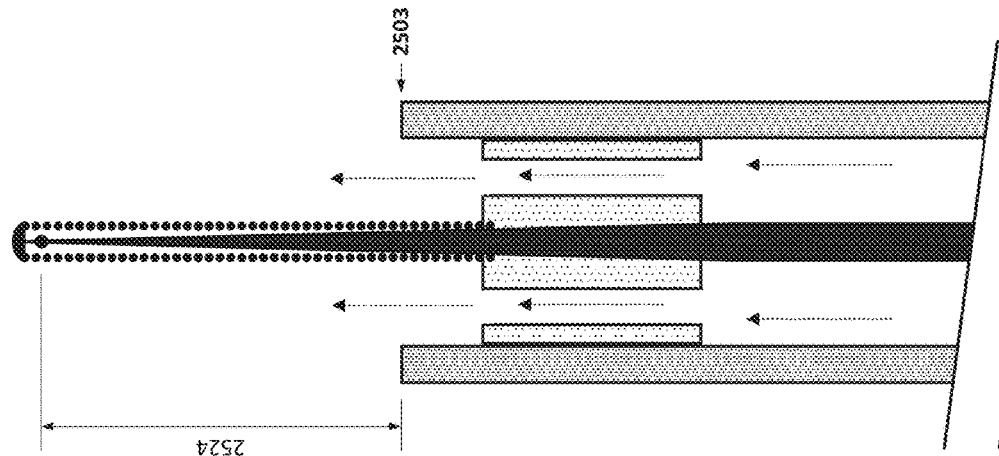
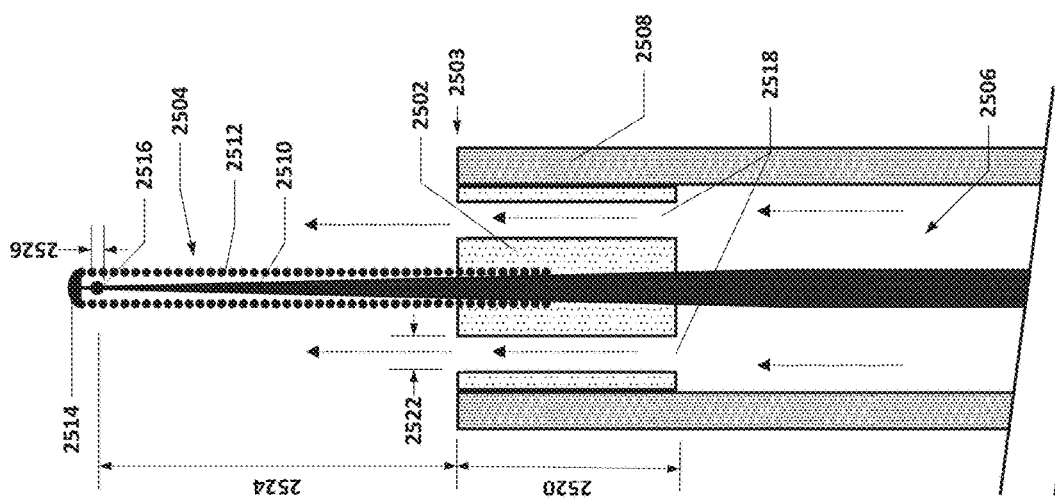

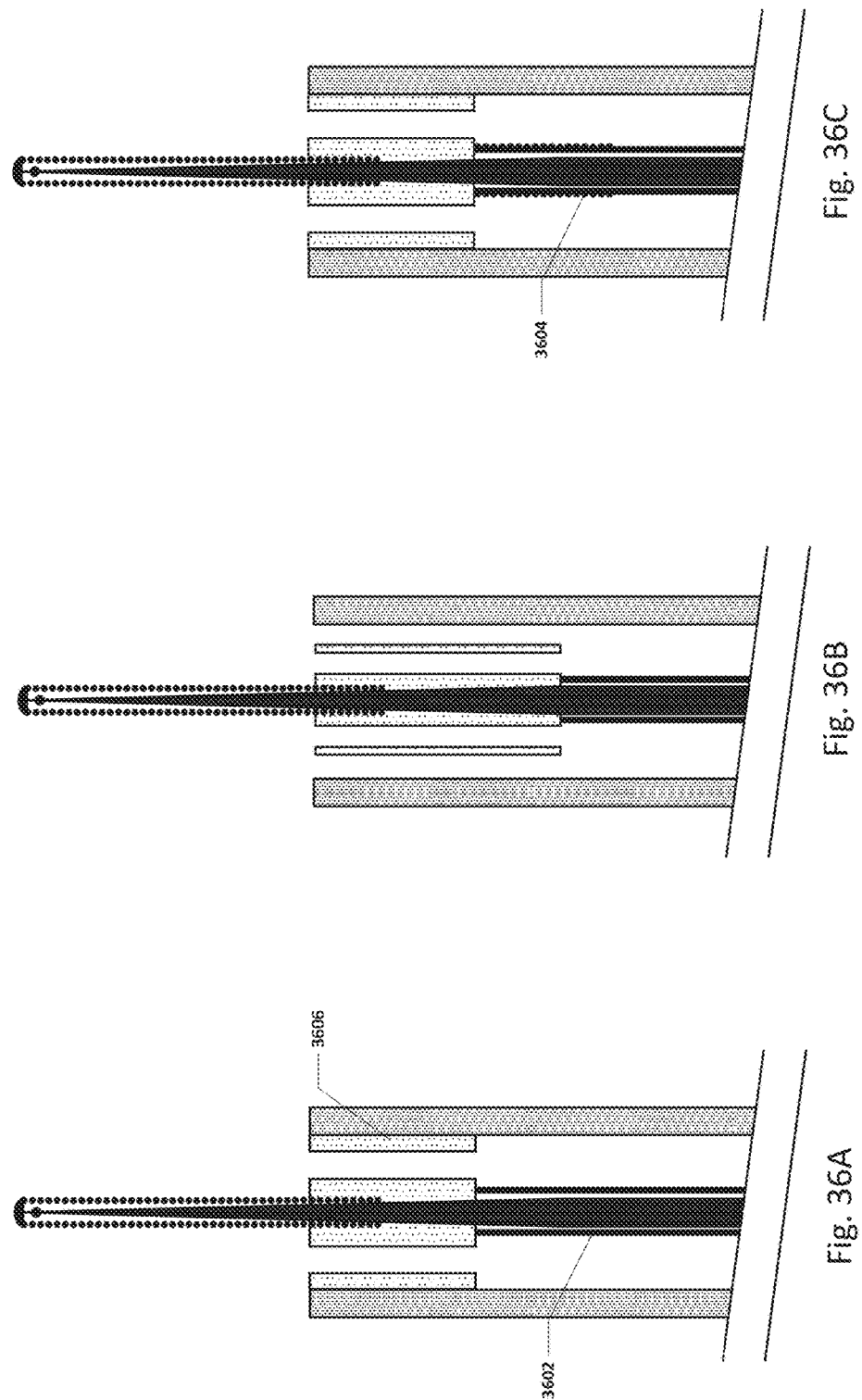

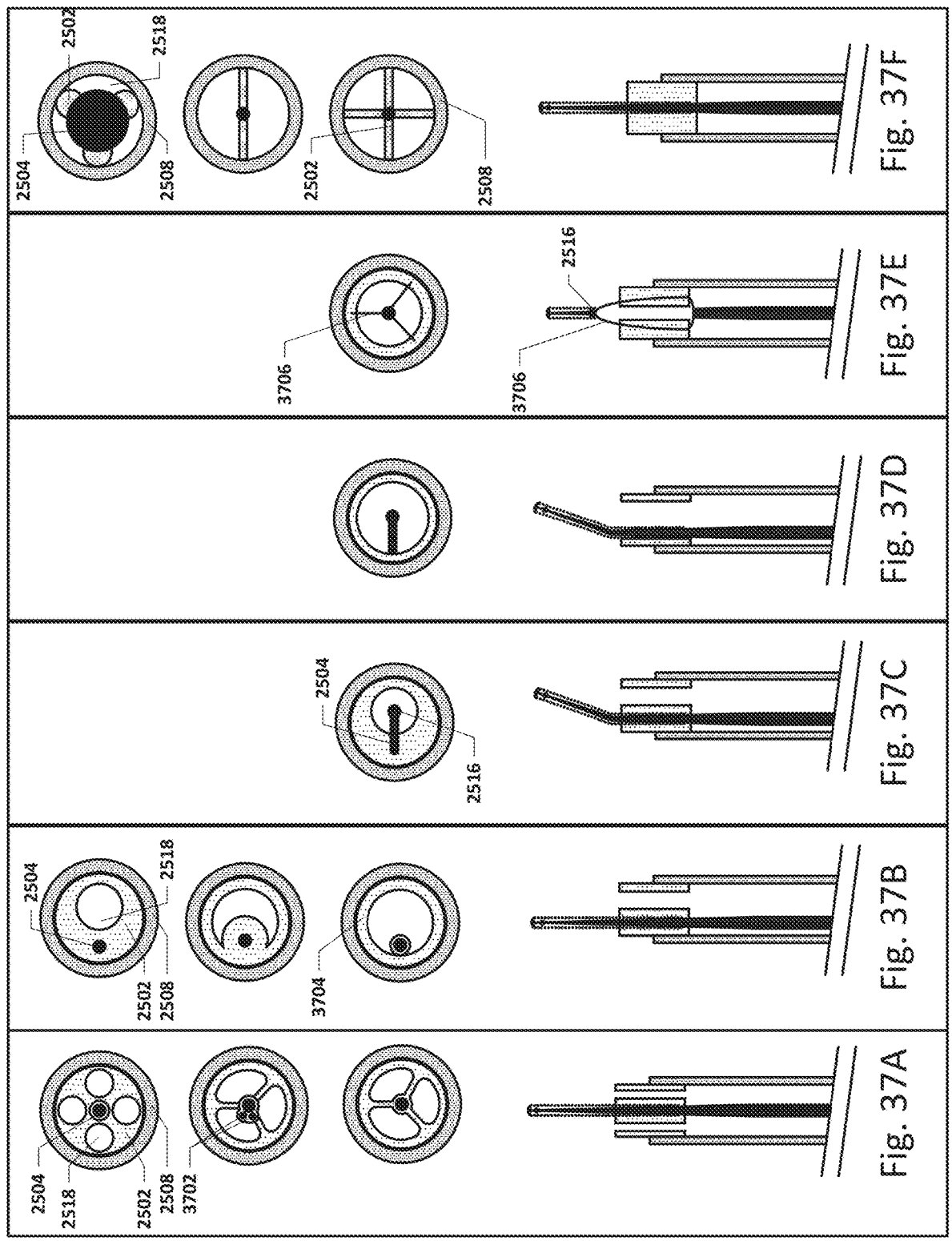

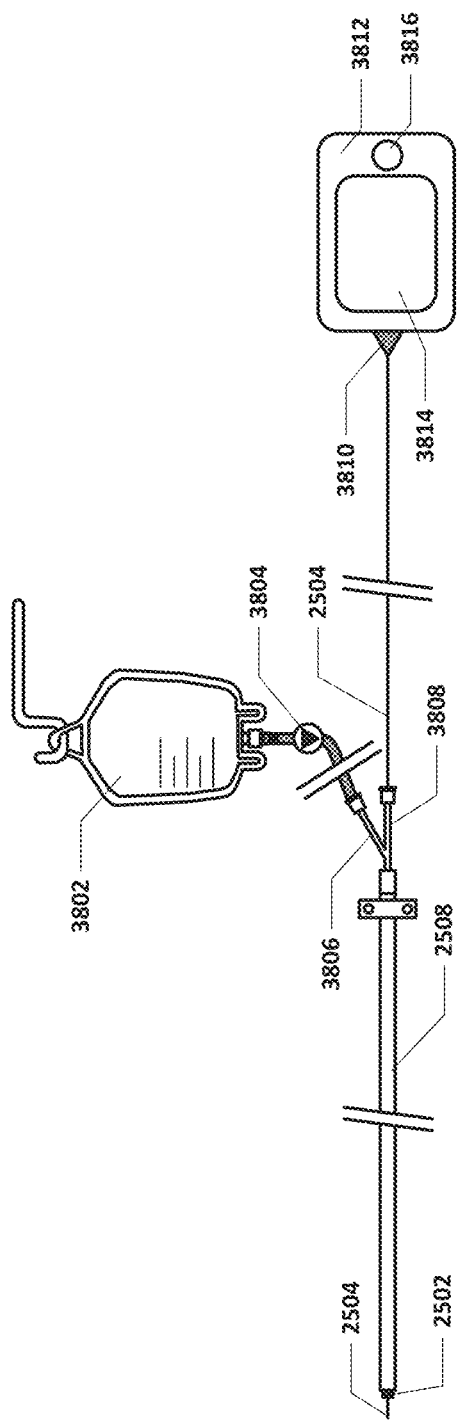
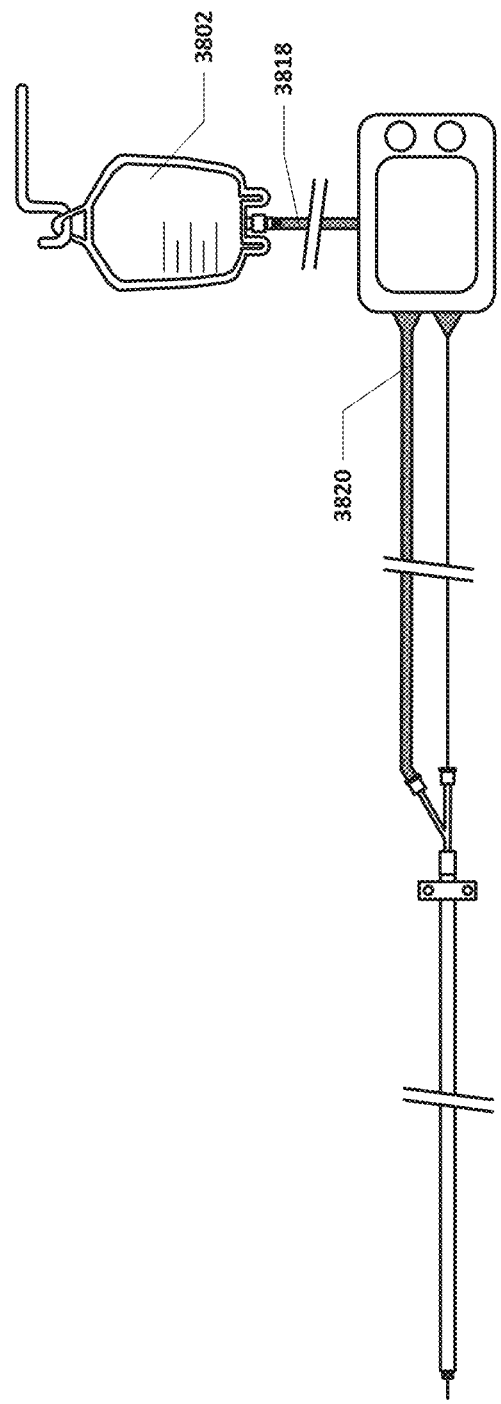
Fig. 38A
Fig. 38B

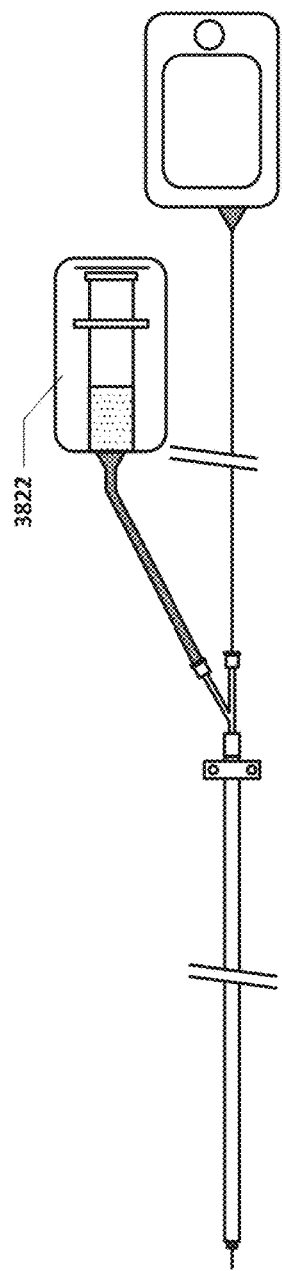
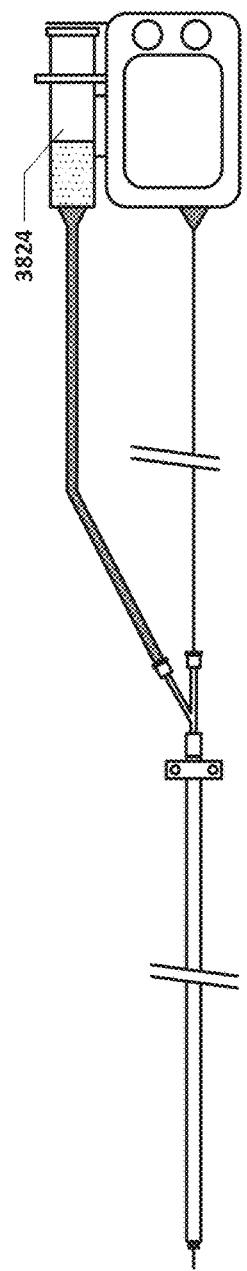
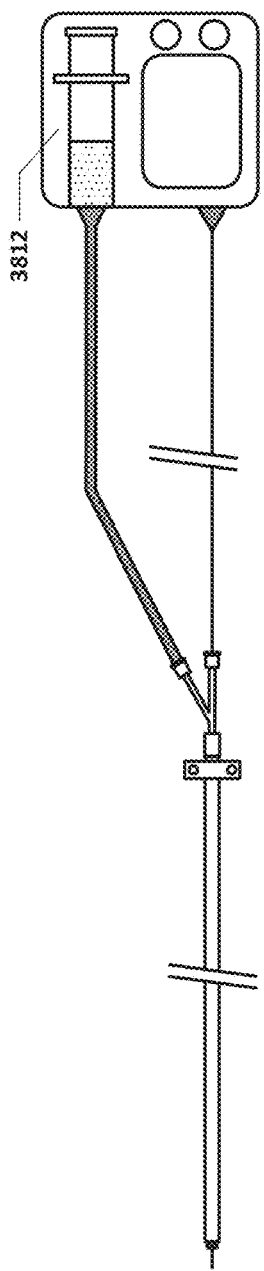
Fig. 38C
Fig. 38D
Fig. 38E

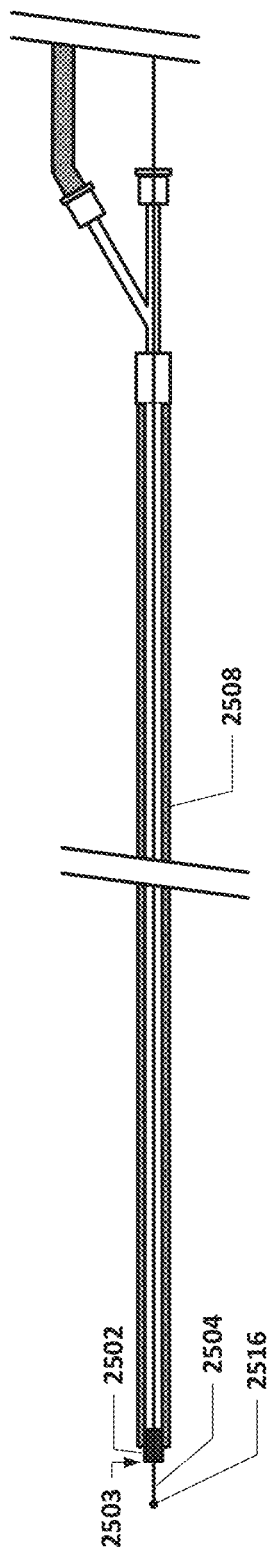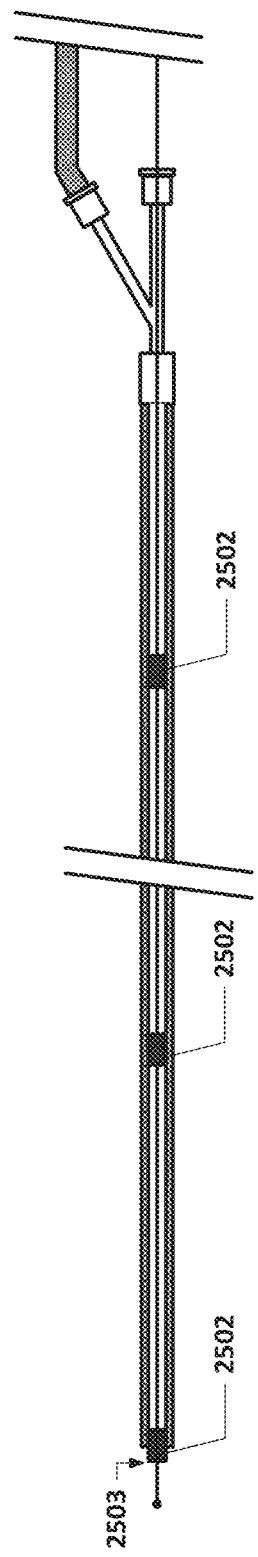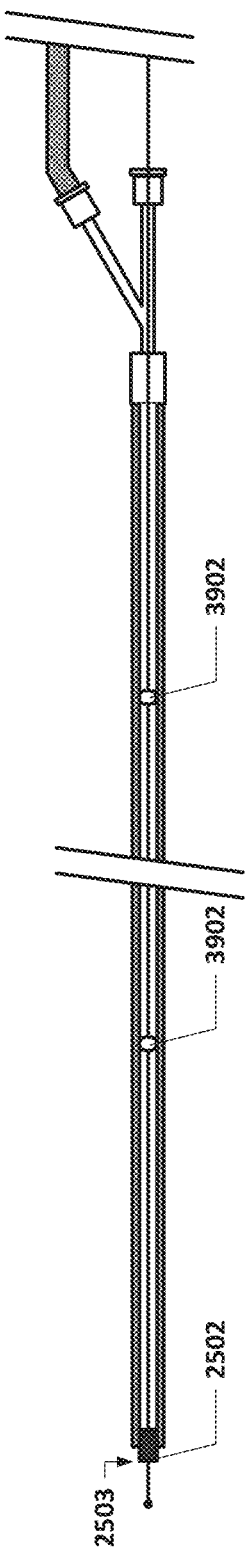

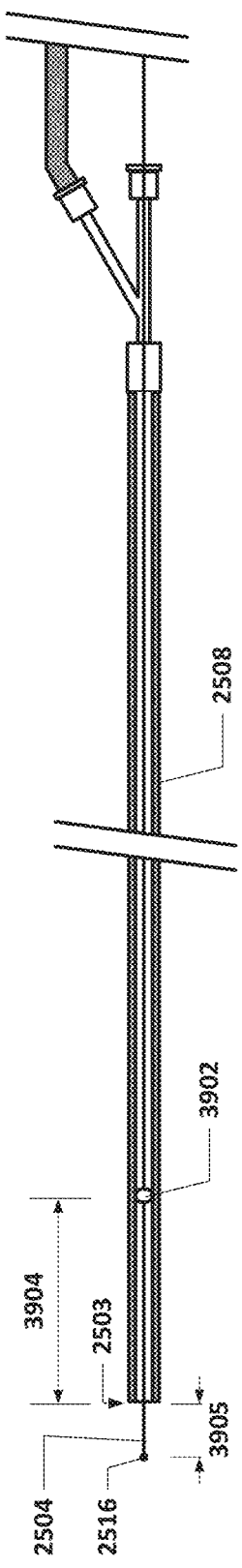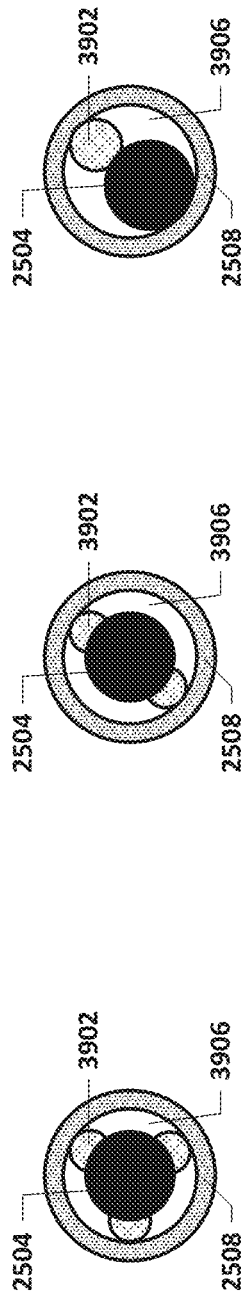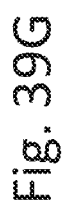

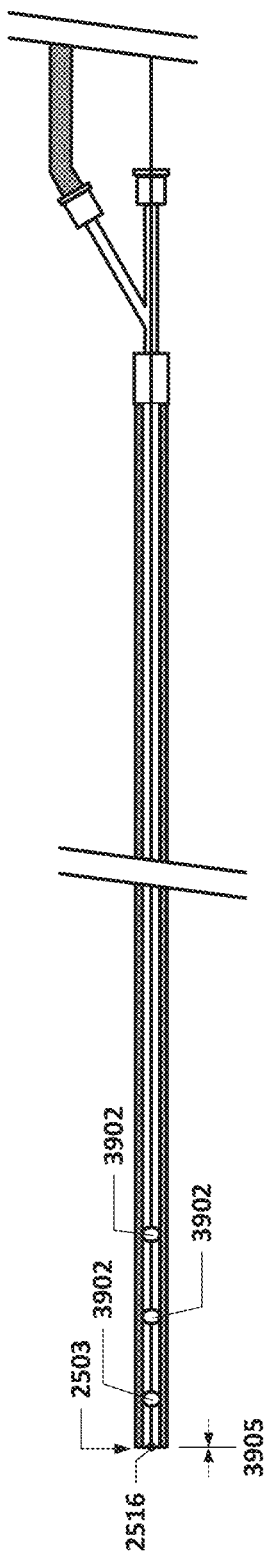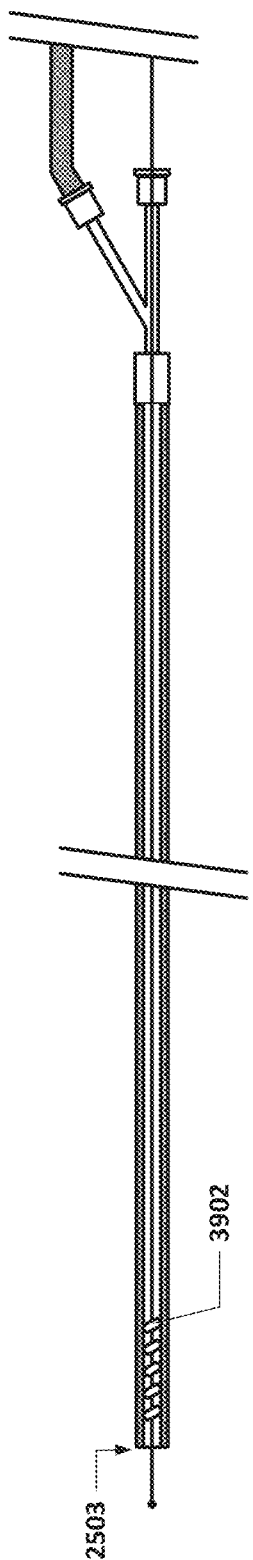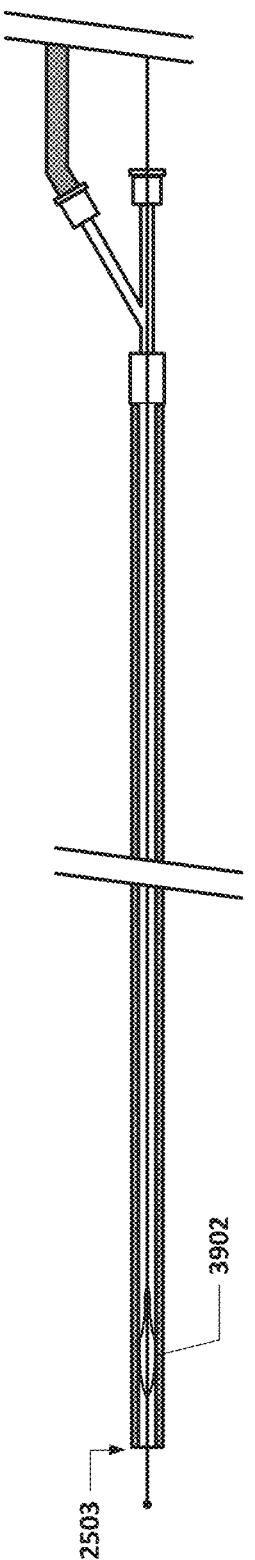

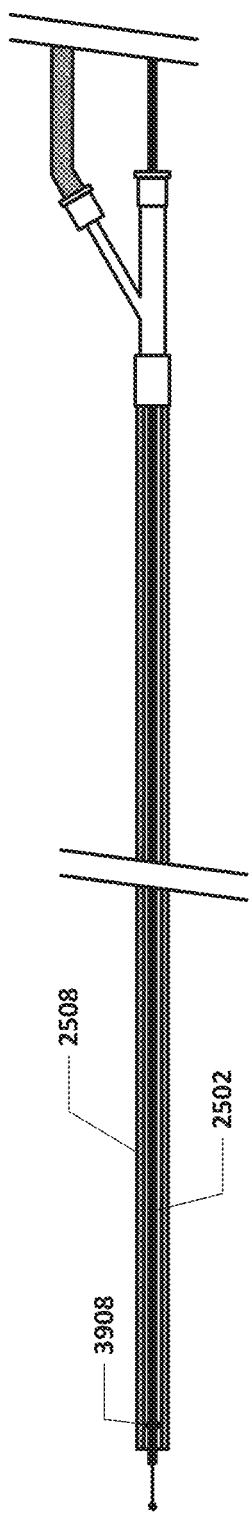

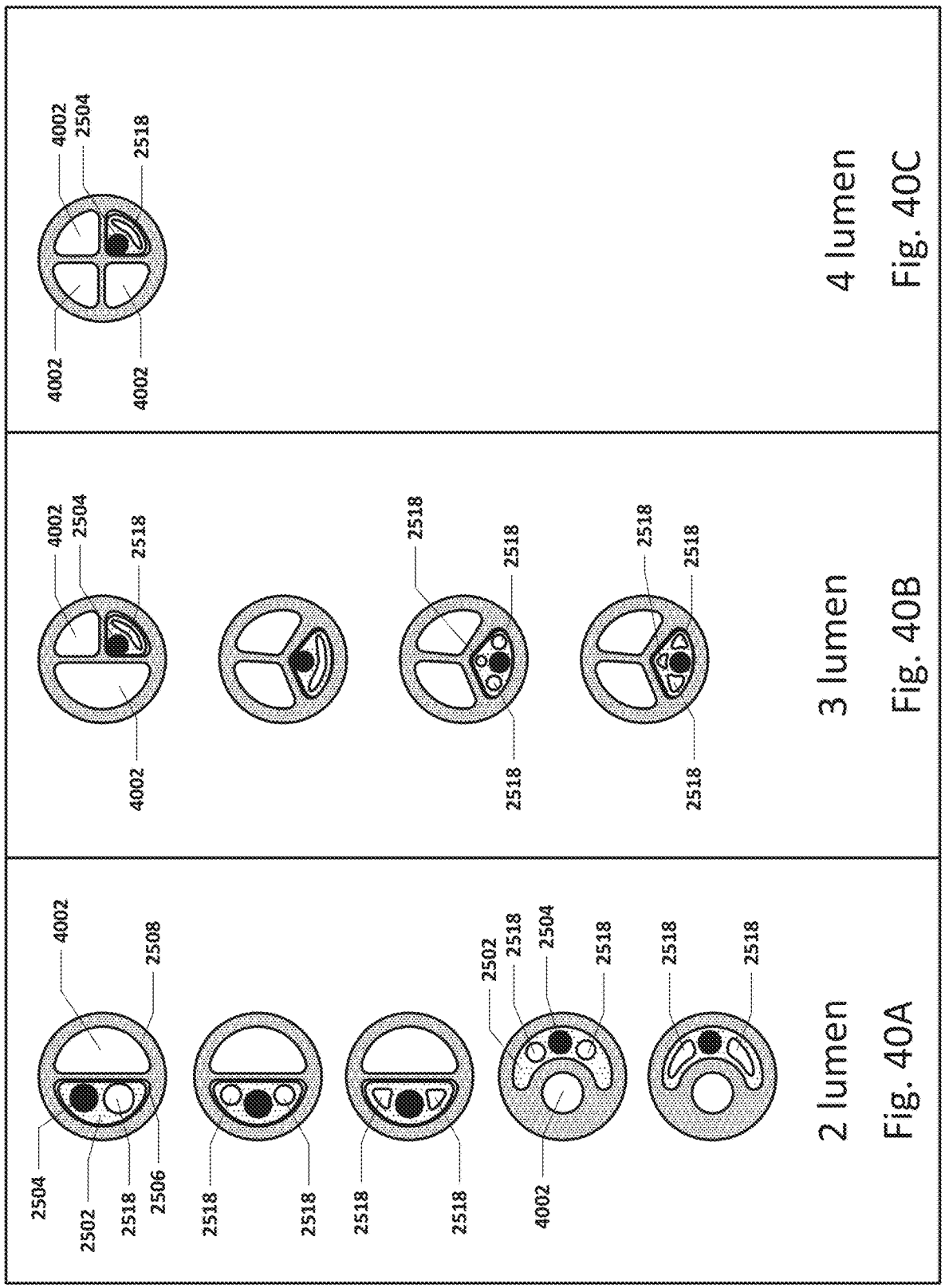

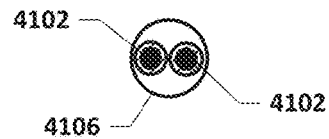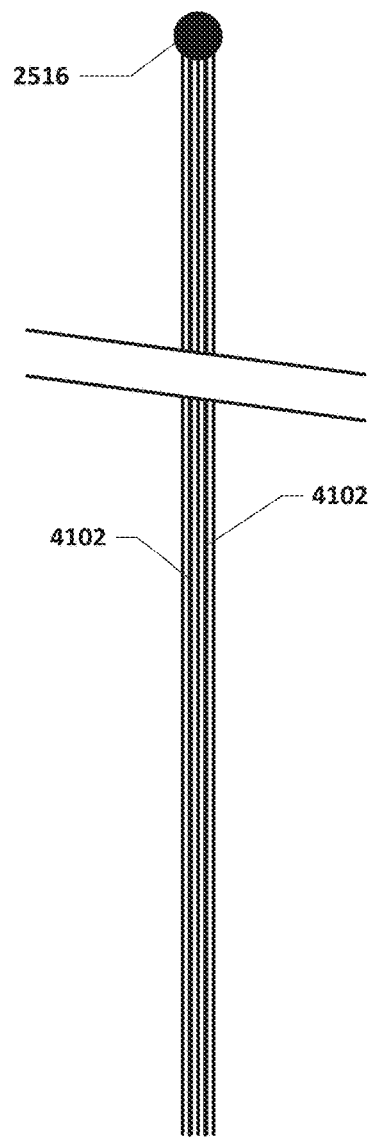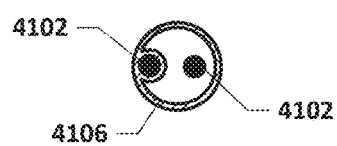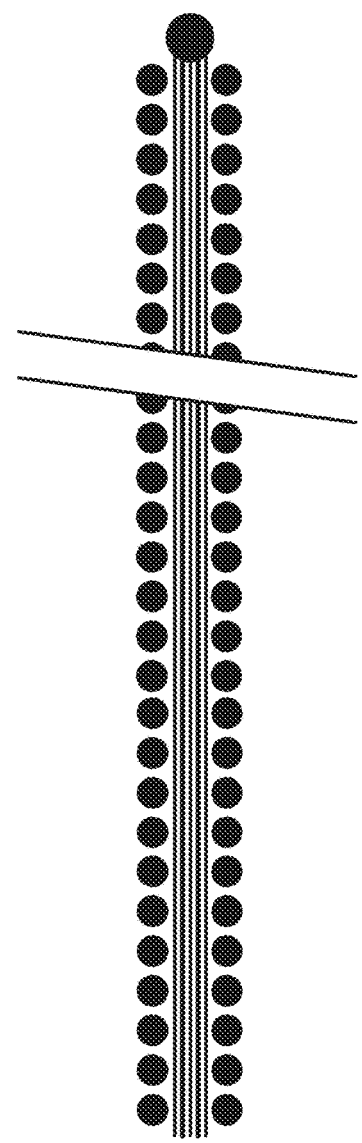
Fig. 42A    Fig. 42B    Fig. 42C n = number of openings

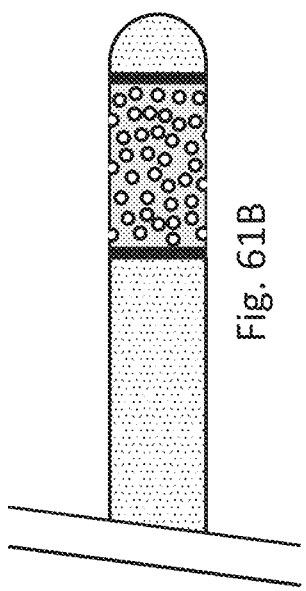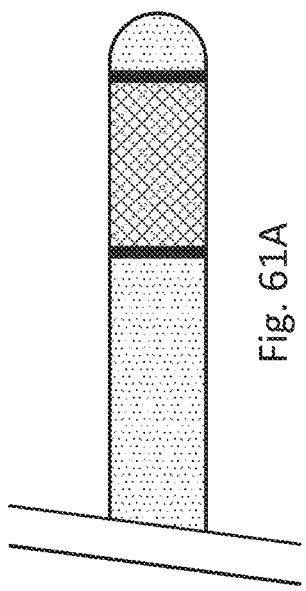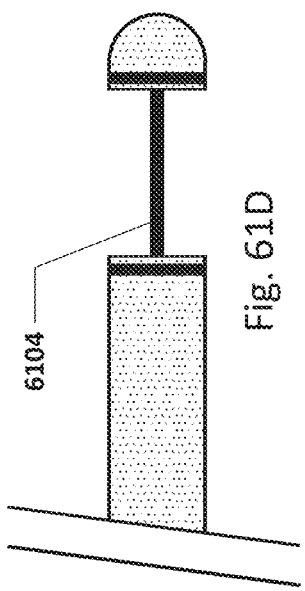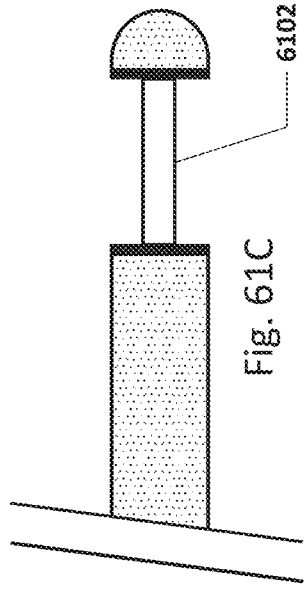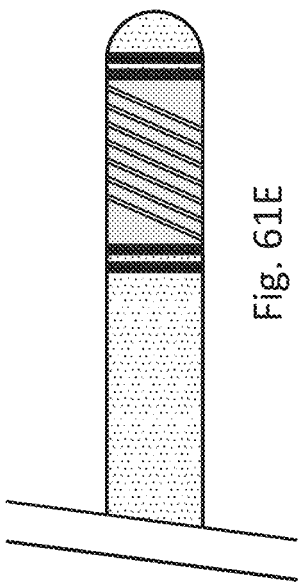

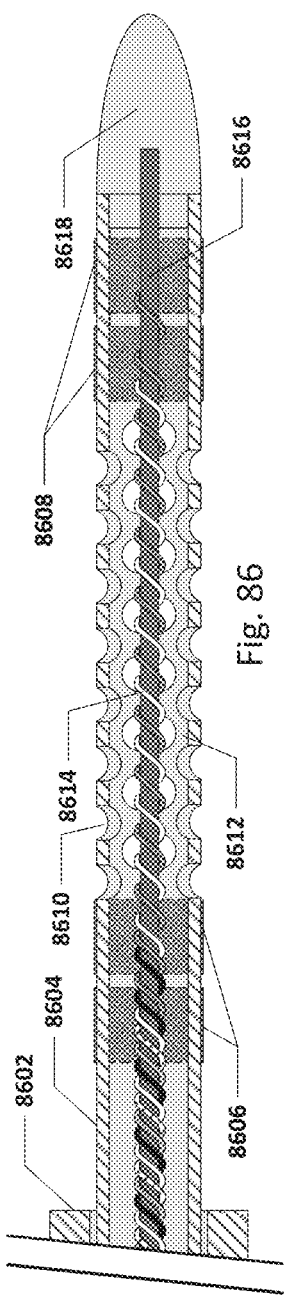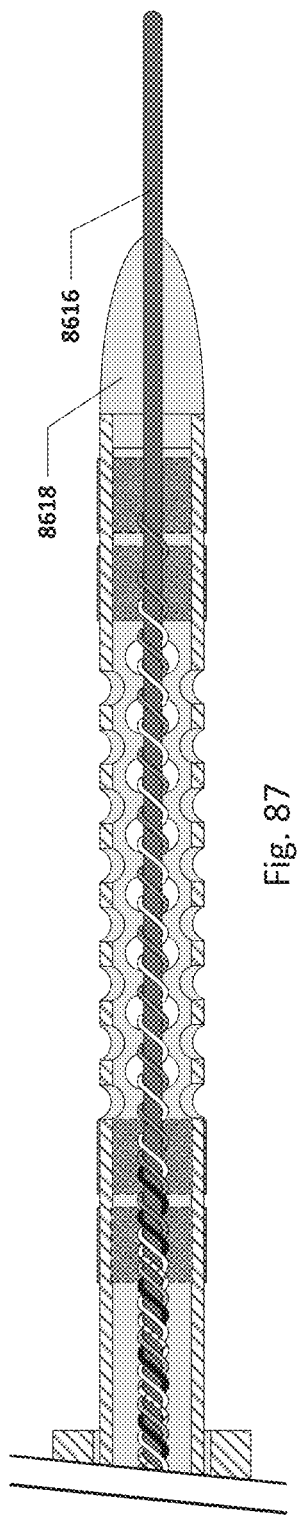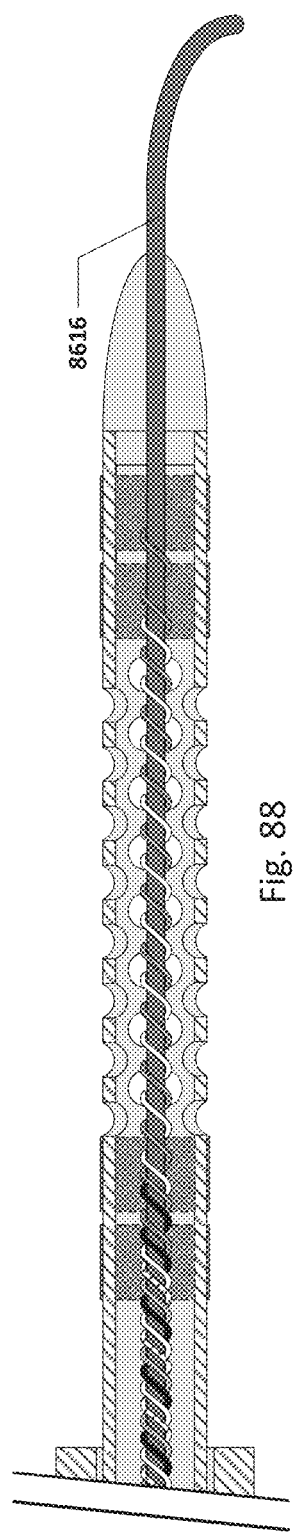

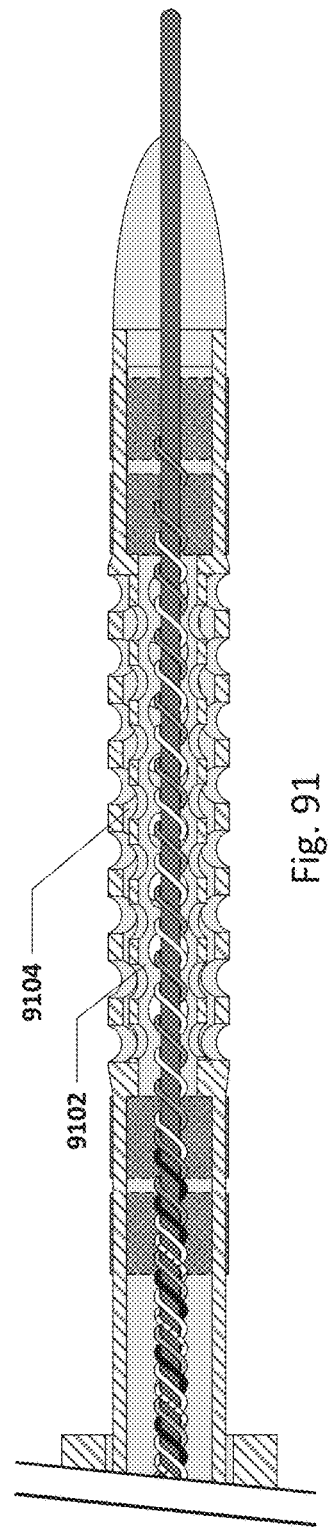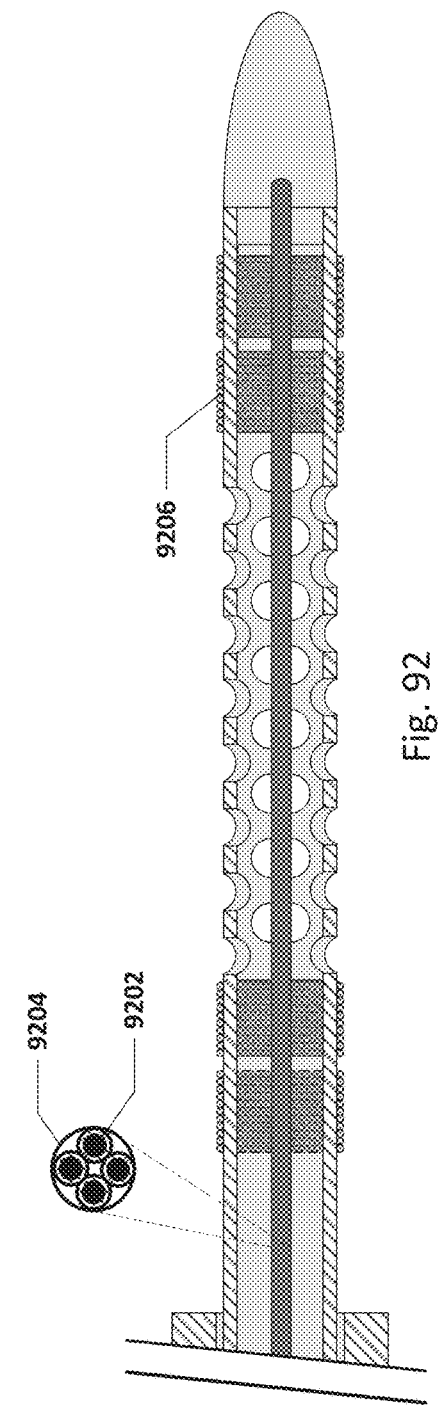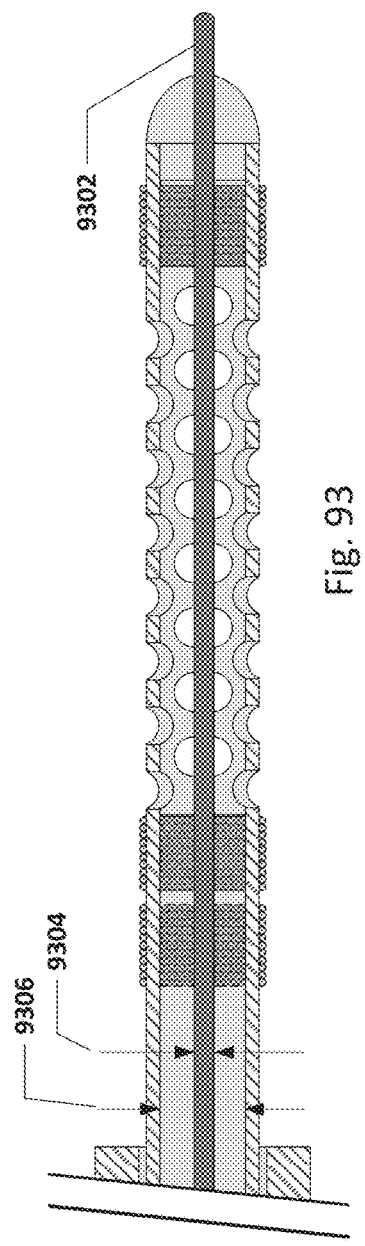

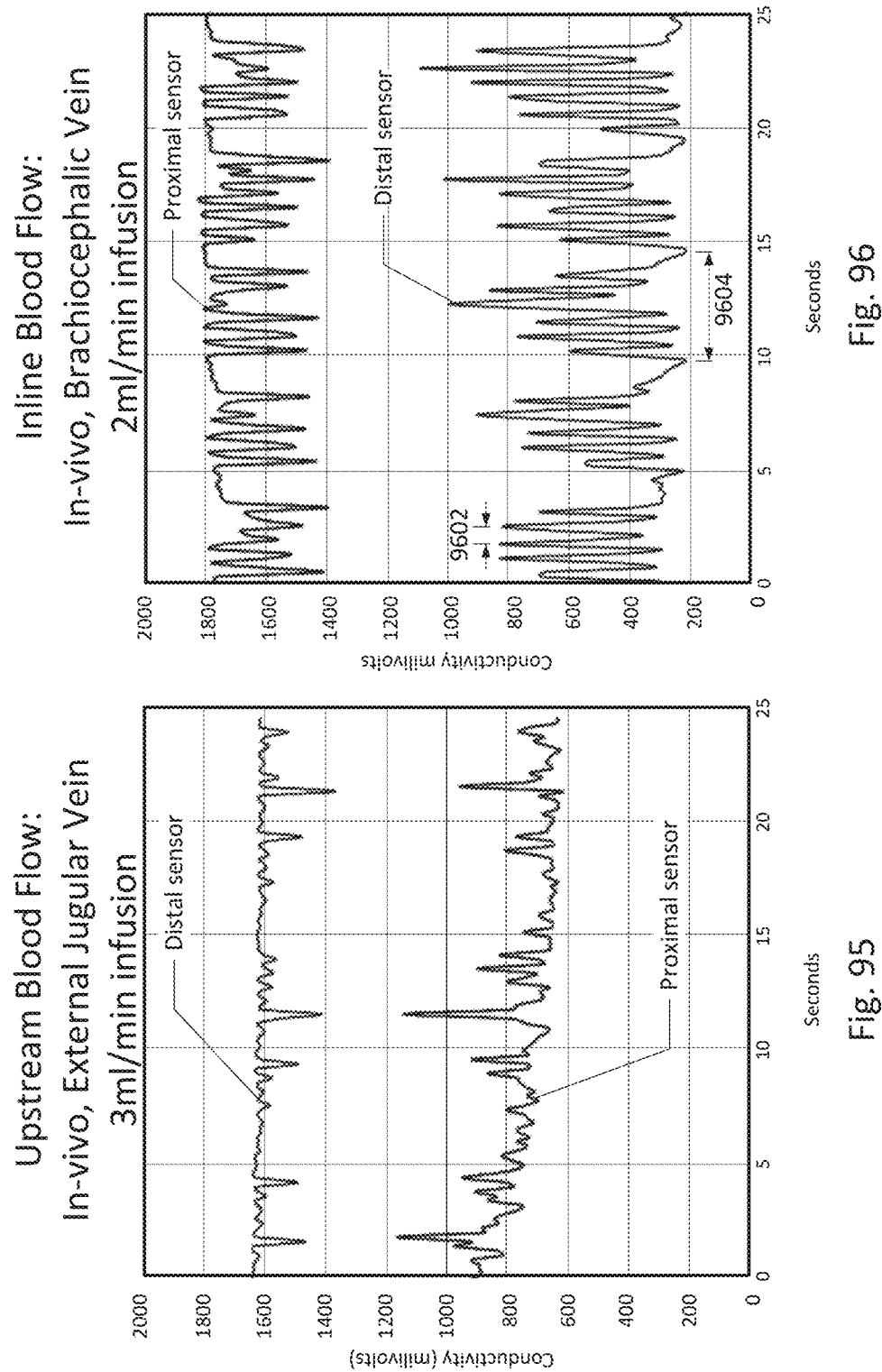

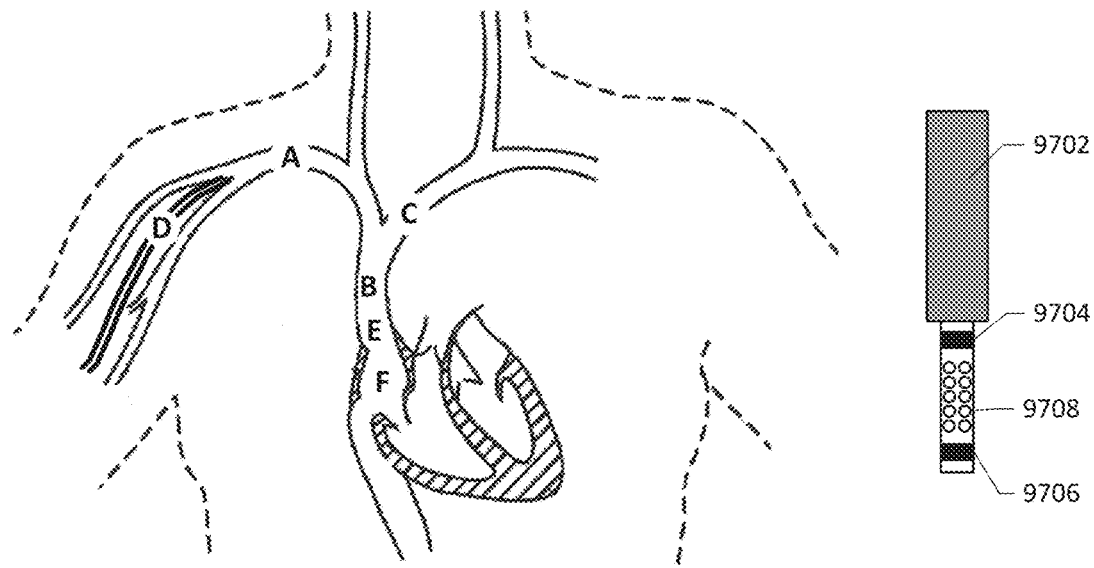

| Location | Vein Ⓐ SVC Ⓑ | Contralateral Ⓒ Artery Ⓓ | CAJ Ⓔ | Right Atrium Ⓕ |
|---|---|---|---|---|
| Flow Type | Inline flow | Counter flow | High turbulence Pulsatile Bi-directional | High turbulence Multi-directional |
| Infusate dispersion | | | | |
| Signal magnitude | Signature 1 | Signature 2 | Signature 3 | Signature 4 |
| Signal pulsatility due to heartbeat | | | | |
| Signal due to heart electrical activity | | | | |
| Other | | | | |
| Controller instructions | Continue advancing | Stop advancing, retract catheter | Target found | In heart, stop advancing, retract catheter |

Fig. 97

DEVICES AND METHODS FOR VASCULAR NAVIGATION, ASSESSMENT AND/OR DIAGNOSIS

CROSS-REFERENCE TO RELATED APPLICATIONS

This application is a continuation of International Patent Application No. PCT/US2018/049177 filed Aug. 31, 2018, which claims the benefit of priority to U.S. Provisional Application No. 62/553,023 filed Aug. 31, 2017, U.S. Provisional Application No. 62/563,604 filed Sep. 26, 2017 and U.S. Provisional Application No. 62/580,238 filed Nov. 1, 2017, each of which is incorporated herein by reference in its entirety.

FIELD OF THE INVENTION

The present invention relates to devices and methods for vascular navigation, assessment, and/or diagnosis.

INCORPORATION BY REFERENCE

All publications and patent applications mentioned in this specification are herein incorporated by reference to the same extent as if each such individual publication or patent application were specifically and individually indicated to be so incorporated by reference.

BACKGROUND OF THE INVENTION

A central vascular catheter (vascular catheter), also known as central line, central venous line or central venous access catheter, is a catheter placed into a large vein in the neck (internal jugular vein), chest (subclavian vein or axillary vein), arm or groin (femoral vein). It is primarily used to administer medication or fluids, obtain blood tests (such as central venous oxygen saturation), and measure central venous pressure.

A peripherally inserted central catheter (PICC or PIC line) is a form of vascular catheter that can be used for a prolonged period of time and/or for administration of substances. It is a catheter that enters the body through the skin (percutaneously) at a peripheral site, extends to the superior vena cava (a central venous trunk), and may remain in place for days or weeks.

Placing the catheter (PICC, central vascular catheter or related vascular catheter, referred to herein as "vascular catheter" or "catheter") in the ideal location can be challenging. The catheter may be mistakenly inserted into an artery instead of a vein, or into the incorrect vein or incorrect venous branch or advanced too far or into/along a vessel wall. Ideally, the catheter tip is placed in the superior vena cava/cavo-atrial junction (SVC-CAJ or CAJ), or the lower one third of the superior vena cava.

Correct placement currently is determined by taking a physical measurement of the distance from the catheter entry point to the estimated location of the lower one third of the superior vena cava or CAJ. There are several challenges with current techniques. First, the catheter may enter into an artery instead of a vein. Second, a catheter may be advanced down the incorrect branch of the vein tree. The catheter may advance down an azygous vein, a thoracic vein, a jugular vein, or any number of additional veins on the branch. Third, a catheter may be advanced past the superior vena cava and into the heart or into the inferior vena cava. This can be a dangerous situation. Fourth, a catheter may advance up against, or embed in, a vessel wall which can prevent fluid delivery or fluid draw. Fifth, because the gold standard for catheter placement is essentially blind, placement verification needs to be confirmed with a chest x-ray which adds additional cost and time. Sixth, the estimated distance to the lower one third of the superior vena cava or CAJ may be inaccurate.

There is a need for a relatively easy and accurate way of navigating a vascular catheter by accurately identifying the location of the tip of the catheter as it is advanced to its targeted location.

SUMMARY OF THE INVENTION

The present invention includes vascular catheter location and navigation devices and methods which determine the location of the tip of a vascular catheter using the introduction of a medium (or injectate) with a measurable parameter (temperature, light reflection, sound reflection, conductance, impedance, etc.) and sensing and measuring the measurable parameter as the catheter is advanced within a flowing fluid, such as blood flow in a blood vessel. Measurements of the parameter are tracked over time, recorded and analyzed. The value of the parameter and/or the shape of the parameter value vs. time curve may be used in the analysis. For example, curve amplitude, variability, pulsatility, phase, standard deviation, slope, etc. may be used in the analysis of catheter location.

Flow direction, characteristics, profiles, and types, with respect to the catheter and catheter tip can provide a vast array of information on catheter positioning during placement, after initial or subsequent placement, after the catheter has been in place for a period of time, and/or during catheter withdrawal.

Devices and methods disclosed herein can be used to inform the user of one or more of the following conditions: insertion, placement or advancement of the catheter into an artery rather than a vein; insertion, placement or advancement of the catheter into an undesired vein branch; placement or advancement of the catheter too near, into, or past the heart; or placement of the catheter tip up against, or embedded in, a wall of a vessel, or insufficient advancement of the catheter. Each of these scenarios is described in detail herein.

Blood flow characteristics and direction can help determine if the catheter is in an artery or a vein. In the case of a vein, the blood will generally be flowing more slowly toward the heart, while with the artery the blood will generally be flowing more quickly away from the heart. At least the blood flow direction and speed with respect to the catheter will be different depending on whether the catheter is in an artery or vein. Other flow parameters may also be different (turbulence, pulsatility, etc.). In addition, the flow characteristics of blood within a smaller branch of the blood vessel will be different than the flow characteristics in a larger vessel. For example, blood flow within a vein branch may completely or substantially stop where a catheter tip is totally or partially occluding the vein branch. In the case where the catheter tip is seated against a vessel wall, flow patterns around the catheter are different than when the catheter tip is in free flowing blood.

In the situation where the catheter tip passes into the superior vena cava, and passes near or into the heart's right atrium or right ventricle, the flow characteristics of the blood will change. For example, the blood flow may become more or less turbulent. More or less turbulence results in different flow characteristics, profiles, and flow types and can be detected by a variety of types of sensors.

These flow profile changes can be measured using devices and methods disclosed herein.

Devices disclosed herein may include a catheter, a guidewire, a stylet, a controller, communications, an infusion mechanism, a medium source, medium sensor or sensors etc.

Devices and methods disclosed herein utilize the introduction of a medium or injectate (saline, fluid, light, sound, etc.) which has a measurable parameter (temperature, conductivity, impedance, opacity, light reflectivity, sound reflectivity, density, viscosity, ability to absorb light, ability to absorb sound, amplitude, etc.) where the measurable parameter can be detected using a sensor (sensor, thermocouple, electrode, light sensor, sound sensor, microphone, etc.). By introducing a medium at or near the tip of the catheter, and measuring one or more parameters of the medium over time, and possibly over distance, flow parameters, such as flow direction, rate, volume and type, turbulent or laminar, can be determined. Based on these determinations, the user can identify whether the catheter tip is progressing to the desired position in the vasculature via the desired path. Vessels may be identified by type (vein vs. artery, vs heart etc.), size, shape, etc.

The measurable parameter of the injectate medium is different from that of blood, either higher or lower. In some embodiments, the measurable parameter of the injectate medium or of blood may be zero or essentially zero. For example, where the parameter is conductivity, the injectate medium may be a zero conductivity fluid, such as distilled water or similar.

The medium may be injected or introduced in boluses or drips, periodically during all or part of catheter placement, continually during all or part of catheter placement, or at regular intervals during all or part of catheter placement. The medium may be introduced manually, or automatically via a controller, or automatically via an intravenous (IV) bag with or without an IV pump, or passively with an IV.

Measurements of one or more medium parameters may be taken before, during and/or after medium introduction. For example, room temperature or other non-body temperature saline (or other fluid) may be injected through the catheter or stylet during placement. One or more sensors at or near the distal tip of the catheter/stylet can measure the temperature of the fluid immediately surrounding the sensor(s) over time as the device is advanced/moved. Based on blood flow characteristics, including direction, pulsatility and turbulence, the temperature profile over time will be different at different locations, resulting in a temperature (or parameter) profile or signature for different flow types and therefore different catheter/stylet tip location scenarios.

In embodiments where the device is used in fluid flow, for example in a blood vessel, the medium may be a fluid (first fluid) which has a measurable parameter that is different than that of the fluid within the vessel (second fluid, which may be blood). The sensors in any of the embodiments disclosed herein may be measuring the parameter of the mixture of the first fluid and the second fluid, over time and at different locations, to determine the location of the device. Note that in some embodiments, the medium parameter level may be negligible and may serve to dilute the parameter in the mixture of the first fluid and the second fluid. For example, where the parameter is electrical conductivity, the medium, or injectate, may be distilled water, or another injectate, which has negligible conductivity, where blood has a higher conductivity. In these embodiments, the sensors may be measuring the conductivity of the injected medium/blood mixture to determine device location.

Temperature sensors may include thermocouples or other temperature sensors, such as, fiber optic, resistive, bimetallic, thermometer, state-change, silicon diode, thermistors, optical temperature measurement (infrared or otherwise), mercury thermometers, manometers, etc. The sensor or sensors is/are in communication with a controller which records and/or analyzes the signal from the sensor(s). The communication between the sensor and the controller may be wired or wireless.

By placing a thermocouple, thermistor, or other temperature sensing device, or an array of temperature sensing devices on or through the catheter, one can determine the direction of flow of a room temperature fluid bolus that is injected into the blood stream. Since blood temperature is around 37 degrees C., a saline (or other) fluid bolus or fluid infusion with a temperature around 20-25 degrees C. or between 15 and 30 degrees C. or between 0 and 35 degrees C., or generally cooler than 37 degrees C. is distinguishable from body temperature and can be used to detect blood flow direction and characteristics, and therefore, device location.

Alternatively the fluid may be greater than body temperature, optimally about 40 C but ranging from about 39 C to 42 C or about 37 C to about 45 C.

In some embodiments, optical sensing can be used. Optical sensors can be used to detect the direction of flow by measuring the amount of dilution of blood with another fluid with different optical characteristics, such as saline.

Sonar or sound can alternatively be used as the parameter to detect blood flow direction, velocity and other blood flow characteristics. Sound waves may be produced by the controller and conveyed to the tip, or near the tip, of the catheter. A sound detector, or microphone, records the sound waves reflected back by the red blood cells or other components of blood. Saline may also be introduced to create a change in the sound waves detected.

Various mediums and/or parameters may be used in combination in some embodiments. For example, light (visible and/or not visible) and temperature may both be used. In addition, other sensors may be used to aid in locating the catheter, including electro cardiogram (ECG), ultrasound, Doppler, x-ray, etc. Pressure may also be used instead of, or in combination with these embodiments.

Embodiments that incorporate more than one type of sensor may be used either in each situation (vein vs. artery, vessel branch, vessel wall, catheter in heart or past heart), or different sensors may be used in different situations. For example, pressure may be used to determine when the catheter tip is in the heart, where temperature may be used to determine whether the catheter is in an artery. Or, for example, ECG can be used to determine if the catheter is in the cavo-atrial junction but temperature can be used to determine if the catheter has gone down an azygous or unintended vein branch.

In some embodiments, a camera may be used to optically determine the presence, and possibly the density, or number, of red blood cells. If a greater number of cells pass by, then the flow is stronger. If they are flowing in the opposite direction, then the flow has reversed direction, thus the catheter is proceeding in the incorrect direction.

These sensing modalities can also be combined with one or more (ECG) sensors to detect catheter placement. ECG electrodes can be placed precisely either at the target location of the catheter tip (for example, in the superior ⅓ of the vena cava), or over the heart itself to detect an unnecessary over extension of the catheter. Alternatively, one or more ECG sensors may be incorporated into the device itself, for example, into a guidewire/stylet. Alternatively, ECG signals can be gathered with the same sensors or electrodes that are used to measure conductivity, temperature or other parameters. The received signal may alternate between ECG and conductivity for example, with or without breaks in between.

In any of the embodiments disclosed herein, the sensors may be located at or near the distal tip of, or along the length of a guidewire or stylet that passes through a vascular catheter.

One objective of some of the embodiments disclosed herein is to locate the device within the vasculature without the use of x-ray and/or fluoroscopy, and/or ultrasound and/or magnetic fields, and/or other imaging modalities.

Some embodiments disclosed herein may be specifically designed to be used with a sitting patient, or a patient with a pacemaker, or patients with specific conditions, etc.

One embodiment of a location detection system may generally comprise an elongate body defining a lumen at least partially along a length of the elongate body. One or more sensors may be positioned near or at a distal tip of the elongate body and one or more openings may be defined along the elongate body in proximity to the one or more sensors, wherein the one or more openings are configured to control a boundary distance between the one or more sensors and a fluid with a parameter of a known initial value when emitted from the one or more openings. A controller may be in communication with the one or more sensors, wherein the controller is configured to track a change in the parameter relating to concentration over the one or more sensors and determine a position of the one or more sensors within a body of a subject.

Another embodiment of a location detection system may also generally comprise an elongate body defining a lumen at least partially along a length of the elongate body. One or more sensors may be positioned near or at a distal tip of the elongate body and one or more openings may be defined along the elongate body in proximity to the one or more sensors, wherein the one or more openings are sized to control a boundary distance between the one or more sensors and a fluid with a parameter of a known initial value when the fluid is emitted at a predetermined flow rate. A controller may be in communication with the one or more sensors, wherein the controller is configured to track a change in the parameter relating to concentration over the one or more sensors and determine a position of the one or more sensors within a body of a subject.

In one example of a method of determining a location within a body of a subject, the method may generally comprise emitting a fluid with a parameter of a known initial value through one or more openings defined along an elongate body and sensing a change in the parameter of the fluid relating to concentration via one or more sensors positioned near or at a distal tip of the elongate body and in proximity to the one or more openings, wherein the one or more openings are configured to control a boundary distance between the one or more sensors and the fluid having the parameter when emitted from the one or more openings. A position of the one or more sensors within the body of the subject may be determined based upon the dilution of the fluid.

BRIEF DESCRIPTION OF THE DRAWINGS

FIG. 3 shows an embodiment of the vascular catheter navigation device.

FIGS. 4A-F show the influence of fluid flow direction on flow behavior of an injected fluid bolus with respect to the catheter tip before, during and after injection.

FIG. 8 is a schematic illustration showing fluid flow in different areas of the vascular system.

FIGS. 9A-9E show various embodiments of the vascular catheter navigation device.

FIGS. 10A-E show an embodiment of the vascular catheter navigation device which can be used with any catheter.

FIGS. 11A-I show various views of various embodiments of a stylet/guidewire version of the vascular catheter navigation device.

FIGS. 18A and B show 2 possible embodiments for a flow director.

FIGS. 19A-C show other embodiments of the vascular catheter navigation device injectate lumens.

FIGS. 23A-E and 24A-E show possible graphical user interfaces of the device.

FIGS. 25A-C show embodiments of the vascular catheter navigation device which include a conduit to control fluid flow exiting from the device.

FIGS. 36A-C show an embodiment of the vascular catheter navigation device which includes a compressible conduit.

FIGS. 37A-F show 2 different cross-sectional views of various embodiments of the vascular catheter navigation device.

FIGS. 38A-E show various embodiments of the vascular catheter navigation device.

FIGS. 39A-D are longitudinal cross sectional views of embodiments of the vascular catheter navigation device.

FIGS. 39E-G are radial cross sectional views of embodiments of the vascular catheter navigation device.

FIGS. 39H-J are cross sectional views of embodiments of the vascular catheter navigation device with securing type conduits.

FIG. 39K shows an embodiment of the vascular catheter navigation device with the conduit running the length, or essentially the entire length, of the catheter.

FIGS. 40A-C show different configurations of vascular catheter lumens and variations of embodiments of the vascular catheter navigation device which work with them.

FIGS. 42A-C show an embodiment of the vascular catheter navigation device.

FIGS. 61A-E show some examples of diffuse exit port designs.

FIG. 86 shows an embodiment of the vascular navigation device which uses electrodes as sensors.

FIG. 87 shows an embodiment of the vascular navigation device where the stiffener exits beyond the end plug.

FIG. 88 shows an embodiment of the vascular navigation device where the stiffener ends in a curved portion.

FIG. 91 shows an embodiment of the vascular navigation device with a double later exit port area.

FIG. 92 shows an embodiment of the vascular navigation device where the core, or stiffener, includes the leads for the sensors/electrodes.

FIG. 93 shows an embodiment of the vascular navigation device where the stiffener is exposed at the distal end forming the distal most electrode.

FIGS. 95 and 96 show the relative magnitude of the signal from the distal and proximal sensors, as well as signal pulsatility.

FIG. 97 shows that signal magnitude, relative signal magnitude, and/or signal pulsatility can be used by the controller of the vascular navigation system to determine the location of the distal end of the device.

DETAILED DESCRIPTION OF THE INVENTION

Figure 1:
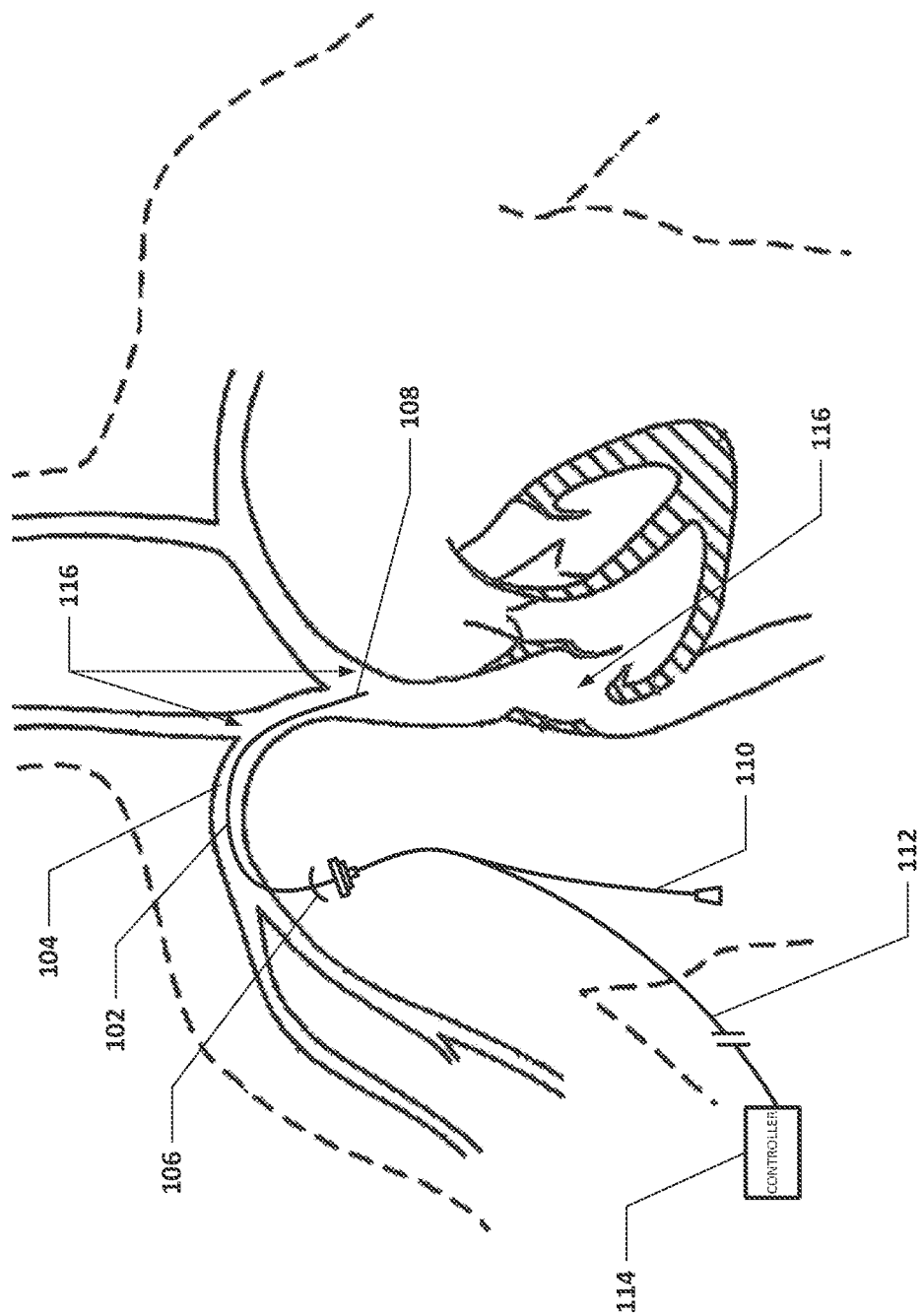
FIG. 1 shows an embodiment of the vascular catheter navigation device navigating the human anatomy.

FIG. 1 shows an embodiment of the vascular catheter navigation device or system navigating the human anatomy. Vascular catheter navigation device 102 is shown in vein 104 of a patient. The vascular catheter navigation device has been inserted into the patient via insertion point 106. The insertion point is shown here in the patient's chest, however the insertion point may alternatively be the patients leg, arm or neck or other location. To navigate a standard vascular catheter into its desired location, several undesirable obstacles need to be avoided and/or overcome. For example, a vascular catheter may be mistakenly placed into an artery instead of a vein, a vascular catheter may venture down or up an incorrect branch of the vascular system, a vascular catheter may become lodged against a wall of a blood vessel, a vascular catheter may be advanced too far, either too close to the heart, into the heart or past the heart, or a vascular catheter may not be advanced far enough to reach its desired location, or may migrate to a less desirable location. A few of these hazard areas are labeled 116. Distal tip of vascular catheter navigation device is shown as 108. At the proximal end of vascular catheter navigation device, infusion or sampling lumen 110 is shown which is in fluid communication with opening or openings at or near the distal end of vascular catheter navigation device. Also shown is sensing port 112 which is in communication with controller 114. Sensing port 112 is in communication with one or more sensors (not shown here) at or near distal tip 108 of vascular catheter navigation device 102. Although one infusion/sampling lumen and one sensing port are shown here, multiple infusion/sampling and/or sensing ports may exist. Infusion lumen 110 may also be in communication with controller 114.

Figure 2:
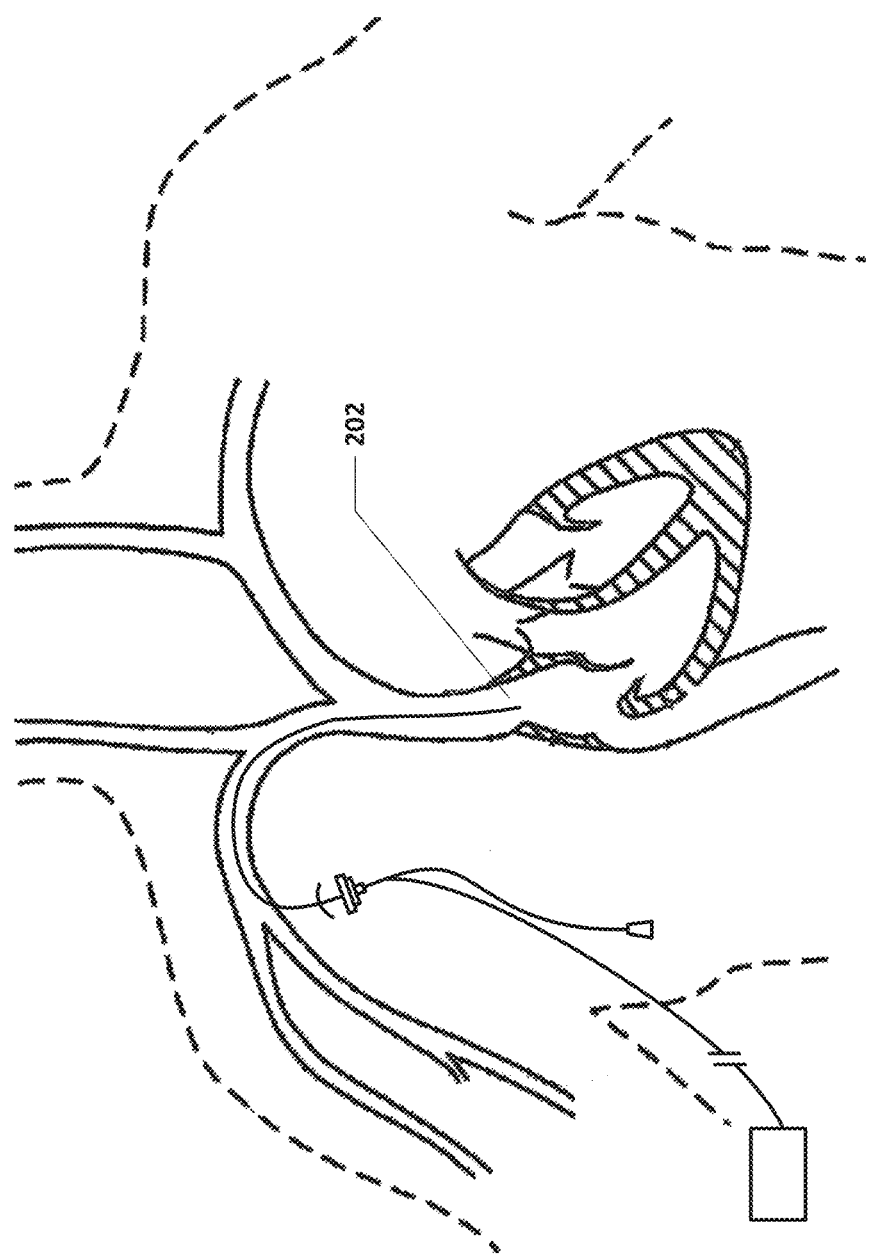
FIG. 2 shows an embodiment of the vascular catheter navigation device placed in the human anatomy.

FIG. 2 shows an embodiment of the vascular catheter navigation device where the distal tip is placed in the superior vena cava/cavo-atrial junction (SVC-CAJ) 202.

FIG. 3 shows an embodiment of the vascular catheter navigation device. The distal end of the vascular catheter navigation device is inserted into the appropriate access vein, and advanced along the vein to its target location. After the vascular catheter navigation device is inserted into the blood vessel, generally through a needle, catheter or sheath, sensing element 302 senses a parameter within the blood flowing through a blood vessel. A medium, such as fluid, with a measurable parameter, such as temperature, or conductivity, is injected through the device, and into the blood vessel. The sensor signals are communicated back to the controller where the sensor signal(s) are analyzed based on the sensor data over time, including data curve slope, magnitude, value, length, variability, pulsatility, phase, standard deviation, shape, pulsatility/fourier analysis etc. For example, the controller can determine whether the distal end of the vascular catheter navigation device is in an artery instead of a vein, based on magnitude and direction of blood flow around the vascular catheter navigation device by measuring and analyzing the measurable parameter. If the controller determines that the distal end of the vascular catheter navigation device is in an undesired position, an alert or other indicator may communicate with the user. For example, if the controller determines that the catheter is in an artery instead of a vein, a specific identifying signal may sound, including an audible, visual signal etc., instructing the user to retract the vascular catheter navigation device, and any other device, such as sheaths, catheters etc., and apply pressure to the blood vessel.

Similarly, the vascular catheter navigation device can sense when the distal end is in the incorrect branch of a vein, based on flow direction, and possibly flow profile and magnitude. When advancing the vascular catheter navigation device in the correct direction and in the correct vessel (toward the SVC-CAJ, in a vein), the blood flows over the vascular catheter navigation device from the more proximal end toward the distal end.

FIG. 3 shows one sensor 302, one sensor port 112 and one infusion/sampling lumen 110. However, more than one infusion/sampling lumen and/or more than one sensors may be present. In addition the port to the controller and the sampling lumen could be the same lumen and be incorporated into a single lumen device. The infusion and/or sampling lumen may also be connected to the controller.

FIGS. 4A-F shows the influence of fluid flow direction on flow behavior with respect to the catheter tip before, during and after an injected fluid bolus. At time=0, device 102 is in vessel 404. Device 102 includes sensor 302. Sensor 302 is designed to measure a parameter of blood and/or the injection medium. The controller (not shown) is in communication with sensor 302 via connector 402 which, in this example, runs the length of the catheter back to the controller. Sensor 302 and connector or lead 402 may be incorporated into the vascular catheter or may be incorporated into a stylet that runs through the catheter. Medium 410 is introduced into the vessel at time=x. For example, the medium may be saline at a temperature which is different than that of the body. The parameter measured by the sensor in this example would be temperature, but could be any parameter, such as conductivity. After the injection, at T=x+1, blood flow will mix the medium with the blood flow. FIGS. 4A-C show the device in in-line blood flow. Where blood flow 406 flows away from the catheter, the bolus of medium 404 travels away from the catheter tip and away from the sensor. FIGS. 4D-F show the device in counter blood flow, such as in an artery. Where blood flow 408 flows toward the catheter, the bolus of medium 410 travels toward and over the catheter tip. This example shows a bolus of fluid, but a stream of fluid may also be used.

Depending on the location of the sensor(s), different temperature, or parameter, profiles may be measured over time/location. Variables in flow rate, direction, turbulence, etc. will affect the mixing of blood and medium and affect the profile of the parameter, in this example, temperature, over time. In this way, the system can determine blood flow direction and characteristics at or near the catheter tip.

Figure 5A:
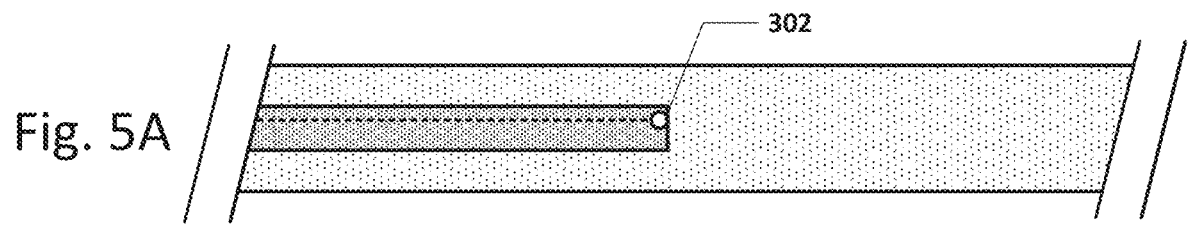
FIGS. 5A-5E show a variety of embodiments of the vascular catheter navigation device.
Figure 5B:
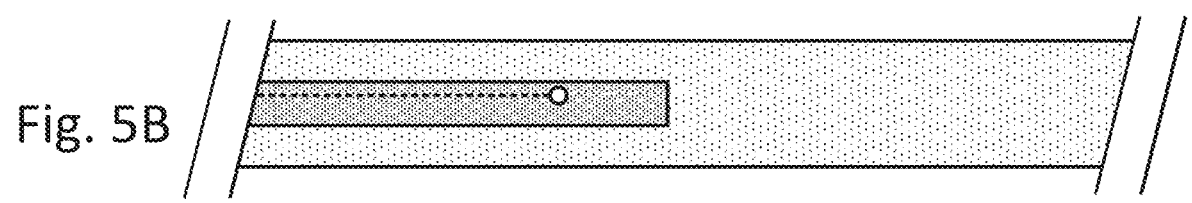
Figure 5C:
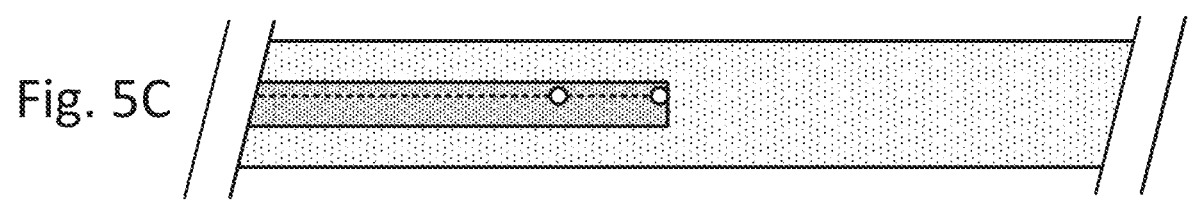
Figure 5D:
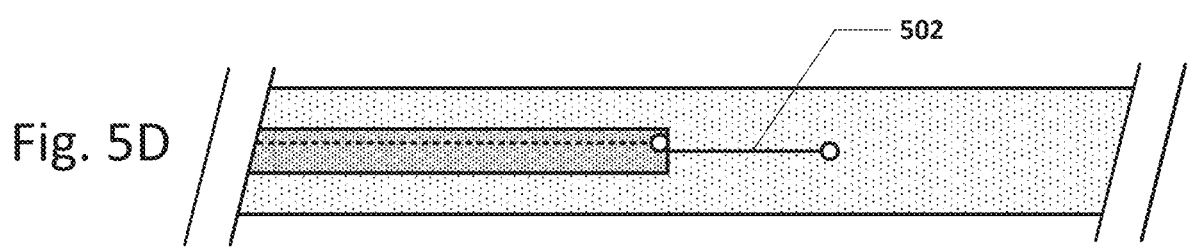
Figure 5E:
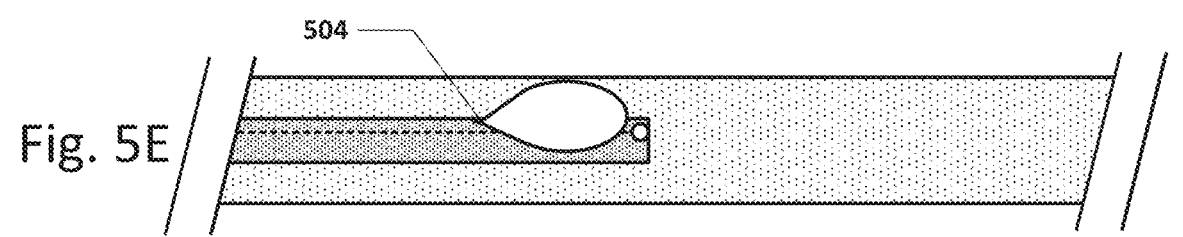

FIGS. 5A-5E and 6A-6E show several example embodiments of the vascular catheter navigation device. FIG. 5A shows an embodiment with sensor 302 at the catheter tip. FIG. 5B shows an embodiment with the sensor near, but not at, the catheter tip. This configuration may prevent the sensor from measuring the parameter during introduction of the medium from the catheter tip, allowing better distinction between flow directions. FIG. 5C shows an embodiment with 2 sensors, one at the catheter tip, and one near, but not at, the catheter tip. Sensor readings at different positions will vary based on fluid flow direction, characteristics, profile etc. A sensor near, but not at, the catheter tip may be from about 0.05 cm to about 2.0 cm back from the tip. Alternatively, a sensor near, but not at, the catheter tip may be from about 0.75 cm to about 1.25 cm back from the tip. FIG. 5D shows an embodiment where a sensor is on guidewire or stylet 502. Stylet 502 may move freely within the catheter allowing one or more sensors to be placed at a distance from the catheter tip. In addition, the guidewire/stylet may be removed after catheter placement. In this embodiment, the catheter may also include a sensor, as shown here. FIG. 5E shows an embodiment with opening 504 which is near, but not at, the catheter tip. This opening may be in fluid communication with a separate medium introduction lumen or infusion lumen, or the same lumen as that of the distal opening. This specific medium introduction lumen may exit at the catheter tip. An opening near, but not at, the catheter tip may be from about 0.25 cm to about 2.0 cm back from the tip. Alternatively, an opening near, but not at, the catheter tip may be from about 0.75 cm to about 1.25 cm back from the tip. The medium introduction lumen may be in the catheter or may be within the stylet. More than one injectate medium may be introduced either through the same lumen or through separate lumens of the device.

Figure 6A:
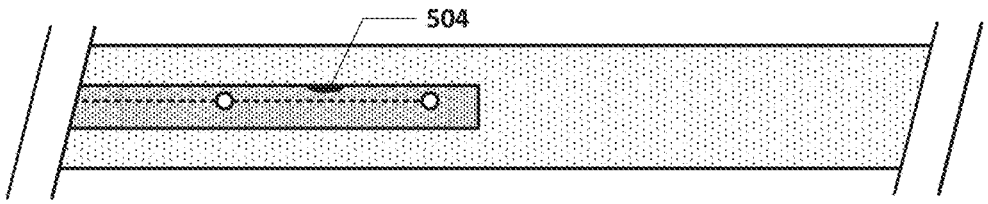
FIGS. 6A-6E show a variety of embodiments of the vascular catheter navigation device.
Figure 6B:
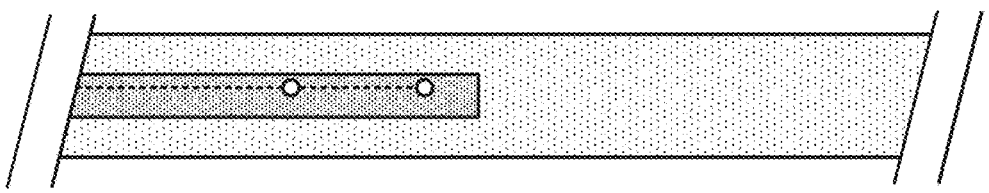
Figure 6C:
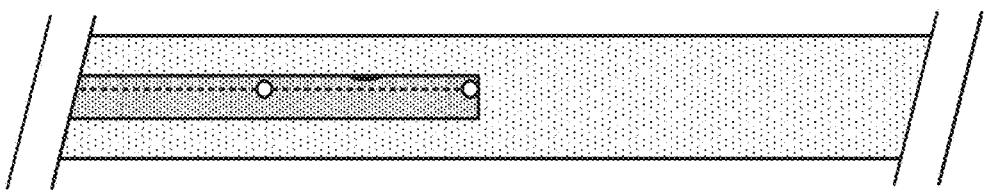
Figure 6D:
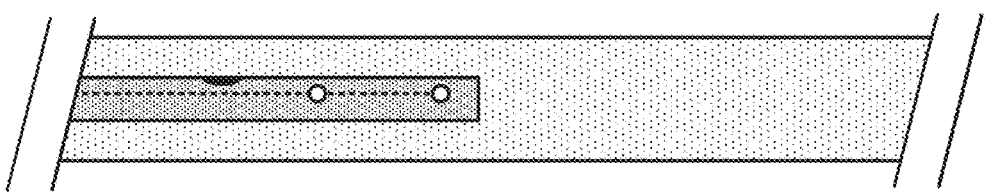
Figure 6E:
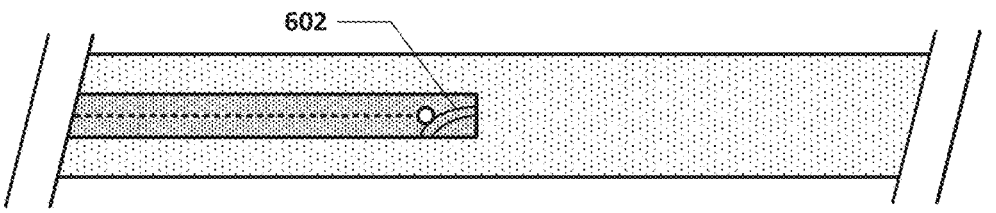

FIG. 6A shows an embodiment with an opening between two sensors, both of which are near, but not at, the catheter tip. FIG. 6B shows an embodiment with more than one sensor near, but not at, the tip of the catheter. FIG. 6C shows an embodiment with an opening between two sensors, one of which is at the catheter tip. FIG. 6D shows an embodiment which includes an opening proximal to 2 sensors. FIG.

6E shows an embodiment with channel 602. Channel 602 allows fluid to flow within the catheter, in proximity to a sensor within the catheter.

Figure 7:
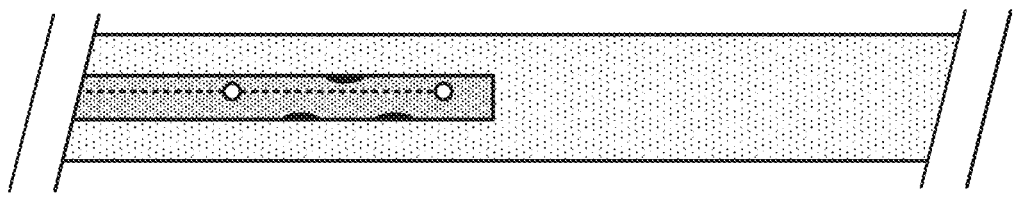
FIG. 7 shows an embodiment of the vascular navigation device with 2 sensors and multiple openings between the two sensors.

FIG. 7 shows an embodiment of the vascular navigation device with 2 sensors and multiple openings between the two sensors.

It is apparent that numerous variations of these and other embodiments of the vascular catheter navigation device are envisioned. For example, sensors, openings, channels etc. may be on different sides of the catheter and/or guidewire/stylet. Sensors, openings and channels are shown here at or near the catheter tip, however, they may be located anywhere along the catheter and/or guidewire/stylet.

Different sensor configurations will result in different parameter curve signatures in different vascular locations. For example, a single sensor will give a different set of curves than will a system with 2 sensors. The distance of the sensor(s) from the infusion exit site will also provide different curves. Different infusion rates, infusion volumes, infusion types (bolus vs. stream), infusion pressures, infusion velocities etc., will also provide different curves and thus different anatomical signatures. Different aspects of the curves may be analyzed by the controller to determine vascular location. These may include, but are not limited to, slope, magnitude, value, length, variability, pulsatility, phase, standard deviation, shape, area under the curve, Fourier transform, frequencies, harmonics, etc. In some embodiments, certain frequencies in the data may be filtered out, including those relating to the heartbeat, system noise, tissue conductance, etc.

In some embodiments there is one sensor and therefore one parameter vs. time/location curve. In some embodiments there are two or more sensors and therefore two or more parameter vs. time/location curves. In some embodiments, the infusion exit port is near the more proximal sensor or sensors. In some embodiments the infusion exit port is proximal or distal to the sensor or sensors. In some embodiments the infusion exit port is between the sensors. In some embodiments, one or more than two sensors may be used.

Note that parameter curves may appear different, in different anatomy, and based on the design of the vascular catheter navigation device. For example, the curve may be different for different sensor locations with respect to the fluid exit port. The curve may depend on the type of sensor or the fluid injection rate. The curve may depend on the initial parameter level of the injection fluid. Other design factors may also result in different parameter vs. time/location curve shapes.

In addition, calibration of the sensor vs. time/location curves may be performed by the controller. For example, a baseline measurement may be derived after insertion of the system, or at other points during use of the system. For example, a baseline measurement may be taken in the blood vessel before any injection fluid is injected, or at a particular injection rate. A baseline measurement (a measurement taken without any fluid injection into the system) may be used in the controller's analysis of the data to determine the location of the vascular catheter navigation device within the anatomy.

Various properties of the parameter vs. time curves may be analyzed to determine the location of the vascular catheter navigation device. For example, curve amplitude, noise, standard deviation, shape, slope, value, area under the curve, Fourier transform, frequencies, harmonics, etc. of one or more curves may be used to determine the vascular catheter navigation device location within the vasculature. These same parameters may be compared between and among multiple parameter vs. time/location curves to determine vascular catheter navigation device placement location. For example, the location, relative location, magnitude, and/or relative magnitude of peaks (positive or negative) of the curves may be used to determine vascular catheter navigation device location. In addition, the difference between amplitude, noise, standard deviation, shape, slope, value, area under the curve, and/or Fourier transform, harmonics, frequencies of the data from the multiple sensors may be used to determine vascular location. Depending on droplet size and/or infusion rate, an area under the curve, or Fourier transform may be used to analyze the parameter vs. time curve and thus vascular location. Additionally, a maximum, or a number of maxima, may be relevant.

The term "droplet" used herein may mean a drop, a bolus, a stream, an intermittent stream, etc. when referring to the injectate.

FIG. 8 is a schematic showing fluid flow in different areas of the vascular system representing desired (correct) and undesired (incorrect) device placement. Arrows 802 show blood flow direction. Areas 804 show fluid (such as saline) infusion. Note how the different anatomical locations will yield different flow conditions and thus different dissipation patterns of the fluid infusion. Although 1 sensor 806 is shown here, two, or three, or four or five or six or more may be used, in this, and any other embodiments disclosed herein.

Note that several embodiments disclosed herein may mention a particular type of sensor and measured parameter, such as a sensor measuring temperature. However, any of the embodiments disclosed herein may use any type of sensor (or more than one type of sensor) which measures that sensor's parameter. For example, embodiments that disclose sensors measuring temperature, may alternatively, or additionally include conductivity sensors measuring conductivity. Embodiments which mention the controller using data from a particular type of sensor, may alternatively or additionally use data from another type of sensor.

FIGS. 9A-9E show various embodiments of the vascular catheter navigation device where two sensors, or other types of sensors are on the guidewire/stylet. FIG. 9A shows stylet 910 with proximal sensor 902 and distal sensor 904. The injectate 906 in this embodiment exits at the distal tip of catheter 908, proximal, or near to proximal sensor 902. Alternatively, the injectate may be injected through a lumen of the guidewire/stylet. Although 2 sensors are shown here, one, or more than 2 may be used.

FIG. 9B shows an embodiment where the injectate is injected through the stylet/guidewire and exits between the two sensors. FIG. 9C shows an embodiment where the injectate is injected through the stylet/guidewire and exits near or distal to the distal sensor. If one sensor is used, the fluid injection exit port may be either proximal to, or distal to the sensor.

FIGS. 9D and 9E show an embodiment with two sensors on the stylet/guidewire where the guidewire is able to be moved with respect to the end of the catheter. This embodiment may be used to alter the sensing and/or injectate exit location with respect to the tip of the catheter.

For example, in some embodiments, the stylet/guidewire may include both the injection lumen (i.e. the stylet/guidewire may be hollow) and a sensor so that it may be positioned in the anatomy first and/or independently of the vascular catheter. For example when jugular access is being used for catheterization. Once the stylet/guidewire is placed, the vascular catheter may be advanced so that the distal tip of the catheter is at a known position relative to the distal tip of the stylet/guidewire. The stylet/guidewire may then be removed.

Figure 9F:
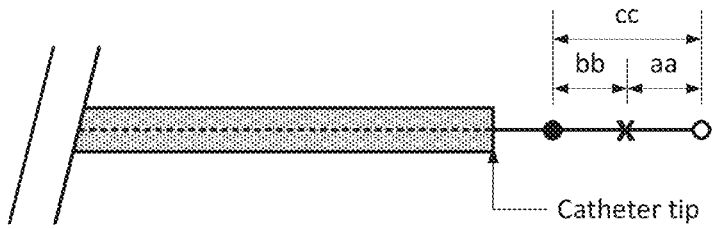
FIGS. 9F-9J show distances between the fluid ports and the sensors.
Figure 9G:
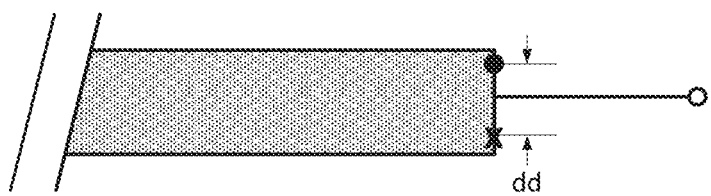
Figure 9H:
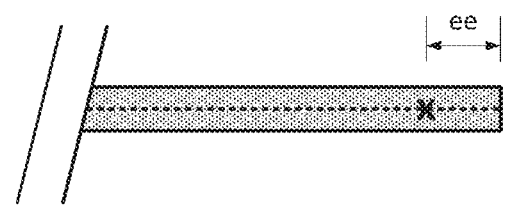

FIGS. 9F through 9H show distances between the fluid exit port and the sensor(s) and distances between the catheter/stylet tip and the sensor(s)/ports. FIG. 9F shows the axial distance aa between the injectate exit or port, and the distal or singular sensor. The axial distance bb is the distance between the fluid exit port and the proximal sensor. The axial distance cc is the distance between the distal sensor and the proximal sensor. These distances may be positive or negative. Although 2 sensors are shown here, the device may have one sensor or more than 2 sensors.

Distance aa may be about 0 mm. Alternatively, distance aa may be a range of about 0 mm to about 0.5 mm, or about 0 mm to about 1 mm. Alternatively, distance aa may be a range of about 0 mm to about 2 mm. Alternatively, distance aa may be a range of about 0 mm to about 3 mm. Alternatively, distance aa may about 3 mm to about 5 mm. Alternatively, distance aa may about 5 mm to about 10 mm. Alternatively, distance aa may be a range of about 0 mm to about 100 mm. These distances may alternatively be negative. For example, distance aa may be about 1 mm or may be about −1 mm. In the case of 1 mm, the distal sensor will be distal to the fluid exit port. In the case of −1 mm, the fluid exit port will be distal to the distal sensor. This is true for all dimensions provided in association with FIG. 9F-9H.

Distance bb may be about 10 mm. Alternatively, distance bb may be a range of about 0 mm to about 10 mm. Alternatively, distance bb may be a range of about 8 mm to about 12 mm. Alternatively, distance bb may be a range of about 5 mm to about 15 mm. Alternatively, distance bb may be a range of about 1 mm to about 100 mm. Alternatively, distance bb may about 3 mm to about 5 mm. Alternatively, distance bb may about 5 mm to about 10 mm. Alternatively, distance bb may be a range of about 0 mm to about 100 mm. These ranges may also be negative distances.

Distance cc may be about 10 mm. Alternatively, distance cc may be a range of about 0.0 mm to about 5 mm. Alternatively, distance cc may be a range of about 5 mm to about 15 mm. Alternatively, distance cc may be a range of about 15 mm to about 20 mm. Alternatively, distance cc may be a range of about 1 mm to about 100 mm.

Distance dd in FIG. 9G is the distance between the fluid exit port and either the distal or proximal sensor. The distance is shown with respect to the proximal sensor here, but distance dd may apply to either. Alternatively, only one sensor may be present. Distance dd may be about 0.75 mm. Alternatively, distance dd may range from about 0.25 mm and 1.5 mm. Alternatively, distance dd may range from about 0.1 mm and 5 mm.

FIG. 9H shows the axial distance ee between the fluid exit port and the end of the catheter and/or stylet. Distance ee may be about 0 mm. Alternatively, distance ee may range from about 0 mm and about 1 mm. Alternatively, distance ee may range from about 0 mm and about 3 mm. Alternatively, distance ee may range from about 0 mm and about 5 mm. Alternatively, distance ee may range from about 5 mm and about 10 mm. Alternatively, distance ee may range from about 0 mm and about 100 mm. These distances may be positive or negative.

Figure 9I:
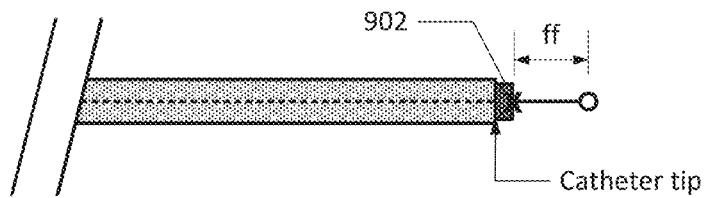

FIG. 9I shows an embodiment of the vascular catheter navigation device which includes only one sensor and includes conduit 902 in the system. Various embodiments of the system including a conduit will be described in more detail elsewhere herein. Conduit 902 incorporates the injectate exit port shown by an X. Distance ff shown here is the longitudinal distance between the fluid injectate exit port of the conduit and the sensor.

Figure 9J:
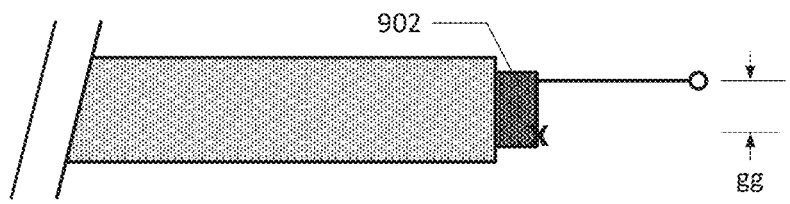

FIG. 9J shows an embodiment similar to that in FIG. 9I where the distance gg represents the radial distance between the fluid injectate exit port of the conduit and the sensor.

FIGS. 10A-E show an embodiment of the vascular catheter navigation device which can be used with any catheter, or in other words, where the sensor(s), the injectate lumen, the controller, and locking mechanism are included with the stylet/guidewire. FIGS. 10A-E show an embodiment with two sensors, distal sensor 1012 and proximal sensor 1010, and injectate exit port 1002 as part of guidewire/stylet 1001. Alternatively, the stylet/guidewire may only have one sensor, or may have more than two sensors. The stylet/guidewire may include features 1014 to help align the stylet/guidewire and the catheter. This embodiment may include a tip portion 1006, such as a molded urethane, nylon, silicone, or other polymer portion, for embedding the sensor (s). Also shown here is an optional guidewire/stylet coil 1008 and the distal tip of catheter 1018. In the cross sectional view, injection lumen 1016 can also be seen.

This embodiment may include torque or locking device 1022 which may be used to lock the stylet to the proximal end of the catheter, for example using luer lock 1020 at the proximal end of catheter 1018. The torque/locking device may be locked to the stylet/guidewire so that the stylet/guidewire won't move with respect to the vascular catheter. Controller (not shown) may include and/or control an infusion mechanism via fluid port 1026 as well as read data from the sensor(s) via sensor port 1004. The controller may be located near the proximal end of the stylet, or may be located several inches or feet from the proximal end of the stylet. sensor leads 1024 are also shown. The infusion may be steady or intermittent or consist of boluses.

FIGS. 11A-I show various views of various embodiments of a stylet/guidewire version of the vascular catheter navigation device.

The stylets shown in 11A-11I and some other embodiments serve several functions, including: 1) Stiffening of the catheter to aid in insertion 2) providing a medium for fluid delivery and 3) providing a channel for the leads for the sensor or sensors. FIG. 11A is a cross section of the stylet such as that shown in the embodiment of FIGS. 10A-E. Two sensors are shown here, but the device may include one, or more than two sensors.

FIG. 11B shows an embodiment of a stylet which includes three components in a triple lumen, heat shrink, and/or tubing housing 1102 which contains two sensors 1104 and fluid lumen 1016. Alternatively, one or more than two sensors may be present.

FIG. 11C shows an embodiment in which the stylet coil is made all, or in part, out of the sensor wires or leads. FIG. 11D is a side view of the embodiment shown in FIG. 11C.

Figure 11E:
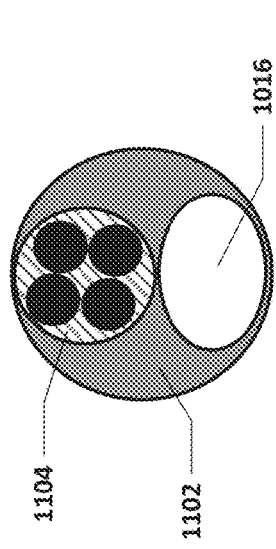

FIG. 11E shows an embodiment including an extrusion, or tube, (metal or plastic) which houses two sensors as well as a fluid lumen. Alternatively, one or more than two sensors may be present.

Figure 11F:
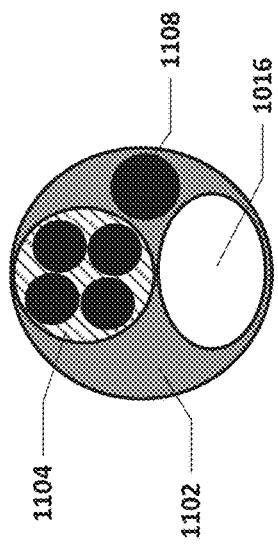

FIG. 11F shows an embodiment including an extrusion, or tube, (metal or plastic) which houses multiple sensor leads within one bundle as well as a fluid lumen.

Figure 11I:
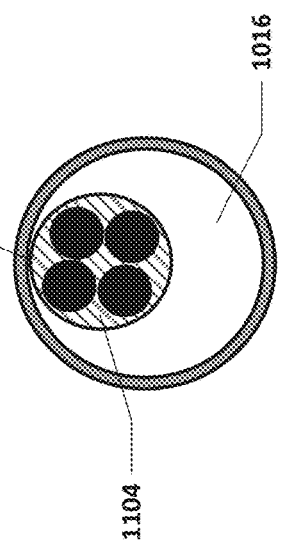
Figure 11G:
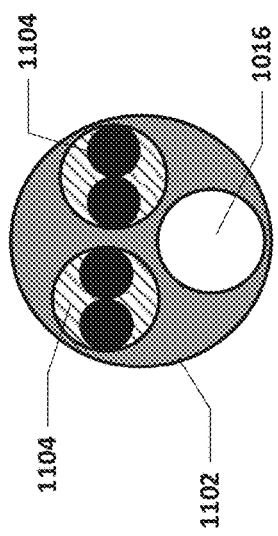

FIG. 11G shows an embodiment including a thin walled extrusion, or tube, where the sensor leads are surrounded by the fluid lumen. One, two, or more than two sensors may be present.

Figure 11H:
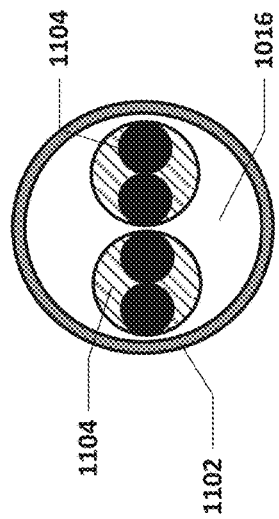

FIG. 11H shows an embodiment including an extrusion, or tube, (plastic or metal) which includes multiple sensors, a fluid lumen, as well as stiffener 1108 which may be a wire or a rod. One, two, or more than two sensors may be present.

FIG. 11I shows an embodiment including an extrusion, or tube, (plastic or metal) which includes a sensor lead bundle as well as a fluid lumen. The sensor lead bundle exterior may be made of similar material to the outer extrusion which enables optional chemical or heat formed bond or weld 1106. One, two, or more than two sensors may be present.

In some embodiments, it may be important to either fix, or precisely control, the distance between the catheter tip and the guidewire/stylet, or be able to determine the distance between the catheter tip and the guidewire/stylet. It may also be important to able to fix the location of the injection with respect to a sensor or to know the distance between the location of the injection exit port and a sensor. The distance between the exit port and the sensors will have an effect on the parameter profile during fluid infusion. These distances may be fixed across patients and scenarios, or may be different for different patient types and different scenarios. For example, the distance may be different depending on the vasculature being accessed. The distance may be different for patients of different weight, size, body mass index, health, age, sex, heart condition, or other patient characteristics. The distance may be different for different catheter sizes, catheters with different numbers and shapes of catheter lumens etc.

In some embodiments, the stylet/guidewire is fixed, or locked, with respect to the catheter tip using a torque device near the proximal end of the catheter as shown in FIGS. 10A-E.

In some embodiments, the user determines the relative alignment of the catheter and stylet/guidewire by sight and then measures the relative distance from two values.

FIGS. 12-17 show various embodiments of the vascular catheter navigation device which include various registration techniques to either fix, or know, the distance between the sensor or sensors on the stylet, and the catheter tip or fluid injection point.

Figure 12:
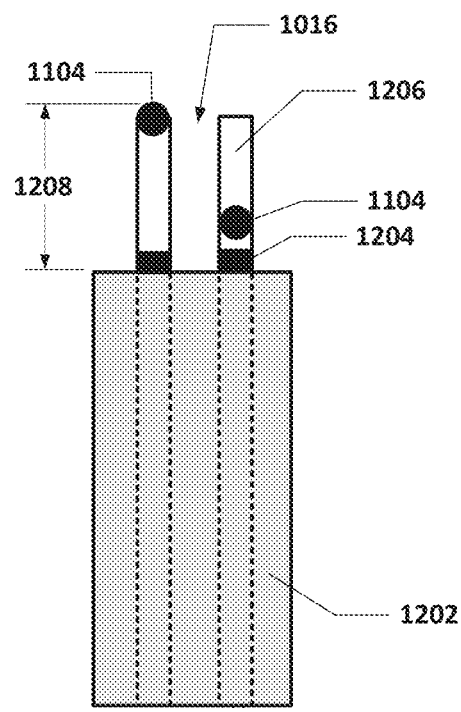
FIGS. 12-17 show various embodiments of the vascular catheter navigation device.

FIG. 12 shows an embodiment with an indicator on the stylet/guidewire which is a fixed and known distance from a sensor. In this embodiment, the user aligns the tip of catheter 1202 with indicator, or mark 1204, on stylet 1206 before insertion into the patient. The relative distance 1208 of the catheter tip to the tip of the stylet may be locked, preferably at the proximal end, using a torque device, a locking rotating hemostasis valve, a tuohy-borst valve, or other locking mechanism, before the catheter is inserted into the patient. The indicator on the guidewire/stylet may be a visible mark, such as a red stripe or dot, or a tactile mark, such as a bump or groove, or other type of indicator.

Figure 13:
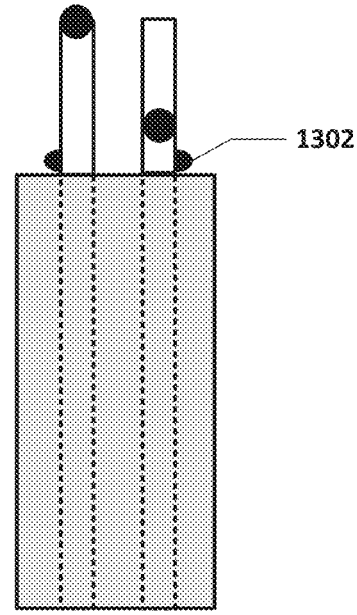

FIG. 13 shows an embodiment with raised area, or bump 1302, on the stylet which is a fixed and known distance from the distal sensor. This allows the user to align the tip of the catheter with the bump on the stylet, either visually, or by tactile feel. This alignment may be done outside the body or inside the body. In some embodiments, the bump is small or soft enough that the stylet may be removed from the catheter after placement in the anatomy.

Figure 14:
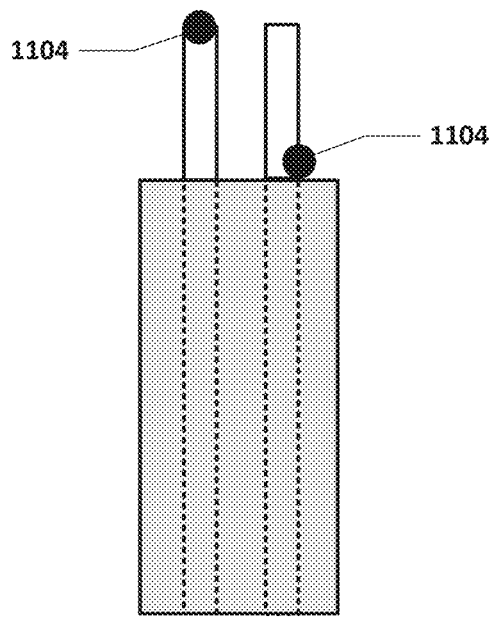

FIG. 14 shows an embodiment similar to that shown in FIG. 13 where a sensor 1104 acts as the bump on the stylet.

Figure 15:
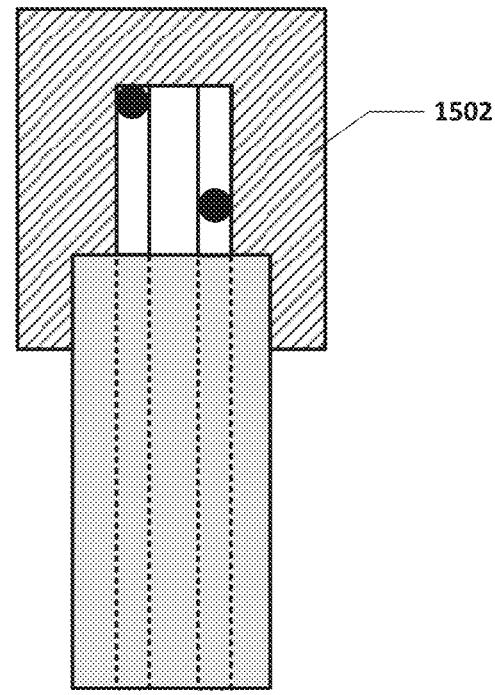

FIG. 15 shows an embodiment where jig, or block, or aligner 1502, is used to align the tip of the catheter a fixed and known distance from the tip of the stylet. The relative location of the catheter with respect to the stylet is then locked, at the proximal end, using a torque device, a locking rotating hemostasis valve, a tuohy-borst valve, or other locking mechanism, and/or at the distal end, using a securing style conduit (disclosed in detail elsewhere herein), or both. Jig or block 1502 may itself be adjustable so that it can align the fluid exit port (here the distal end of the catheter) with the sensor for a variety of different lengths.

Figure 16:
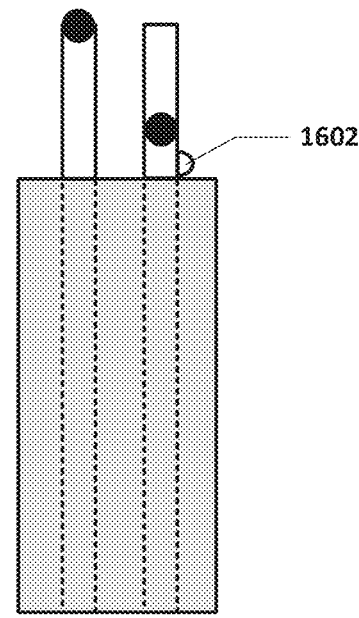

FIG. 16 shows an embodiment similar to that shown in FIG. 13 where inflatable balloon 1602 is used as the bump to align the catheter and the stylet. The balloon may be annular or on one or more sides of the stylet. The balloon may be inflated for use during alignment, and either left inflated during placement, to lock the stylet in position with respect to the catheter, or deflated during placement (where the catheter and stylet have been locked to each other using a torque or valve). In this embodiment, the stylet or catheter will include an inflation lumen to inflate and deflate the balloon. The balloon may be deflated for removal of the stylet after placement of the catheter.

Figure 17:
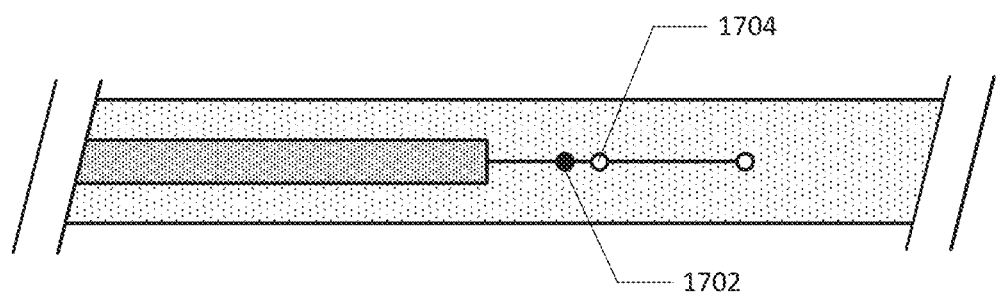

FIG. 17 shows an embodiment of the vascular catheter navigation device which includes a sensor 1702 which can sense when it is inside the catheter tip during use. For example the sensor may be magnetic, ultrasound, light, temperature, etc. In some embodiments, proximal sensor 1704 is used as a sensor to determine when the proximal sensor is inside the catheter tip. The parameter vs. time/location curve shape after injection of injectate will show a specific profile when the sensor is just inside the catheter tip, and can be used to identify this alignment. This embodiment may include one, two, or more sensors.

In some embodiments, controlling the flow patterns of the injectate exit may be important. to achieve consistent results. It may also be important to contrast the flow of the injectate with that of the blood flow within the vasculature/heart. The flow of the injectate may be purposefully made either more laminar or more turbulent to achieve these goals. Some embodiments may include features that direct the flow and are a part of the catheter or stylet. These features may be surface features, like dimpling, or an orange peel finish, that change the surface finish of the catheter or stylet. These features may be part of the OD of stylet/temp sensors or ID of fluid lumen or both.

FIGS. 18A and B show 2 possible embodiments for a flow director (to create laminar or turbulent flow) in injectate lumen 1016 of the vascular catheter navigation device. Flow director 1802 may be at the end of the injectate lumen, as shown in FIG. 18A, or it may be set back from the tip of the lumen exit, as shown in FIG. 18B.

FIGS. 19A-C show other embodiments of the vascular catheter navigation device where the shape of the injectate lumen controls the type of flow of the fluid exiting the lumen. Some of the parameters which may be varied include injectate lumen opening area, shape, surface condition, etc. sensor lead and/or stiffener 1902 is also shown.

Some embodiments may vibrate the stylet and/or catheter to create turbulent flow of the injectate from the injectate lumen.

Figure 20:
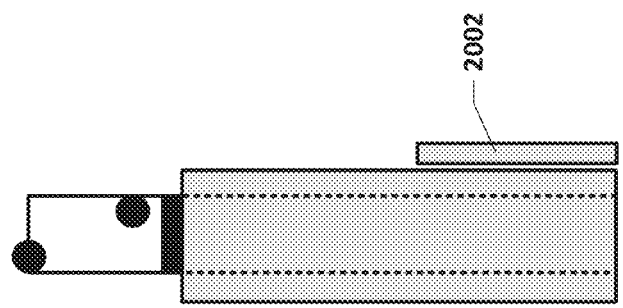
FIG. 20 shows an embodiment of the vascular catheter navigation device.
Figure 23A:
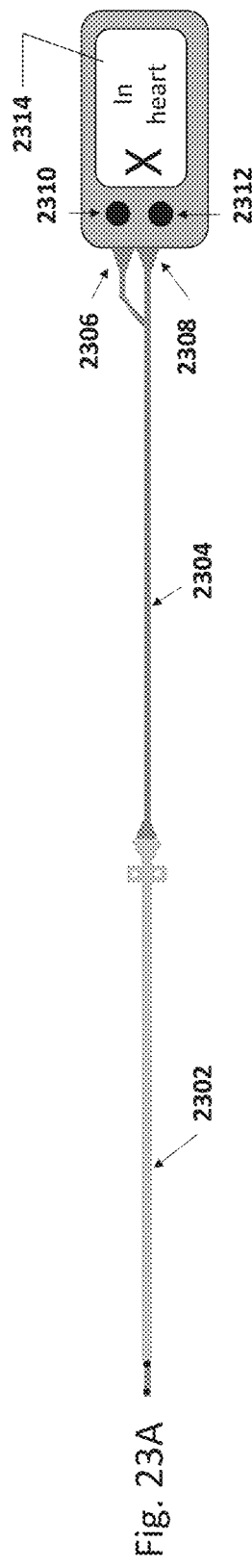
Figure 23B:
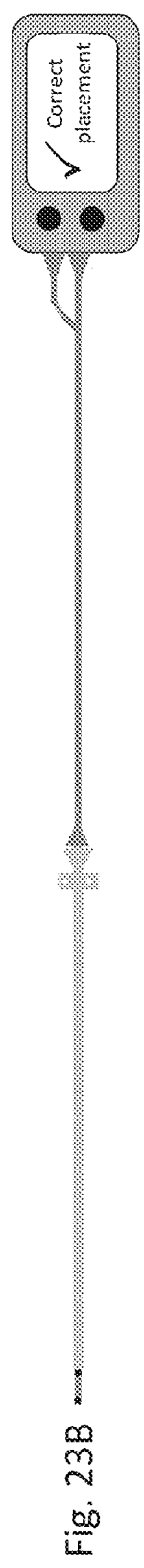
Figure 23C:
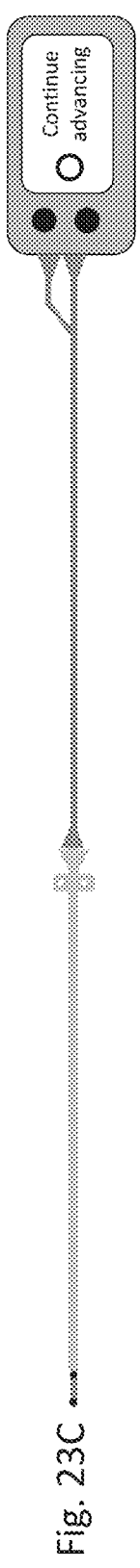
Figure 23D:
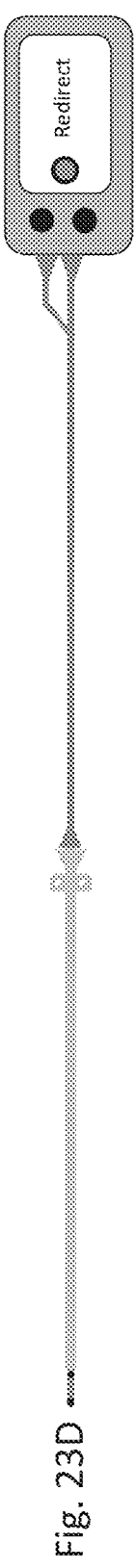
Figure 23E:
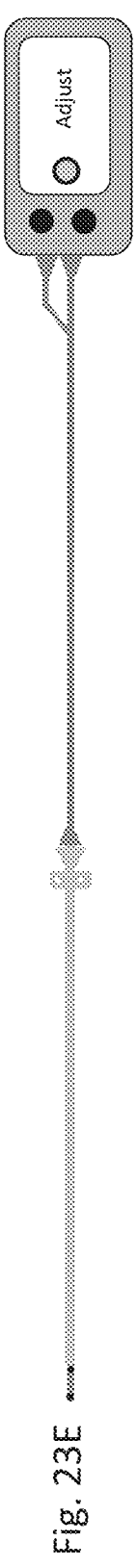
Figure 24A:
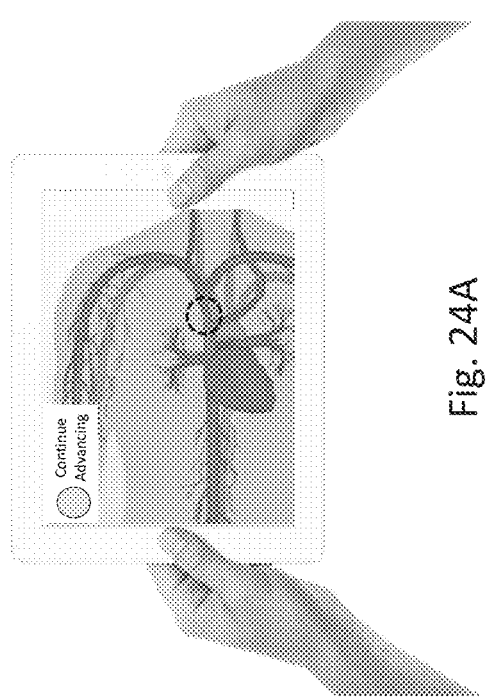
Figure 24B:
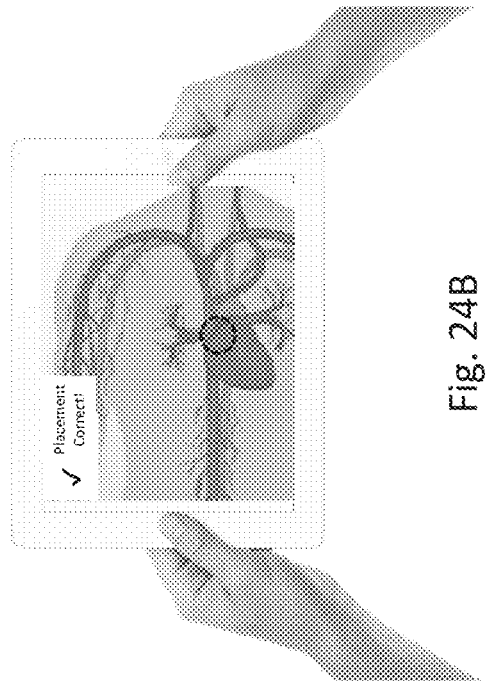
Figure 24C:
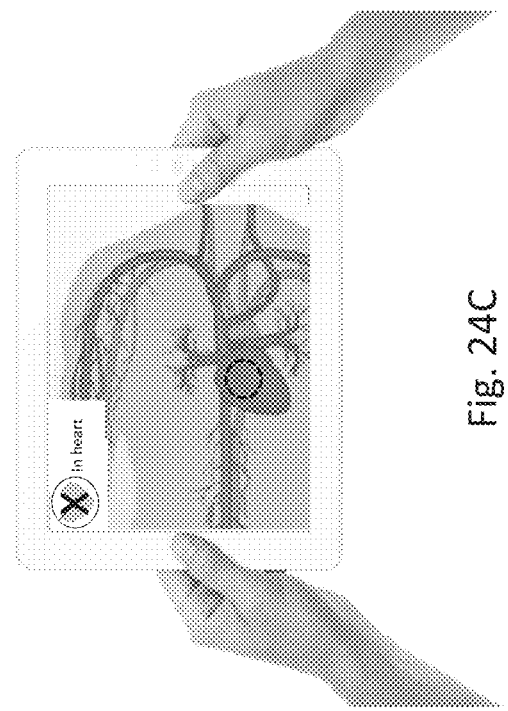
Figure 24D:
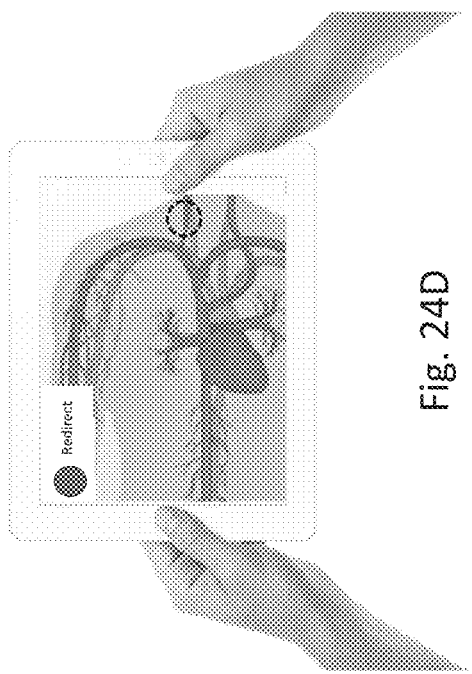

FIG. 20 shows an embodiment of a stylet without an injection lumen. The fluid may be introduced through another catheter lumen (possibly on a separate catheter) upstream from the catheter tip, closer to the insertion site, or elsewhere. For example, fluid may be injected via "buddy" catheter 2002 shown here alongside the vascular catheter. Fluid may also be heated or cooled via a heating/cooling element on the catheter or on a "buddy" catheter. An infusion "buddy" guidewire/stylet is also envisioned.

Figure 21:
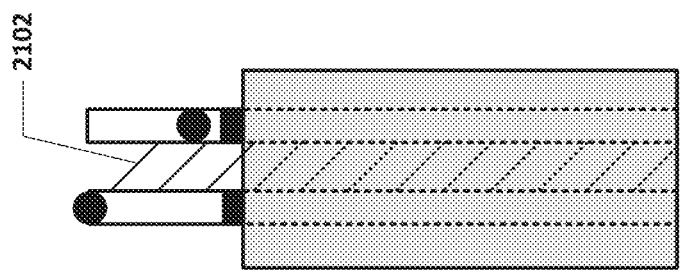
FIG. 21 shows features that enhances a controlled turbulent flow.

FIG. 21 shows features 2102 in the injectate lumen that enhance a controlled turbulent flow.

Figure 22:
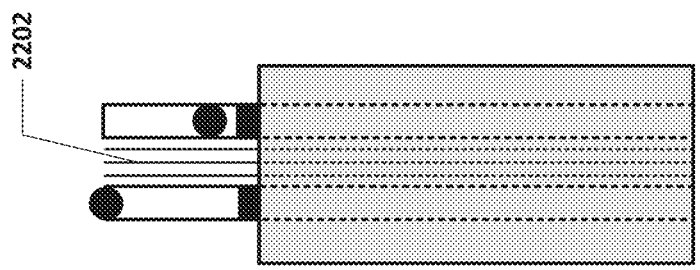
FIG. 22 shows features that create a controlled laminar (or less turbulent) flow.

FIG. 22 shows features 2202 in the injectate lumen that create a controlled laminar (or less turbulent) flow.

Note that several embodiments disclosed herein show 2 sensors. In any of these embodiments, one, two, or more sensors may be used.

In some embodiments the outer diameter (OD) of the stylet is around 1 mm or less. In some embodiments the OD of the stylet is around 0.5 mm or less. In some embodiments the OD of the stylet is around 1.5 mm or less. In some embodiments the stylet could range in OD from about 0.2 mm to about 5 mm.

In some embodiments, where the catheter is double or triple lumen, the stylet functionality may be broken into distinct parts (fluid, stiffener, sensing leads) etc. and multiple stylets may be used in multiple lumens of the catheter.

Many types of temperature sensors may be used in any of the embodiments disclosed herein, including thermocouples, fiber optic, resistive, bimetallic, thermometer, state-change, silicon diode, thermistors, optical temperature measurement (infrared or otherwise), mercury thermometers, manometers, etc.

In addition to infusing fluids, as disclosed elsewhere herein, other methods to create a thermal change at or near the tip of the catheter/stylet may be used. Fluids at a temperature higher than body temperature may be introduced, a resistive heating element, or a piezo electric cooling element, etc. may be included in the catheter, on the catheter, on the guidewire/stylet, or at the injector, outside of the body. Alternatively, the injected fluid may be at a different, although not strictly controlled, temperature than body temperature and this temperature difference (between body temperature and injectate temperature) is measured and tracked by the controller.

In embodiments with a resistive heating element, the resistive heating elements may be on the catheter or on a stylet. In embodiments where it is on the catheter it may be on the outside of the catheter or on the inside of one or more lumens of the catheter. Alternatively, it may be on the guidewire/stylet. In embodiments where it is on the guidewire/stylet, it may be within the catheter lumen, partially within the catheter lumen, or external to the catheter lumen, where it is exposed to blood. Embodiments that heat/cool blood may not require the injectate fluid.

As shown in FIGS. 23A-E and FIGS. 24A-E. A graphical user interface may be displayed in the form of a small screen/display 2314, a large screen, a projection, in virtual reality or augmented reality goggles, etc. The major categorization of user interactions may have any combination of user alerts: 1) icon 2) color of icon or warning light 3) auditory tone that accompanies the alert 4) visual map of the body which matches the location of the catheter tip and with the type of alert 5) written phrase or word on the display indicating the status or alert, vibration, etc. The categories may be the following: 1) 'Continue Advancing', which means that that the catheter tip is advancing through a peripheral vein or has rounded the bend and is approaching the superior vena cava. This mode will be accompanied by visual and auditory feedback indicating a positive state such as green lighting and iconography and a positive tone. 2) 'Placement Correct', with the checkmark iconography shows that the tip has arrived at the proper location—the cavo atrial junction for PICC lines, or perhaps another location for another type of catheter insertion. Positive tone and lighting may also accompany this state. 3) If the catheter encounters an opposing flow, the warning, 'Redirect' may appear. This is the warning if the catheter advances down an azygous branch, advances into the IVC, or has been placed in an artery. Since this is not a positive state, lighting or iconography that is red, yellow or orange may accompany this state along with a tone which depicts that a non-favorable situation is in effect. A less pleasant frequency, pitch and tone may accompany. 4) if the catheter is in the heart, either in the atrium or the ventricle, the user may be alerted with the heart icon and/or "In Heart" warning. A negative color and tone may accompany this state. 5) if the catheter tip is up against a wall of a vein, or has an obstruction of some kind the "Adjust" warning may display. A negative color and tone may accompany this state. Also shown in FIGS. 23A-E and 24A-E is catheter 2302, stylet 2304, sensor adapter 2306, fluid adapter 2308, prime button 2310, and insertion/tracking button 2312.

The graphical user interface (GUI) may display in real time the location of the tip of the catheter relative to the 3D space through which it is navigating. The graphical user interface shown in FIGS. 23A-E and 24A-E are two dimensional, however some embodiments include 3D displays which may also communicate the information in three dimensions.

Note that although some embodiments disclosed herein incorporate the sensor(s) into the vascular catheter, the vascular catheter navigation device may be a stand-alone device which fits inside a vascular catheter, and can be removed once vascular catheter placement has been completed. The vascular catheter navigation device, for example, may serve as a stylet or guidewire for a standard vascular catheter.

FIGS. 25A-C show embodiments of the vascular catheter navigation device which include a conduit to control fluid flow exiting from the fluid exit point of the device. In this embodiment, conduit 2502 is attached to guidewire/stylet 2504, forming a stylus/conduit combination device. Conduit 2502 is designed to fit inside the ID of infusion lumen 2506 of vascular catheter 2508. In this figure, vascular catheter 2508 only includes one lumen, the infusion lumen, however multiple lumens, in addition to the infusion lumen, may exist in the vascular catheter.

In some embodiments, guidewire/stylet 2504 includes core 2510, coil 2512, endcap 2514 and sensor 2516. Core 2510 may include a stiffening wire, which may be tapered, and leads for the sensor. The sensor may be incorporated into the endcap, or it may be separate. One or more sensor(s) may be present. The sensor may be a thermocouple. A larger cross sectional dimension of the sensor may dampen parameter measurements where a smaller cross sectional dimension of the sensor may allow for quicker response times. The diameter or cross sectional dimension 2526 of a sensor may be about 0.2 mm-0.3 mm. Alternatively, the diameter or cross sectional dimension 2526 of a sensor may be about 0.02 mm to about 0.5 mm.

In some embodiments, conduit 2502 has length 2520 and includes fluid flow passage or passages 2518 with diameter or cross sectional dimension 2522. The flow passages may be circular in cross-sectional shape, or oval, or of any shape. A flow passage may be approximately 0.4-0.6 mm in diameter or cross sectional dimension. Alternatively a flow passage may be approximately 0.1-1.0 mm in diameter or cross sectional dimension. Alternatively a flow passage may be approximately 0.01-2.0 mm in diameter or cross sectional dimension. Conduit length 2520 may be about 4-8 mm. Alternatively, conduit length 2520 may be about 0.5 mm-20 mm.

The cross sectional area and shape of the flow passages will, at least partially, determine flow velocity exiting the conduit. The number of flow passages will also affect the flow parameters of the fluid exiting the conduit. Preferably, the fluid infusion rate may be about 2-3 ml/min. Alternatively, the fluid infusion rate may be about 3-5 ml/min. Alternatively, the fluid infusion rate may be about 5-10 ml/min. Alternatively, the fluid infusion rate may be about 1-5 ml/min. Alternatively, the fluid infusion rate may be about 0.5-7 ml/min. Conduit exit flow velocity is preferably about 60-100 cm/sec. Alternatively, conduit exit flow velocity is about 1-300 cm/sec.

Conduit 2502 may serve several purposes:

1) Essentially sealing the distal end of the infusion lumen of the vascular catheter while allowing fluid flow through/past the conduit so that when fluid is infused through the infusion lumen of the catheter, the majority of the fluid exits the vascular catheter via flow passage(s) 2518. It is important to note that the conduit doesn't fully occlude the infusion lumen of the catheter, it allows fluid to pass through it and in some cases, through channels around it.

2) Allowing the distance 2524 between the fluid exit point 2503 and the sensor on the guidewire/stylet to be known and fixed for more controlled parameter measurements in the vasculature. The fluid exit point may be the exit point of the distal end of the flow passage(s) of the conduit, or may be the distal end of the catheter, depending on whether the conduit is partially protruding from the distal end of the catheter. Distance 2524 may be about 0.0 to 1.0 mm. Alternatively, distance 2524 may be about 0.5 to 1.0 mm. Alternatively, distance 2524 may be about 0.0 to 2.0 mm. Alternatively, distance 2524 may be about 0.0 to 5.0 mm. Alternatively, distance 2524 may be about 0.0 to 10.0 mm. "about 0.0" or "Essentially zero" herein may mean plus or minus 1 mm, or "Essentially zero" may mean plus or minus 2 mm, or "Essentially zero" may mean plus or minus 3 mm. This may be the case with any of the embodiments disclosed herein.

3) Centering or otherwise aligning the fluid exit point(s) of the conduit with the sensor(s).

4) centering or otherwise aligning the fluid exit point(s) with the catheter tip 5) Controlling the flow characteristics of the fluid exiting the exit point(s). For example, the size, shape and number of exit ports will, at least partially, control the flow characteristics of the fluid exiting the port(s). Parameters such as turbulence, flow velocity, volumetric flow rate, flow volume, etc. may be controlled. The cross-section of the flow passages 2518, in addition to the fluid infusion rate, will determine the velocity of the infusion rate exiting the flow passages 2518. The velocity of the infusion rate may be adapted to the velocity of the blood flow.

6) Allowing the outer surface of the conduit to essentially seal with the inner surface of the infusion lumen of the vascular catheter without having to perfectly align the guidewire/stylet with the vascular catheter. Because the vascular catheter is larger, and more compressible, than the stylet, the relative alignment of the distal tips of each may vary during a procedure. Where the length of the conduit is longer than this variance, the conduit can still seal the infusion lumen of the vascular catheter even if the distal tips of the stylet/conduit combo and the vascular catheter move with respect to each other. Alternatively or additionally, the conduit may fix the guidewire/stylet to the vascular catheter so that one does not move substantially relative to the other at least longitudinally.

The cross sectional dimension/diameter of the conduit may be about 0.5-1.5 mm. Alternatively, the cross sectional dimension/diameter of the conduit may be about 0.1-3 mm. The clearance between the outside of the conduit and the inside of the infusion lumen of the vascular catheter in some embodiments will be small enough to allow an essential seal between the outside of the conduit and the inside of the infusion lumen of the vascular catheter. This encourages essentially all the infused fluid to exit flow passages 2518 which controls the distance between the fluid exit and the sensor(s). The clearance between the outside of the conduit and the inside of the infusion lumen of the vascular catheter may also be great enough to allow the stylet/conduit combination to move within the infusion lumen of the vascular catheter, for positioning, and/or for removal. The outer surface of the conduit may be coated or manufactured from a lubricious material, such as PTFE, a hydrophobic material, a hydrophilic material, etc. The clearance between the outside of the conduit and the inside of the infusion lumen of the vascular catheter may be about 0.070-0.080 mm. Alternatively, the clearance between the outside of the conduit and the inside of the infusion lumen of the vascular catheter may be about 0.05-0.1 mm. Alternatively, the clearance between the outside of the conduit and the inside of the infusion lumen of the vascular catheter may be about 0.001-1.00 mm.

Note that the clearance between the outside of the conduit and the inside of the infusion lumen of the vascular catheter may be different for embodiments of the conduit which expand/contract, or have features which expand/contract, such as those shown in FIGS. 27, 28, 29A-C, 30, 36A-C. For example, the clearance in the contracted state may be greater than that of a conduit which does not expand/contract and the clearance in the expanded state may be less than that of a conduit which does not expand/contract. For example, the clearance in the expanded state may be essentially zero.

FIG. 25A shows the distal end of conduit 2502 essentially aligned with the distal end of catheter 2508. (Note that "distal" herein means the end of the vascular catheter navigation device which enters the body. "Proximal" herein means the end of the vascular catheter navigation device which does not enter the body.) FIG. 25B shows an embodiment where the distal end of the conduit is designed to sit inside the distal end of the infusion lumen of the catheter for infusion. FIG. 25C shows an embodiment where the distal end of the conduit is designed to sit outside the distal end of the distal end of the infusion lumen of the catheter for infusion. Note that some embodiments may be designed to sit in more than one position.

The fluid exit point 2503 is shown for the devices in FIGS. 25A-25C and in other figures. Note that the exit point may be the distal end of the conduit, or the distal end of the catheter, depending on the alignment of the conduit with the distal end of the catheter.

In use, the stylet/conduit combination device is inserted (or comes inserted) into the infusion lumen of the vascular catheter. The catheter is then inserted into, and advanced through, the vasculature. As the device is advanced, fluid is infused through the infusion lumen. Because the conduit essentially seals the infusion lumen of the catheter, the fluid exits the system through the flow passages of the conduit, and the fluid flows through the vasculature and the sensed parameter of the blood/fluid in the vasculature is sensed by the sensor. The distance between the exit point(s) of the fluid and the sensor is fixed/known and the parameter vs. time/location curve is related to the flow characteristics within the vessel. The different signatures of these curves are used to identify the location of the tip of the vascular catheter navigation device. After the system has been navigated to its desired location, the stylet/conduit combination device is removed, and the infusion lumen of the vascular catheter serves as a standard infusion lumen. The stylet/conduit combination device may be reinserted into the infusion lumen of the vascular catheter later on to confirm the location of the tip of the vascular catheter.

Figure 26:
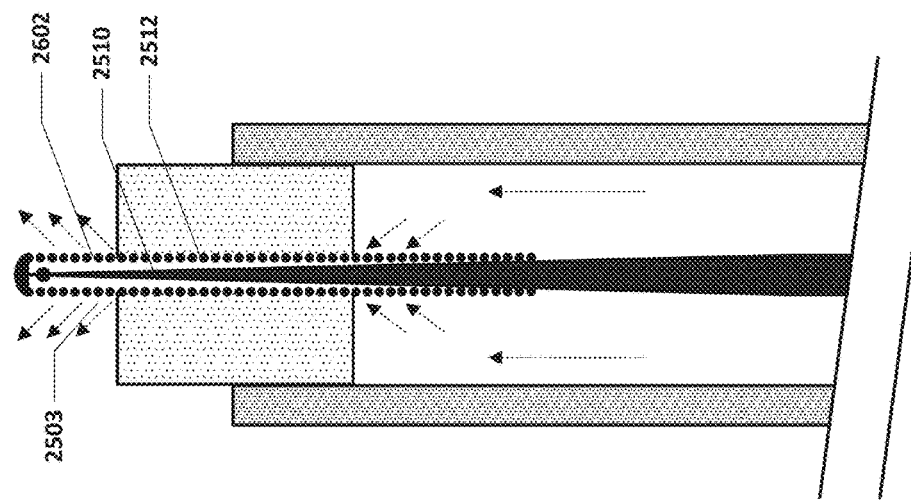
FIG. 26 shows an embodiment of the vascular catheter navigation device where the flow passage is within the guidewire/stylet component itself.

FIG. 26 shows an embodiment of the vascular catheter navigation device where the flow passage is within the guidewire/stylet component itself. In this embodiment, the conduit serves to essentially seal the end of the infusion lumen of the catheter, but the flow passage flows between stylet core 2510 and stylet coil 2512 and exits via openings 2602 between the coils.

In some embodiments, the seal between the conduit and the catheter may be an O-ring, bulge, flange, flare, balloon, compression seal, hydrophilic material or other sealing mechanism. The seal may be part of the conduit, such as a flare, bulge, or flange, or the seal may be a separate component, such as an O-ring. The seal may be manufactured in any suitable manner including injection molding. In some embodiments the seal is on the stylet/conduit, while in some embodiments the seal is on the catheter. In some embodiments, the seal is on a combination of the stylet/conduit and the catheter.

Figure 27:
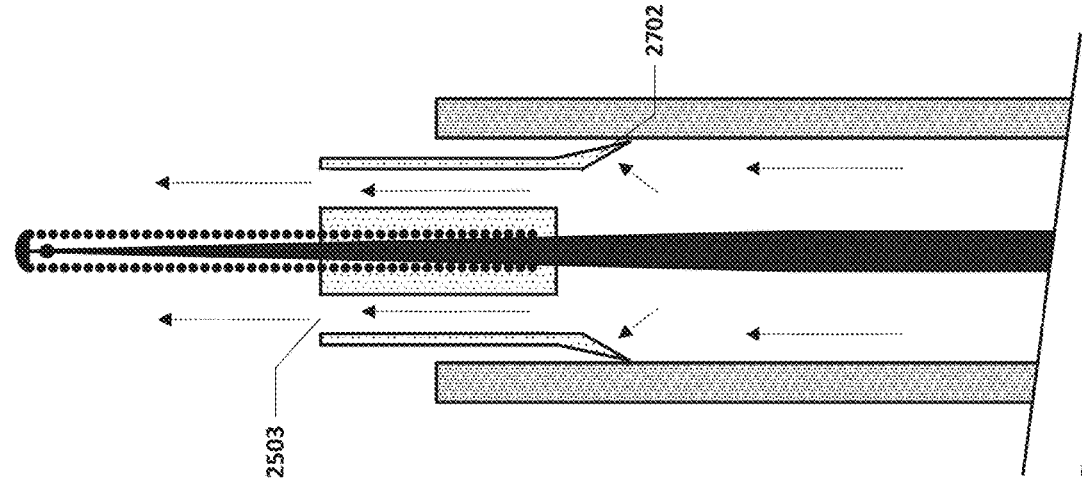
FIG. 27 shows a variation of the conduit which includes a proximal flange.

FIG. 27 shows a variation of the conduit which includes proximal flange 2702. The flange may serve as a seal, essentially sealing the conduit to the ID of the infusion lumen of the catheter, when fluid injected through the infusion lumen of the catheter above a certain pressure. A flange may be rigid, semi-rigid or flexible. When fluid is no longer infused through the infusion lumen, or when the infusion pressure is reduced below a certain pressure, flange 2702 may collapse slightly, reducing the diameter or cross sectional area of the conduit at the flange, which allows the stylet/conduit combination device to be removed from the vascular catheter after location of the vascular catheter has been established. Alternately, the flange may invaginate and flip direction during withdrawal movement, easing removal of the stylet/conduit combination device.

Figure 28:
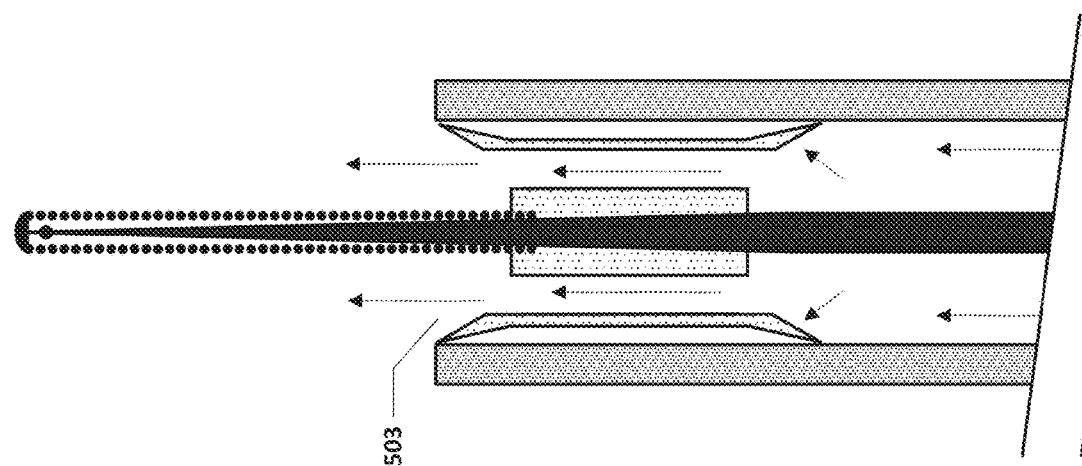
FIG. 28 shows a variation of the embodiment shown in FIG. 27 where the conduit has both a proximal flange and a distal flange.

FIG. 28 shows a variation of the embodiment shown in FIG. 27 where the conduit has both a proximal flange and a distal flange. Note that, in these, as well as other embodiments disclosed herein, during use, i.e., during catheter navigation, the distal end of the conduit may be flush with the distal tip of the catheter, distal to the distal end of the catheter, or proximal to the distal end of the catheter.

Figure 29C:
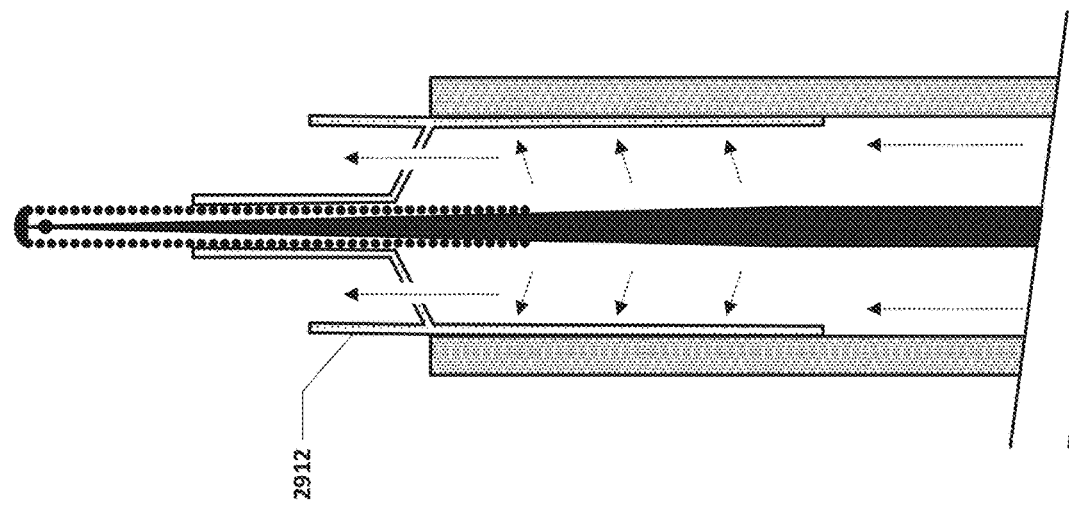
FIGS. 29A-C show an embodiment of the vascular catheter navigation device where the conduit includes a thin-walled inflatable structure.
Figure 29B:
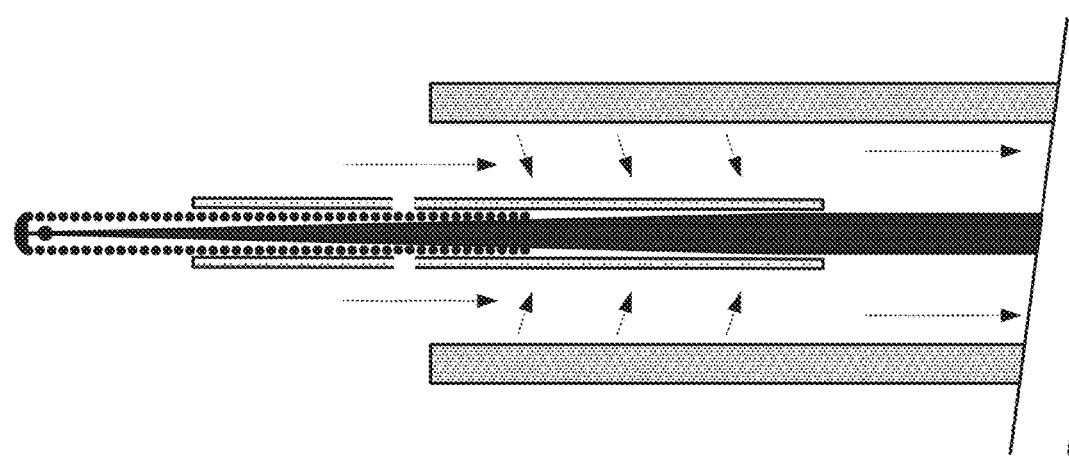
Figure 29A:
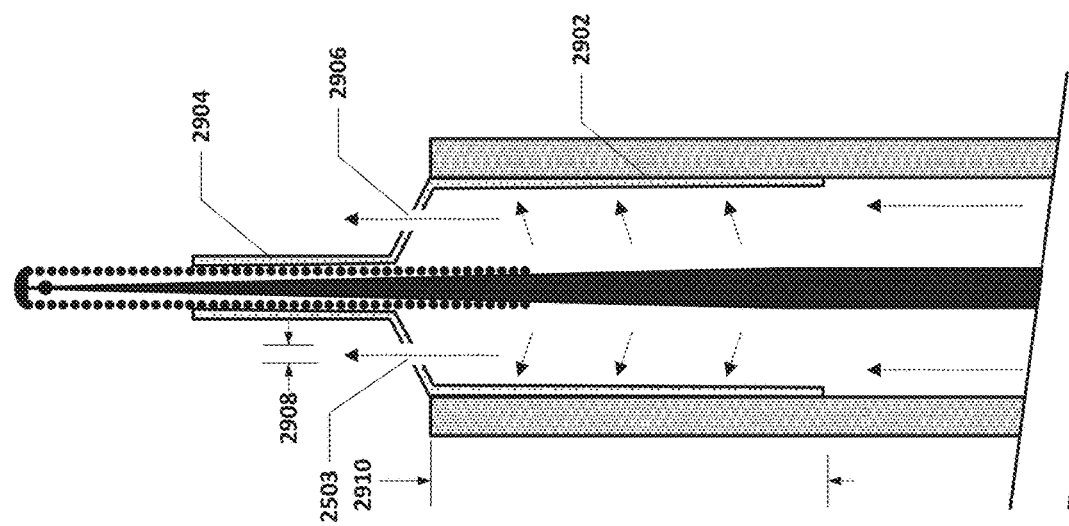

FIGS. 29A-C show a embodiments of the vascular catheter navigation device where the conduit includes a thin-walled inflatable structure. FIG. 29A shows a conduit with thin-walled, inflatable proximal portion 2902 and distal portion 2904, where distal portion is bonded, or otherwise attached, to the stylet. Proximal portion 2902 of the conduit includes opening(s) 2906. Proximal conduit portion 2902 expands when fluid in infused through the infusion lumen of the catheter, essentially sealing the inflatable portion up against the inner walls of the infusion lumen. The infusion fluid also exits the catheter via openings 2906. The openings may be small enough to allow the pressure within portion 2902 to increase so that this portion "inflates" inside the infusion lumen. The openings may be large enough to allow adequate fluid to escape into the blood stream to make meaningful parameter measurements. The diameter or cross-sectional dimension of the opening(s) may be about 0.4-0.06 mm. Alternatively, the diameter or cross-sectional dimension of the opening(s) may be about 0.05-1.0 mm. The length 2910 of proximal section 2902 of the conduit may be about 0.3-0.5 mm. Alternatively, the length 2910 of proximal section 2902 of the conduit may be about 0.3-20 mm.

To remove the stylet/conduit component from the vascular catheter, the fluid infusion is reduced, or reversed, to "deflate" proximal section 2902 of the conduit so that the stylet/conduit can be removed. This is shown in FIG. 29B. In some embodiments, deflation may not be necessary and the stylet/conduit may be removed from the vascular catheter while fluid infusion is taking place.

FIG. 29C shows a variation of the inflatable conduit with collar 2912 which may help direct fluid flow as it exits the conduit.

One of the advantages of an "inflatable" conduit is that the shape of the conduit can conform to any shaped infusion lumen, whether round, semi-circle, triangular, oval, etc. The difference in cross sectional area between the deployed vs. un-deployed conduit can be fairly great, which is useful in smaller infusion lumen devices.

Figure 30:
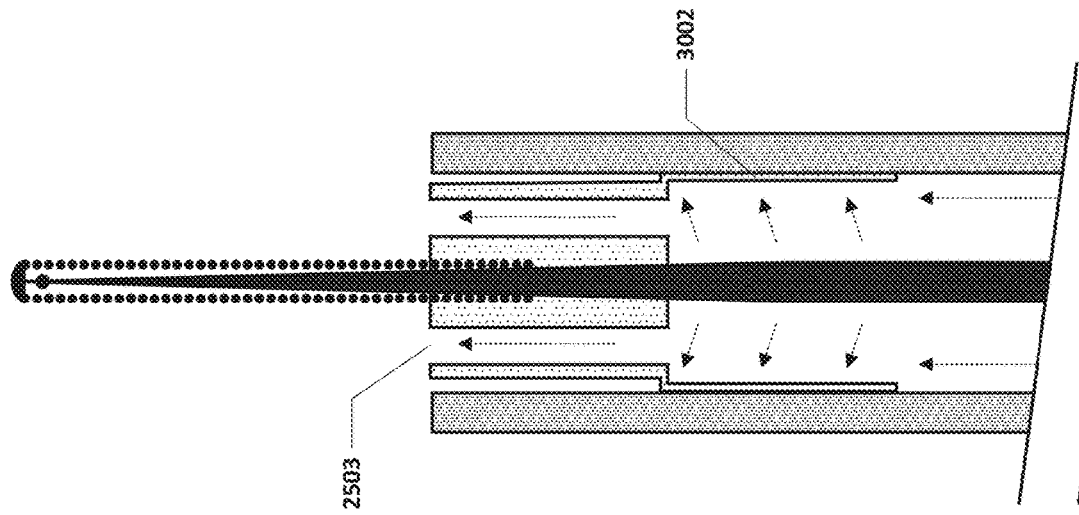
FIG. 30 shows an embodiment which includes a thin-walled "skirt".

FIG. 30 shows an embodiment of the conduit which has thin-walled "skirt" 3002. This "skirt" expands and contracts similar to the "inflatable" portion of the embodiment shown in FIGS. 29A and B.

Figure 32:
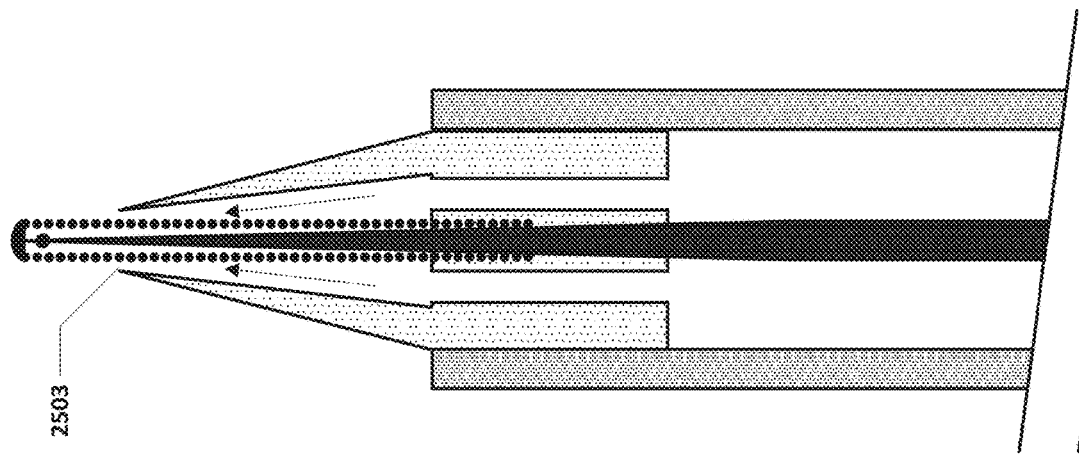
FIG. 31-33 show embodiments where the conduit includes feature(s) to help direct the fluid flow exiting the conduit.
Figure 31:
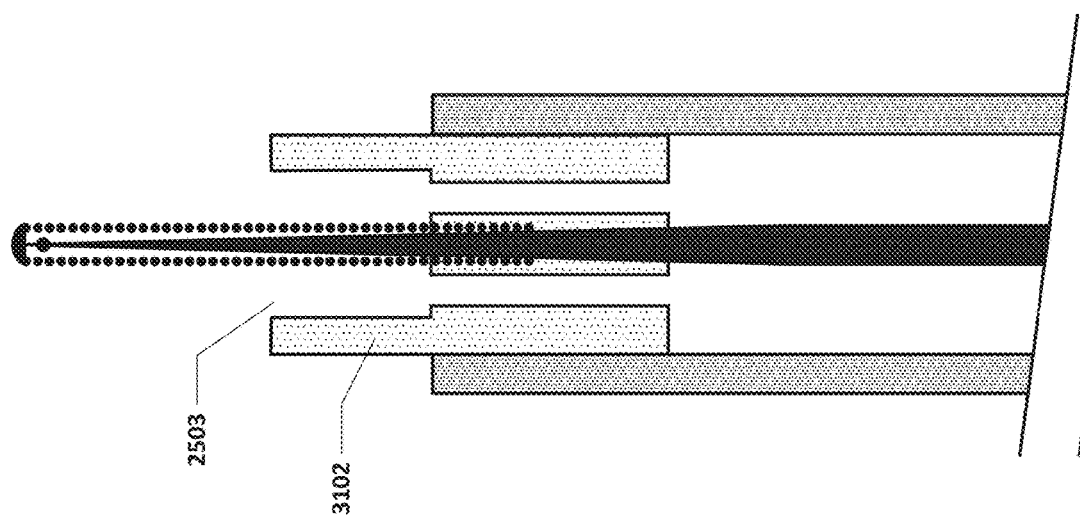
Figure 33:
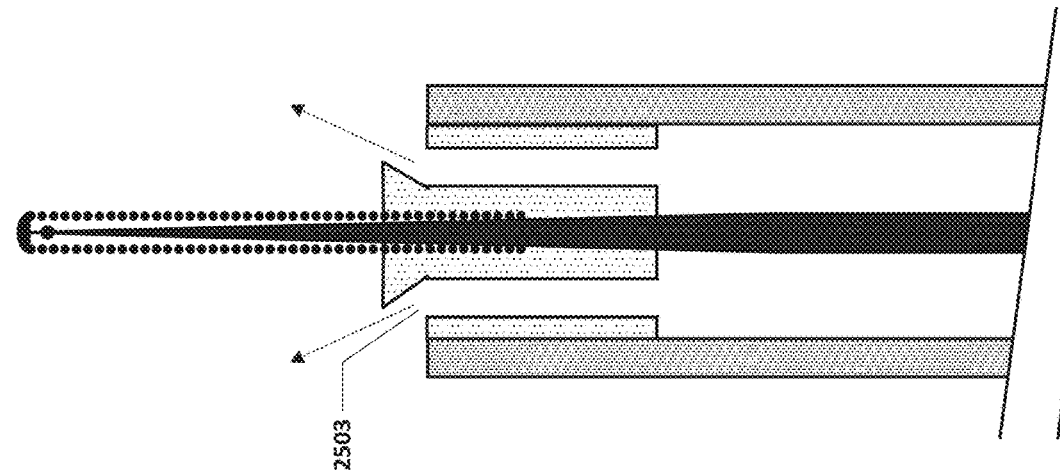

FIG. 31 shows an embodiment of the conduit which includes feature(s) 3102 to help direct the fluid flow exiting the conduit. The feature may direct flow in a parallel manner, as shown in FIG. 31, inward, as shown in FIG. 32, or outwardly, as shown in FIG. 33, or in any other manner.

Figure 34:
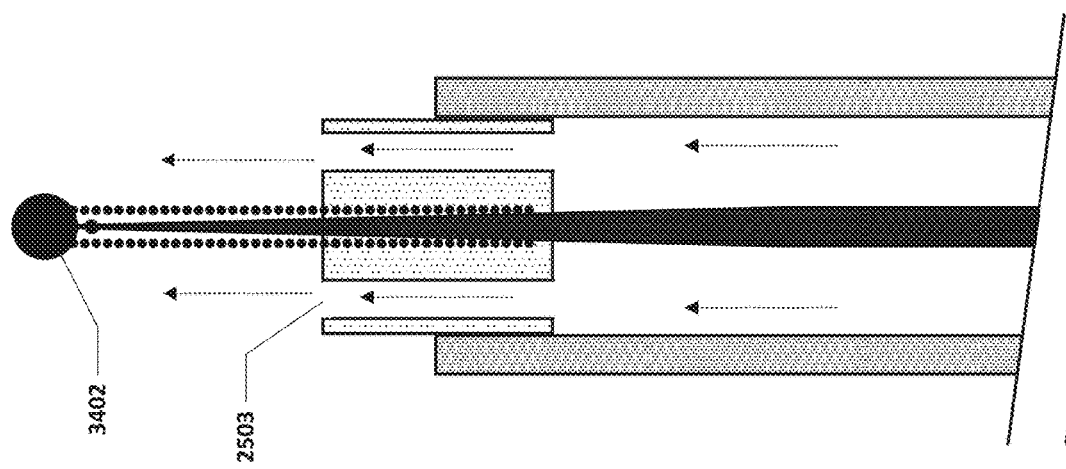
FIG. 34 shows an embodiment with a deflector.

FIG. 34 shows an embodiment with deflector 3402 which helps keep the system away from the wall of the blood vessel. The deflector may be a sphere, or essentially spherical in shape or any other shape. The diameter or cross section dimension of the deflector may be about 0.3-0.4 mm. Alternatively, the diameter or cross sectional dimension of the deflector may be about 0.01-1.0 mm.

Figure 35:
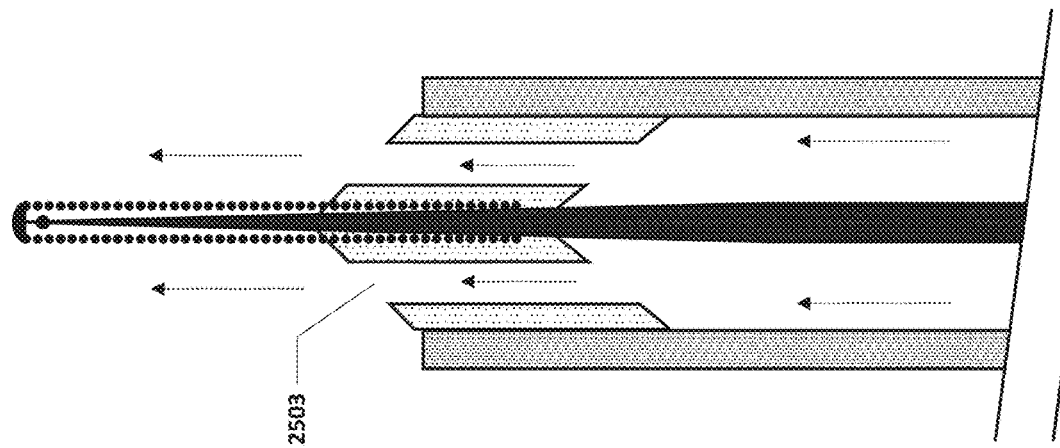
FIG. 35 shows an embodiment of the conduit which is conical shaped.

FIG. 35 shows an embodiment of the conduit which is conical shaped to help seal within the infusion lumen of the catheter during injection.

FIGS. 36A-C show an embodiment of the vascular catheter navigation device which includes a compressible conduit 3606. The compressible conduit may be made out of silicone, polymer, or other suitable material. FIG. 36A shows the conduit in its compressed state. In this state, the conduit essentially seals the infusion lumen of the catheter. FIG. 36B shows the compressible conduit in its uncompressed state, which reduces the diameter/cross-sectional dimension so that it may be repositioned and/or removed. The compressing/uncompressing of the conduit may be performed by rod or hypotube or tube 3602 which is connected to the proximal end of the compressible conduit and can be manipulated (pushed, pulled, twisted etc.) from the proximal end of the catheter to compress and uncompress the conduit. FIG. 36C shows a variation of the system which allows the user to compress/uncompress the conduit by rotating rod/hypotube/tube 3604 which has threads which engage with the conduit.

FIGS. 37A-F show 2 different cross-sectional views of some embodiments of the vascular catheter navigation device. FIG. 37A shows an embodiment where guidewire/stylet 2504 is generally centered in conduit 2502 within infusion lumen of vascular catheter 2508. Flow passage(s) 2518 may have different cross sectional shapes, for example, spherical, triangular, those shown here and others. One, two, or more flow passages may be present. The guidewire/stylet may include sensor lead wires 3702. The lead wires may be from about 0.001" to about 0.005" in diameter, for example, copper magnet wire.

FIG. 37B shows an embodiment of the vascular catheter navigation device where the guidewire/stylet is off center. The cross sectional views show various possible configurations of the guidewire/stylet and fluid passages. The flow passage(s) may be circular, crescent shaped etc. one, two or more flow passages may be present in any of the embodiments disclosed herein. Note that the conduit may be a simple tube, as shown by 3704.

FIG. 37C shows an embodiment of the vascular catheter navigation device where the guidewire/stylet is off center and the tip of the guidewire/stylet is angled to align with flow passage in the conduit so that sensor 2516 is approximately aligned with a flow passage. The tip of the guidewire/stylet may be aligned in other ways as well, for example, to fall between flow passages or to simple be near the center of the catheter. The cross sectional views show various possible configurations of the guidewire/stylet and fluid passages. The flow passage(s) may be circular, crescent shaped etc. The conduit may be a simple tube.

FIG. 37D shows an embodiment of the vascular catheter navigation device where the conduit is a simple tube, and the guidewire/stylet is either floating in the ID of the conduit (here the ID of the conduit is the same as the flow passage of the conduit), or attached to the inner wall of the conduit. The guidewire/stylet may be angled so that the sensor is more aligned with the center of the conduit flow passage, or straight, or bent or curved in some other way.

FIG. 37E shows an embodiment of the vascular catheter navigation device which includes cage or scaffold 3706 which centers sensor 2516 over a central flow passage within the conduit. The cage/scaffold may be made from metal wire, polymer, may be made from a porous material, etc. Cage/scaffold may be embedded in, or attached to, the conduit.

FIG. 37F shows an embodiment of the vascular catheter navigation device where conduit 2502 does not have an outer surface. In this embodiment, flow passages are in direct contact with the ID of catheter 2508.

FIGS. 38A-E show some possible architectures of various embodiments of the vascular catheter navigation device. FIG. 38A shows vascular catheter 2508, guidewire/stylet 2504 and conduit 2502, along with IV bag 3802, with optional infusion pump 3804, where the infusion bag is connected to the fluid infusion port 2806 of the vascular catheter. The guidewire/stylet is inserted/removed to/from the catheter via stylet port 3808. In some embodiments, the stylet port of the catheter may be the same port as the infusion port. Stylet/sensing connector 3810 connects to controller 3812, which may include display 3814, as well as one or more controls 3816. In this embodiment the infusion of fluid through the vascular catheter and through the flow passage(s) of the conduit is controlled by the IV bag/infusion pump. The IV bag may be set to a consistent drip, flow, and/or may be controlled by the infusion pump. In this embodiment, the IV bag and/or infusion pump, is connected to the vascular catheter without going through the controller. FIG. 38B shows a similar embodiment, except that the flow of IV fluid from the IV bag is controlled by the controller. IV bag 3802 is connected to the controller via IV fluid line 3818. The controller controls the infusion of fluid from the IV bag and delivers the fluid to the catheter via catheter fluid line 3820. The controller could be disposable or re-usable. The kit could also come with disposable lines which attach to the IV bag or hospital's infusion pump.

FIG. 38C shows an embodiment of the vascular catheter navigation device which includes fluid pump 3822, such as a syringe pump. The fluid pump may be a standard off the shelf fluid pump. It could be a peristaltic pump or a pump driven by a lead screw. Note that in this embodiment, the fluid pump does not connect to the controller.

FIG. 38D shows an embodiment where fluid pump 3824 connects to the controller, so that the controller can control the fluid delivery to the catheter via the fluid pump. The controller may have a module that allows the user to attach an off the shelf fluid pump, or the controller may require a specific fluid pump. The connection may be through an electrical connection or the controller may control the infusion or fluid pump through a wireless protocol such as Bluetooth, Wi-Fi, or other. The fluid pump and/or the syringe cartridge within the fluid pump may be disposable.

FIG. 38E shows an embodiment where the fluid pump is incorporated into controller 3812. The fluid pump and/or the syringe cartridge within the fluid pump may be disposable.

FIG. 39A is a longitudinal cross sectional view of the vascular catheter navigation device including conduit 2502, guidewire/stylet 2504, sensor 2516 and vascular catheter 2508.

FIG. 39B shows an embodiment of the vascular catheter navigation device with multiple conduits along the length of the guidewire/stylet. There may be 0, 1, 2, 3, 4, 5, 6 or more conduits.

FIG. 39C shows an embodiment of the vascular catheter navigation device with conduit 2502, as well as securing style conduits 3902. In some embodiments, these securing style conduits are inflatable, such as balloons, but they may also be compressible, such as silicone or another soft/compliant material, such as any suitable polymer. The securing style conduit may alternatively be made from a harder material, such as epoxy, or metal, or polymer etc. Preferably, the securing style conduits secure the guidewire/stylet to the inner lumen of the catheter so that the stylet does not move significantly longitudinally with respect to the catheter. As a result, the distance between the fluid exit point, and the sensor, is essentially fixed. Movement of the sensor with respect to the fluid exit point may be limited to plus or minus 1 mm. Or Movement of the sensor with respect to the fluid exit point may be limited to plus or minus 2 mm. Or Movement of the sensor with respect to the fluid exit point may be limited to plus or minus 3 mm. Preferably, a securing style conduit also allows fluid to flow past it as it is securing, and through the catheter lumen during infusion. There may be zero, 1, 2, 3, 4, 5, 6 or more securing style conduits. In embodiments where the guidewire/stylet includes a balloon, it will also include an inflation lumen. Balloons may be relatively non-compliant or relatively compliant. The advantage of a non-compliant balloon is that it will retain its shape, or roundness, when inflated beyond a critical pressure. This will prevent the balloon from conforming to the infusion lumen thus filling it. Instead, a non-compliant balloon will remain relatively circular when inflated, and fluid flow lumens will be available between the inner wall of the catheter infusion lumen, the stiffener/electrodes, and the securing style conduit, as shown in FIG. 39G.

FIG. 39D shows an embodiment of the vascular catheter navigation device with securing style conduit 3902. In this embodiment, the securing style conduit may serve as the conduit. The securing style conduit may be at the tip of the catheter or it may be further back proximally from the tip of the catheter, by length 3904. Length 3904 may be about 0-0.5 mm. Alternatively, length 3904 may be about 0-1.0 mm. Alternatively, length 3904 may be about 0.5-1.0 mm. Alternatively, length 3904 may be about 0-5 mm. Alternatively, length 3904 may be about 0-10 mm. Alternatively, length 3904 may be about 0-20 mm. Alternatively, length 3904 may be about 0-30 mm. Alternatively, length 3904 may be about 0-40 mm. Alternatively, length 3904 may be about 0-50 mm. Alternatively, length 3904 may be about 0-60 mm. Alternatively, length 3904 may be about 0-70 mm. Alternatively, length 3904 may be about 0-80 mm. Alternatively, length 3904 may be about 0-90 mm. Alternatively, length 3904 may be about 0-100 mm.

Length 3905 is the length between the sensor and the tip of the catheter, which in this embodiment, is the fluid exit point. The securing style conduit secures the guidewire/stylet to the infusion lumen of the catheter essentially fixing length 3905 during placement. Length 3905 may be about 0-0.5 mm. Alternatively, length 3905 may be about 0-1.0 mm. Alternatively, length 3905 may be about 0.5-1.0 mm. Alternatively, length 3905 may be about 0-5 mm. Alternatively, length 3905 may be about 0-10 mm. Alternatively, length 3905 may be about 0-20 mm. Alternatively, length 3905 may be about 0-30 mm. Alternatively, length 3905 may be about 0-40 mm. Alternatively, length 3905 may be about 0-50 mm. Alternatively, length 3905 may be about 0-60 mm. Alternatively, length 3905 may be about 0-70 mm. Alternatively, length 3905 may be about 0-80 mm. Alternatively, length 3905 may be about 0-90 mm. Alternatively, length 3905 may be about 0-100 mm.

The length of securing style conduit 3902 may be around 1 mm. Alternatively, the length of securing style conduit 3902 may be around 1-2 mm. Alternatively, the length of securing style conduit 3902 may be around 1-3 mm. Alternatively, the length of securing style conduit 3902 may be around 1-4 mm. Alternatively, the length of securing style conduit 3902 may be around 0.5-5 mm.

FIGS. 39E-39G show radial cross section views which reveal some of the embodiments of securing style conduit 3902. In FIG. 39E there are 3 balloons, or soft protrusions around guidewire/stylet 2504. FIG. 39F shows 2 balloons/protrusions and FIG. 39G shows only one balloon/protrusion. Note that the flow passage(s) 3906 of these securing style conduits is the space(s) between the securing style conduit and the inner lumen of catheter 2508, and similar to the conduit shown in FIG. 37F, does not have an outer surface. In several of these embodiments, flow passages are in direct contact with the ID of catheter 2508.

In one embodiment, securing style conduit 3902 is a small silicone protrusion or inflatable balloon near the distal end of the stylet/guidewire and as such, serves as the conduit. Before insertion, the guidewire/stylet is placed into the desired position so that the sensor is correctly positioned with respect to the distal tip of the catheter. At this point, the securing style conduit may be "activated", for example, by inflating the balloon. The securing style conduit holds the relative position of the guidewire/stylet and the catheter during the placement process. During the placement process, fluid is injected through the catheter, past the securing style conduit and out the distal tip of the catheter. For removal, the securing style conduit is either deflated, or is flexible enough to then allow the guidewire/stylet to be removed from the catheter. Sealing style conduit 3902, when activated may be at a cross sectional dimension which is greater than that of guidewire/stylet 2504. The cross sectional dimension of the conduit may be about 0.05 mm greater than that of the guidewire/stylet. Alternatively, the cross sectional dimension of the conduit may be about 0.05-0.1 mm greater than that of the guidewire/stylet. Alternatively, the cross sectional dimension of the conduit may be about 0.05-0.5 mm greater than that of the guidewire/stylet. Alternatively, the cross sectional dimension of the conduit may be about 0.5-1.0 mm greater than that of the guidewire/stylet. Alternatively, the cross sectional dimension of the conduit may be about 1.0-2.0 mm greater than that of the guidewire/stylet.

FIG. 39H shows an embodiment of the vascular catheter navigation device which includes multiple securing style conduits 3902. Multiple securing style conduits may allow for better longitudinal fixation between the guidewire/stylet and the catheter near the distal end of each. Note in this example, length 3905 is essentially zero, which is the case when sensor 2516 is essentially at the distal tip of the catheter. "Essentially zero" may mean plus or minus 1 mm, or "Essentially zero" may mean plus or minus 2 mm, or "Essentially zero" may mean plus or minus 3 mm. This may be the case with any of the embodiments disclosed herein.

FIG. 39I shows an embodiment of the vascular catheter navigation device where securing style conduit is a helix. The helix stabilizes and centers the guidewire/stylet within the infusion lumen of the catheter, while allowing fluid to flow past the conduit. The helix is preferably open on the ends to allow fluid to flow therethrough.

FIG. 39J shows an embodiment of the vascular catheter navigation device where securing style conduit 3902 is one or more metal wires or filaments, which secure the stylet with respect to the catheter lumen via outward mechanical force. The filaments may run the length of the guidewire/stylet and may be expanded/retracted using a mechanism at the proximal end of the guidewire/stylet. The filaments may be single strands of metal, or may be a cage, or spiral etc.

FIG. 39K shows an embodiment of the vascular catheter navigation device with conduit 2502 running the length, or essentially the entire length, of catheter 2508. Optional securing mechanism 3908 is shown here. The securing mechanism secures the conduit to the catheter so that one does not move substantially longitudinally with respect to the other. The securing mechanism in this embodiment does not need to allow fluid to flow past it as the injection lumen is incorporated into the conduit.

Markings or any other mechanism may be used to align the conduit with the distal end of the catheter for catheter navigation. For example, a moveable marker may exist on the proximal end of the guidewire/stylet so that the distal tip of the vascular catheter (possibly after having been cut to length) can be aligned with the conduit outside of the body, the moveable marker moved so that it lines up with the proximal end of the vascular catheter, and then the catheter may be inserted into the body. Other mechanisms include valves, such as a tuohy-borst valve, or clamps, torque device, etc. The length of the conduit may be long enough so that exact alignment of the distal tips of the catheter and the conduit is not necessary. For example, the vascular catheter may move about 0-2 mm with respect to the guidewire/stylet during the placement procedure. Alternatively, the vascular catheter may move about 0-4 mm with respect to the guidewire/stylet during the placement procedure. The conduit may be longer than this, for example, about 2-12 mm, to accommodate for these changes in alignment and ensure that the conduit spans the distal tip of the catheter.

Some embodiments of the vascular catheter navigation device may restrict the conduit from exiting the distal end of the vascular catheter. Some embodiments may allow the conduit to exit the distal end of the vascular catheter. The proximal end of the conduit may be tapered to a smaller cross sectional area proximally so that the conduit can be pulled back into the catheter without catching.

FIGS. 40A-C show some different configurations of vascular catheter lumens and variations of embodiments of the vascular catheter navigation device which work with them. Vascular catheters may have one, two, three, four, five or more lumens. FIG. 40A shows some example configurations of 2 lumen vascular catheters. These configurations include infusion lumen 2506 and auxiliary lumen 4002. The auxiliary lumen may be an additional infusion lumen, a sampling lumen, a pressure lumen, a guidewire/stylet lumen, a tools lumen, or a lumen used for any other purpose. Shown here are guidewire/stylet 2504, conduit 2502, flow passage(s) 2518 and vascular catheter 2508. Some of the various components of the vascular catheter navigation device, including the stylet, conduit, and flow passage(s) may have different cross sectional shapes to accommodate the different shape vascular catheter lumens. Some examples are shown here, but others are envisioned. The shape of the conduit may be preformed, for example in the form of a polymer conduit, or may take on the shape of the lumen, for example via an inflatable or conformable conduit, for example as shown in FIGS. 27, 28, 29A-C, 30, and 36A-C.

FIG. 40B shows some examples of configurations of 3 lumen vascular catheters. FIG. 40C shows an example of a configuration of a 4 lumen vascular catheter.

Although some embodiments of the vascular navigation device shown here in multi-lumen catheters show the vascular navigation device conforming to the shape of the lumen, the vascular navigation may have different cross sectional shapes, including round.

Note that although embodiments disclosed herein show the vascular catheter navigation device in an infusion lumen of a vascular catheter, it is also possible that the vascular catheter navigation device may be used in any lumen of a vascular catheter, for example a sampling lumen. It is also possible that more than one vascular catheter navigation devices may be used at once in more than one lumen.

Figure 41A:
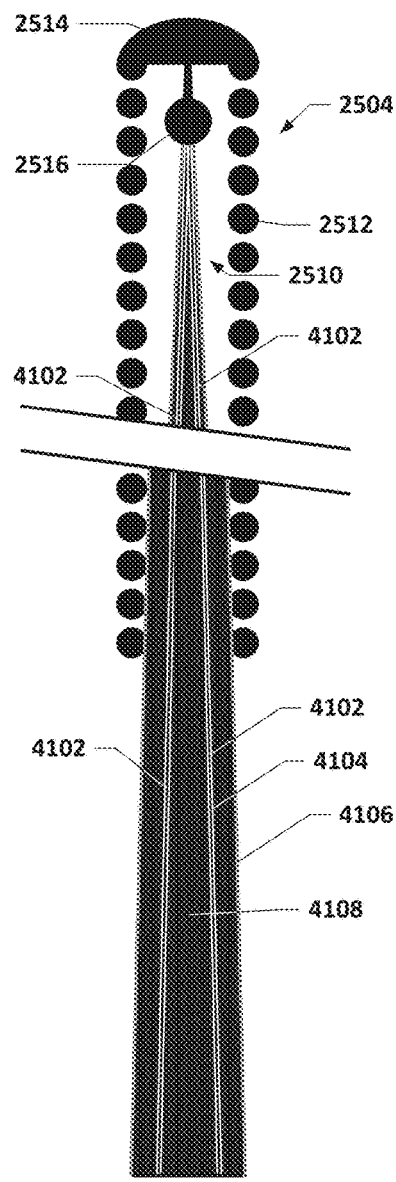
FIGS. 41A-F show various embodiments of a guidewire/stylet component of the vascular catheter navigation device.

FIGS. 41A-F show various embodiments of a guidewire/stylet component of the vascular catheter navigation device. FIG. 41A shows guidewire/stylet 2504, including core 2510, coil 2512, endcap 2514 and sensor 2516. Also shown here are sensor lead wires 4102, sensor lead wire insulation layer 4104, stiffener 4108 and core enclosure 4106. The sensor lead wires connect the sensor on the distal end of the device to the controller on the proximal end of the device. There may be one, two or more lead wires. For example, a thermocouple will usually have 2 lead wires. Some thermocouples, however, may have 3 lead wires if one of the lead wires is a ground wire. The lead wires are preferably made out of metal. The lead wires may be insulated with insulation layer 4104 which surrounds each lead wire. In some embodiments, only one of the lead wires is insulated. The insulation material may be made out of polymer such as polyethylene or PTFE or polyimide or other suitable material and may or may not be heat shrinkable. The lead wire may be made out of metal, such as copper, stainless steel or other suitable material. The stiffener may be made out of metal (such as nitinol or stainless steel, etc.) and may be tapered to a smaller cross sectional dimension at the distal tip, or the stiffener may have a consistent cross section over its length. The stiffener may be round in cross sectional area or may be any other shape. The stiffener may alternatively be a polymer. The lead wire(s) may serve as the stiffener in which case, and additional stiffener will not be present.

The core, which includes the lead wire(s) and an additional stiffener, if present, may be encapsulated with enclosure 4106. Enclosure 4106 may be a tube made out of polymer, such as polyimide, polyethylene, PTFE etc., or metal or other suitable material. The enclosure may alternatively be a dip or spray coating. The enclosure may be a heat shrinkable tubing.

Figure 41B:
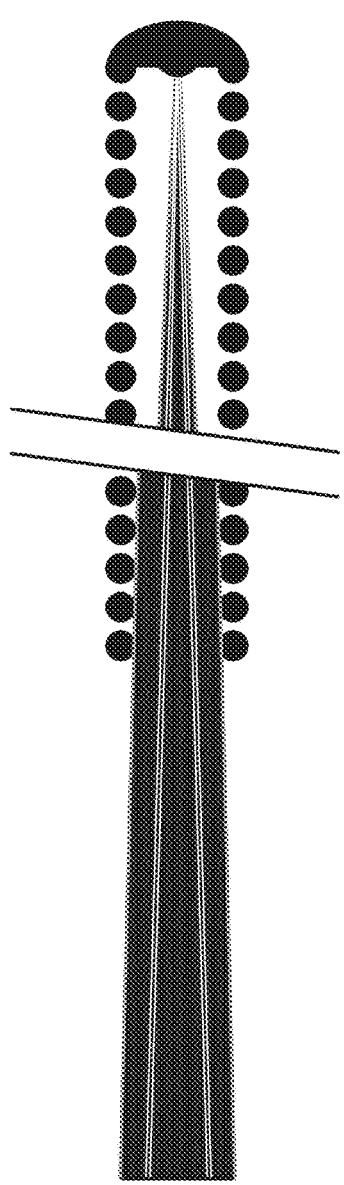
Figure 41C:
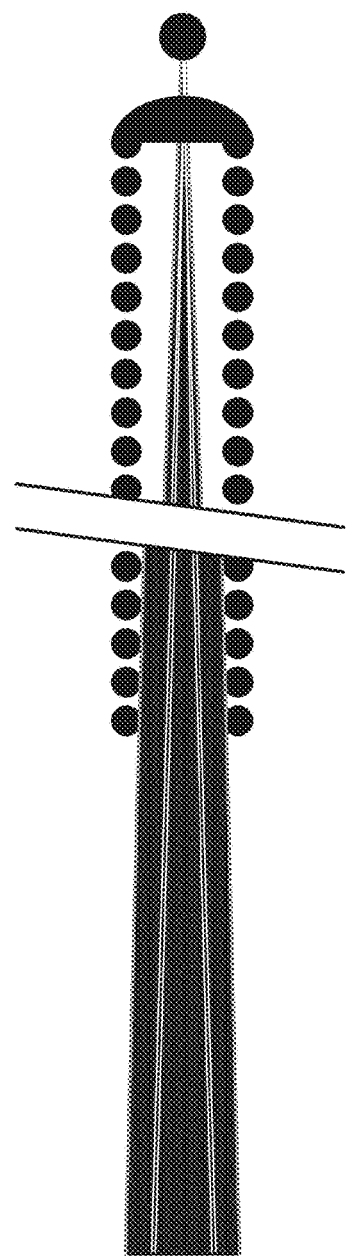

FIG. 41A shows a guidewire/stylet where lead wires travel to the distal end of the stylet where sensor 2516 exists separately from endcap 2514 and proximally to the endcap. FIG. 41B shows an embodiment where the endcap and the sensor are combined. FIG. 41C shows an embodiment where the sensor is distal to the endcap.

Figures 41D, 41E, 41F:
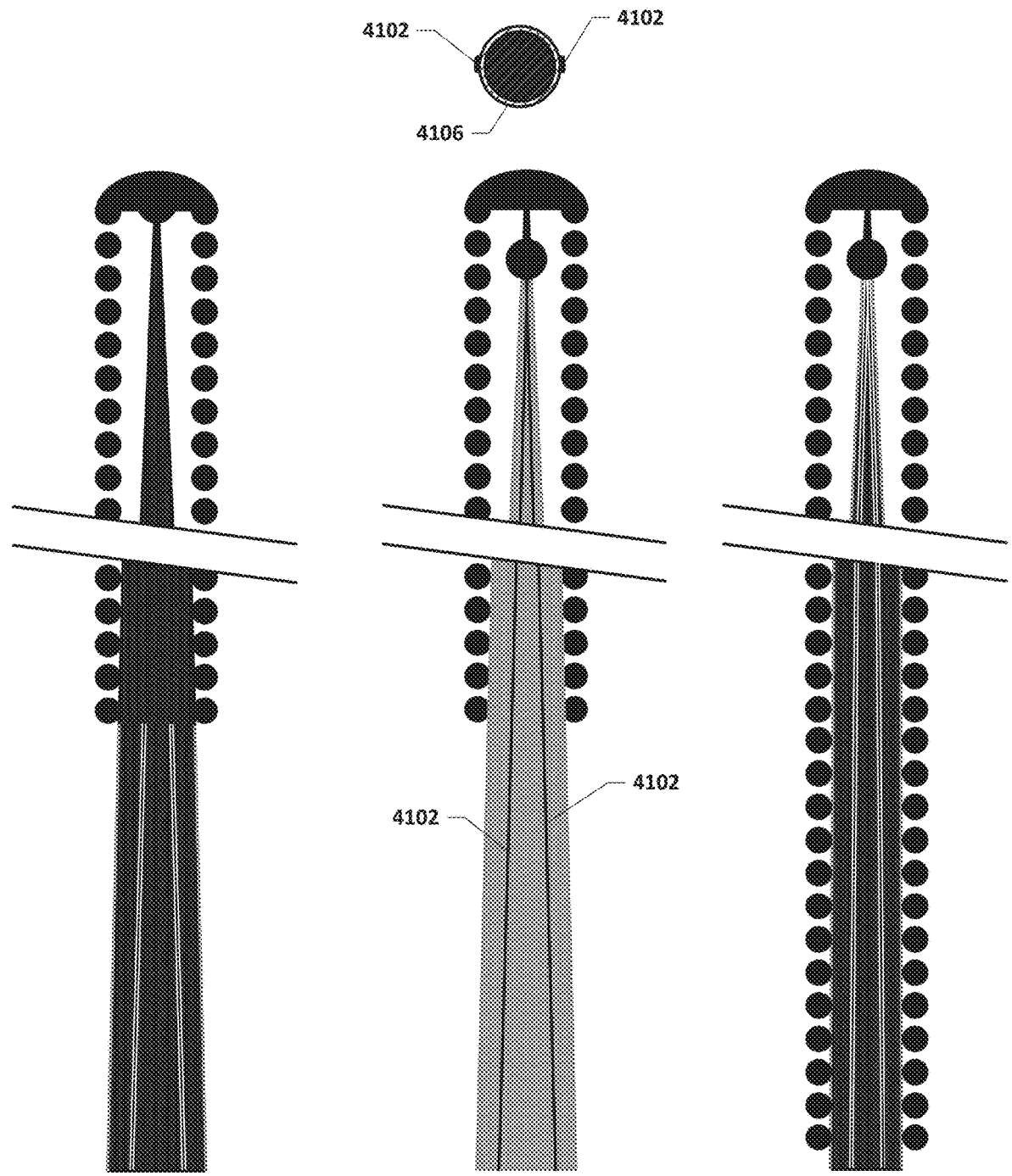

FIG. 41D shows an embodiment of the stylet/guidewire where the coil serves as the lead wire(s). In this embodiment, the lead wire(s) exit the core and are incorporated into the coil proximal to the sensor.

FIG. 41E shows an embodiment where lead(s) 4102 are made out of conductive ink. In this embodiment, the lead(s) may be on the outside of enclosure 4106. The ink may be deposited onto the enclosure. The conductive ink lead(s) may be sandwiched between two enclosures. Note that conductive ink may be used for any of the sensors, including conductance sensors, thermocouples, ECG, sensors, etc., and may be printed on the stylet and/or catheter and/or conduit, or may be printed on a flexible circuit and wrapped around, or applied to, the device.

FIG. 41F shows an embodiment of the stylet/guidewire where the coil exists over the entire length, or substantially the entire length, of the stylet/guidewire.

FIG. 42A shows an embodiment of the stylet/guidewire where lead(s) 4102 also serve as stiffener(s). The lead(s) may be encapsulated in enclosure 4106 and connect to sensor 2516. Additional stiffness may be added to this embodiment by using thicker leads, thicker/stiffer enclosure, for example, metal braid or coil or filament reinforced polyimide or polymer tubing etc. Alternatively, the gap between the enclosure and the leads may be filled with epoxy or adhesive. The leads may be welded or bonded to each other or to the enclosure. The enclosure may be co-extruded with one or more of the insulation layers of the lead(s), as shown in FIG. 42B. Thermoset polymers and/or metals may be used in the enclosure, insulation and/or leads. Each lead may include an insulation layer or only one lead may have an insulation layer or neither lead may include an insulation layer, for example in the embodiments where adhesive or epoxy is used to stiffen the stylet. In such embodiment, the lead diameter, cross-section design, and material may be designed to match desired stiffness of the stiffener. One or more of the leads may be spiral, coiled, or braided to achieve desired stiffener mechanical properties.

FIG. 42C shows the embodiment shown in FIG. 42A with the addition of a coil.

Any of the guidewires/styli disclosed herein may be used with any of the embodiments disclosed herein including any of the conduit embodiments.

Where "sensor" or "sensor" is used herein, other types of sensors may be used, including any measurable parameter including temperature, opacity, light reflectivity, sound reflectivity, density, viscosity, ability to absorb light, ability to absorb sound, pressure etc.

Figure 43:
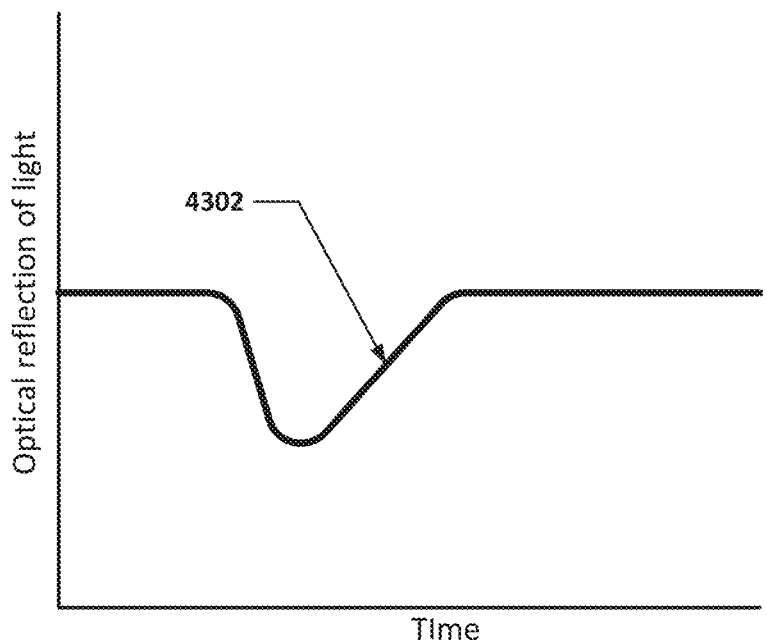
FIG. 43 shows data from an embodiment of the vascular catheter navigation device which uses optical reflection.

FIG. 43 shows that an optical signal can provide information on direction of blood flow and other blood flow parameters. In this embodiment, the medium is light and the parameter measured is light intensity and/or reflected light. Curve 4302 represents a measurement of reflected light over time in a blood vessel where blood flow is toward the device.

Figure 44:
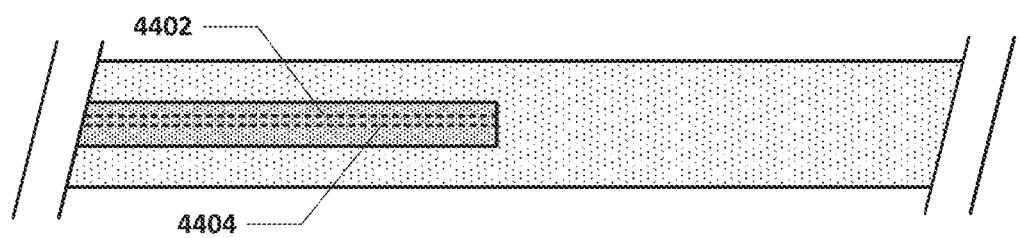
FIG. 44 shows an embodiment of the vascular catheter navigation device which uses optical reflection.

FIG. 44 shows an embodiment of a device which uses optical sensors. Fiber optic cables 4402 and 4404 can be used for transmission and detection of light. One cable may be used to introduce the medium (light) and the other cable serves as a sensor for a parameter of the medium (light intensity/wavelength). A detector and emitter combination can be used or an optical detector can be used without an emitter, requiring only one fiber. In some embodiments, light at particular wavelengths may be used. For example, red light of approximately 620 nm to 750 nm may be emitted, which is reflected more by red blood cells than by saline, or saline diluted blood. Thus a response can indicate a flow direction or characteristic. This same embodiment can be enabled more broadly with other types of visible light of about 350 nm-800 nm and near infrared light between about 400 and 1400 nm. This embodiment can be achieved with detector and/or emitters that are located at the point of measurement and potentially used in combination with a flex circuit. The optical measuring embodiment can also be used with the use of fiber optics (plastic, glass or other,) or light pipes where the actual detector and emitter are located in the controller and the light pipe or fiber optic communicates information collected at or near the catheter tip with the controller located outside the patient. This can be performed with fiber optic lines which are about 0.1 mm to about 0.5 mm in diameter or about 0.5 mm to about 4 mm in diameter. The fiber optic cable(s) may have an insulated coating. In some embodiments, a single optical fiber may be used.

Figure 45:
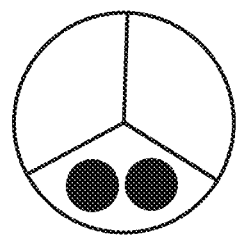
FIGS. 45 and 46 show a triple lumen device and a double lumen device respectively, with 2 fiber optic cables.
Figure 46:
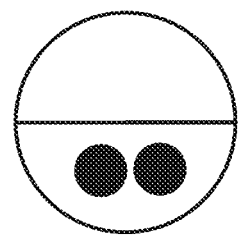

FIGS. 45 and 46 show a triple lumen device and a double lumen device respectively, with 2 fiber optic cables.

Figure 47:
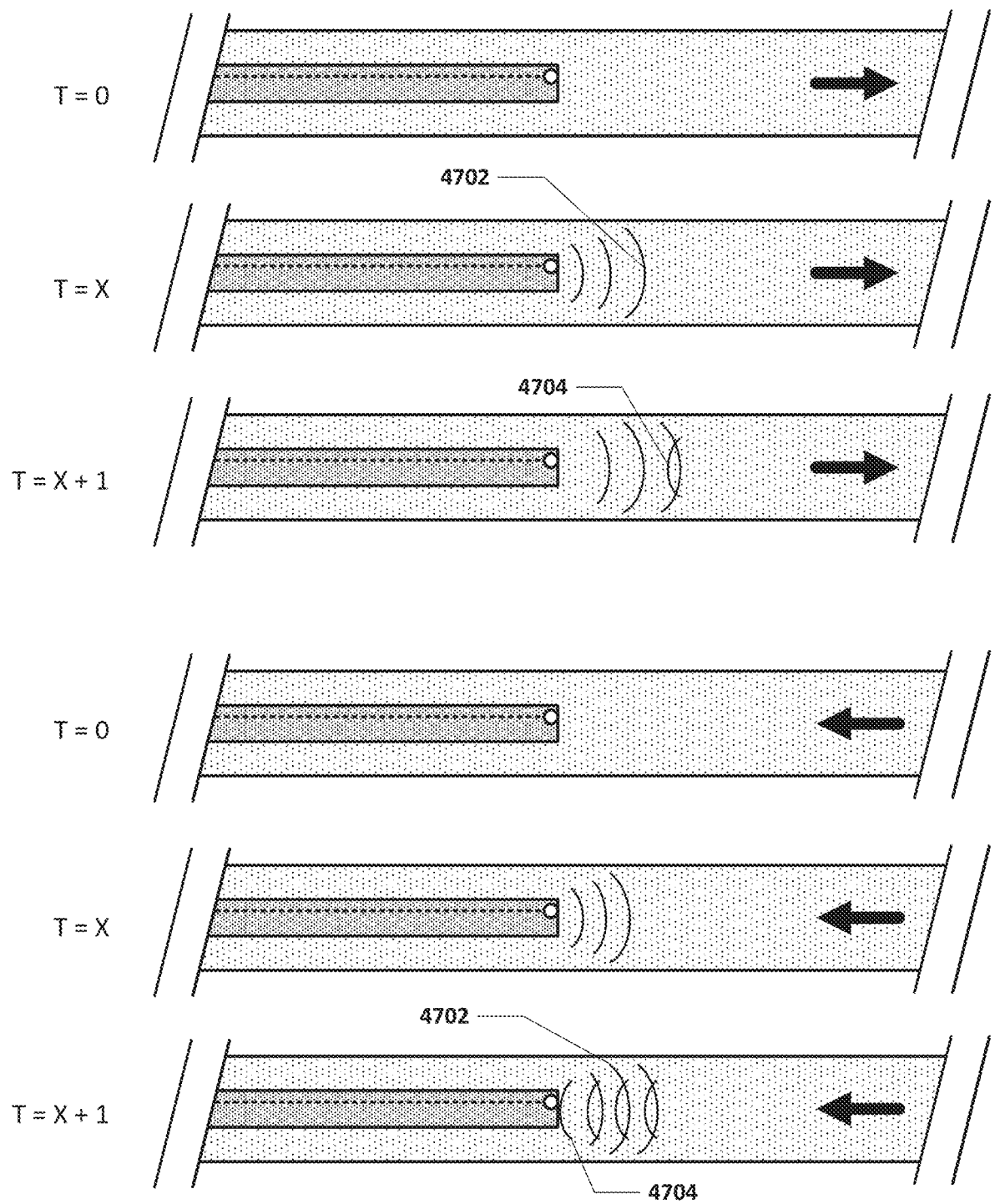
FIG. 47 shows an embodiment which uses sonar and sound waves to detect blood direction.

FIG. 47 shows an embodiment which uses sonar and/or sound waves to detect blood direction. In this embodiment, the medium introduced is sound and the parameter measured by sensors is reflected sound intensity and/or wavelengths. Sound is introduced via the device resulting in sound waves 4702 transmitted into the blood vessel. Some sound waves will be reflected back as reflected sound waves 4704 and can be measured by a sensor, such as a microphone, on the device.

Figure 48:
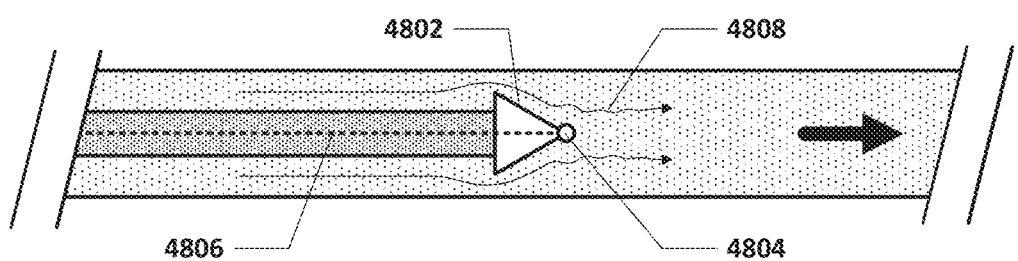
FIGS. 48 and 49 show an embodiment which uses one or more pressure sensors, with the aid of a turbulence inducer, to determine directionality of flow.
Figure 49:
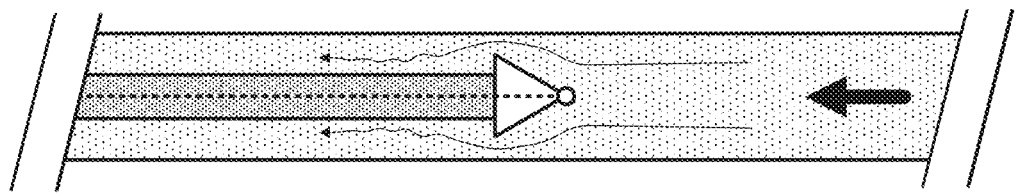

FIGS. 48 and 49 show an embodiment which uses one or more pressure sensors, with the aid of a turbulence inducer, to determine directionality of flow. A single pressure sensor 4804 or multiple pressure sensors can be used to detect the direction of flow with respect to the catheter or pressure sensor. This embodiment can include mechanism 4802 that induce turbulent flow 4808 to create different pressures at the reading location depending on if the flow disruption feature is upstream or downstream of the pressure sensor. Pressure data measured by pressure sensor 4804 is communicated to the controller (not shown) via connector 4806. This turbulence inducer can be included on the stylet and deployed much like an umbrella and then retracted. This turbulence inducer can be deployed and pushed through the vasculature as the device approaches the heart, or the turbulence inducer could be deployed at specific times when the location of the device needs to be determined. This could either be at a predetermined intervals, for example, about every 3 seconds (or ranging from 1 second to 5 seconds) or simply deployed whenever the operator would like to take a measurement. Alternatively, the turbulence inducer may be small enough so that it may be permanently deployed.

Figure 50:
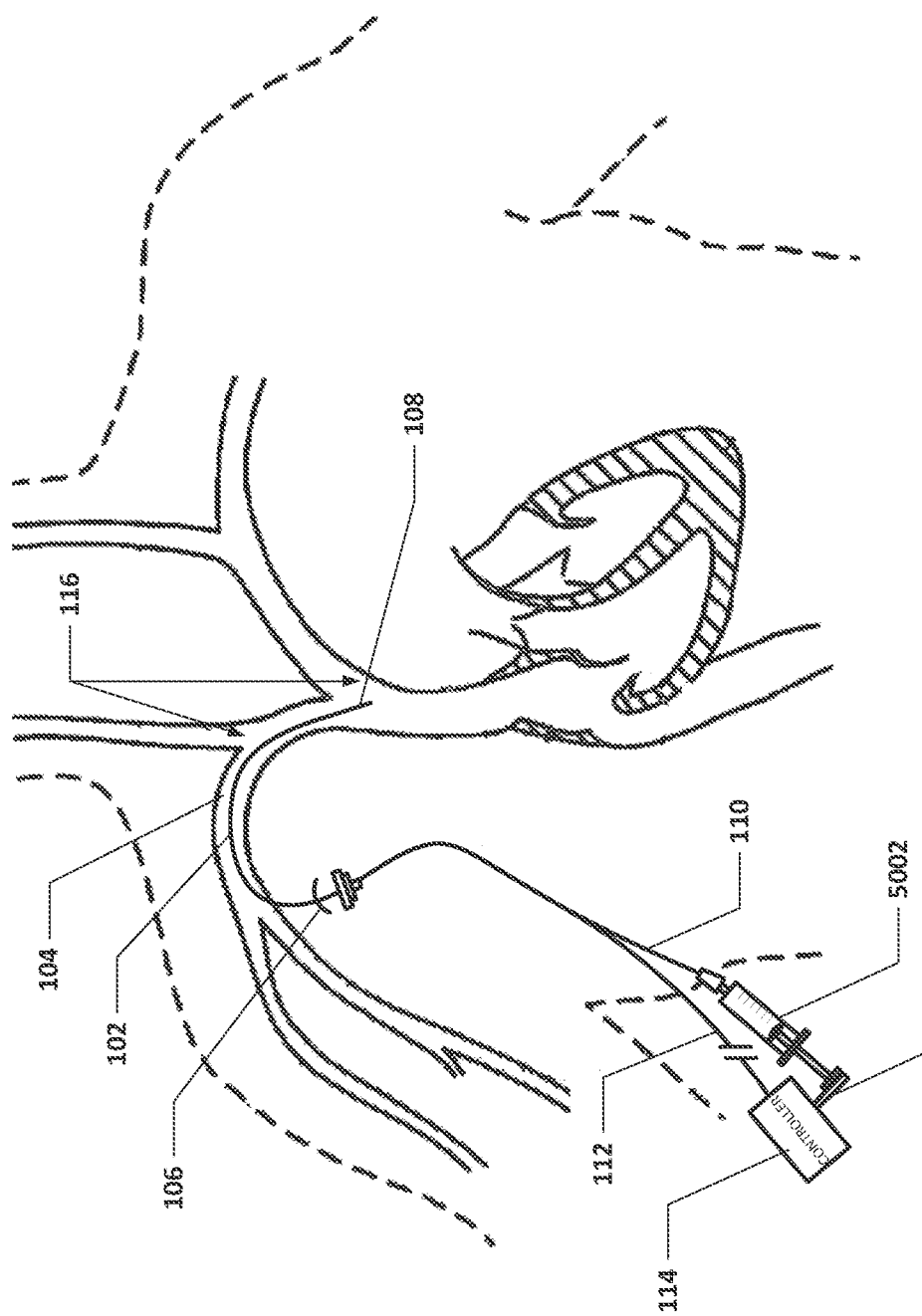
FIG. 50 shows an embodiment which includes a controller and a medium introduction mechanism.

FIG. 50 shows an embodiment which includes controller 114 and a medium introduction mechanism 5002 controlled by the controller via lever or mechanism 5004. The medium introduction mechanism may be a syringe containing saline or other fluid and mechanism 5004 may be a lever controlled by a motor within the controller. Alternatively, the controller may be remote from the medium introduction mechanism. The media introduction mechanism may alternatively be manually driven. The controller may be at the patient's bedside or remote. The controller may provide real time feedback if there are any changes of safety issues. It may be used standard PICC, subclavian, and intra jugular catheters, central catheters, regardless of brand.

Controller

The controller may control delivery of the medium and detection of the medium parameter in the blood flow. In addition the controller will receive information from the one or more sensors and interpret the information to assess the location, relative location, and/or hazard zones within the vasculature. The sensor signals are communicated, via a wire, fiber optic cable, or other means, back to the controller where the signal(s) are analyzed based on the measured parameter, parameter profile, parameter of more than one sensor, or change in parameter over time and/or distance. For example, the controller can determine whether the distal end of the vascular catheter navigation device is in an artery instead of a vein, based on magnitude and direction of blood flow, and/or other flow parameters, near the vascular catheter navigation device. For example, if the controller determines that the distal end of the vascular catheter navigation device is in an artery instead of a vein, a specific identifying signal may sound, including an audible, visual signal etc., instructing the user to remove the vascular catheter navigation device, and any other device, such as sheaths, catheters etc., and apply pressure to the blood vessel. For example, instructions for advancing, retreating, redirecting, stopping or removing, the vascular catheter navigation device may be displayed by the controller on a screen connected to the controller either. The connection may be wired or wireless and the screen may be local or remote. The signal from the controller may be transmitted over Bluetooth, or other wireless protocol, to a computer such as a laptop, tablet, phone, watch, or other peripheral device.

The controller may control introduction of medium, including injection of a temperature controlled solution, such as saline, introduction of sound, introduction of light, introduction of a fluid containing a level of a parameter, etc. Temperature controlled may mean a temperature which is different than body temperature.

Injection Mechanism and Fluid Properties

The infusion drip, bolus, droplet, stream, etc., used to detect catheter location may have specific parameters. The infusion may be a drip or it may be a stream. The preferred intermittent volume size (drip, drop, bolus, intermittent stream) is between about 0.5 cc to about 3 cc, but can range between about 0.1 cc and about 10 cc. Alternatively the volume may range from about 0.5 cc to about 1 cc. Alternatively the volume may range from about 0.5 cc to about 2 cc.

The preferred drip interval may be between about every 0.5 second to about every 4 seconds to a broader range of about every 0.25 seconds to about every 10 seconds. Where the infusion is a continuous stream, the preferred flow rate is about 4 cc/minute but may range from about 0.25 cc/minute to about 15 cc/minute or from about 0.1 cc/minute to about 30 cc/minute or from about 0.1 cc/minute to about 60 cc/minute.

The pressure applied to the injection mechanism (syringe, for example) for injection may be around 3 psi but may range from about 1 psi to about 5 psi, or the range may be from about 0.1 psi to around 200 psi.

The controller may control an injection device, or volumetric displacing device, such as a syringe, so that the injection device introduces a controlled volume and/or rate of fluid into the catheter or stylet/guidewire. The fixed volume and/or rate of fluid may be at a controlled temperature, either above or below that of blood (approximately 37 degrees Celsius), or at a known temperature which is measured. The injection device may inject a controlled volume and/or rate of fluid at predetermined intervals, or other intervals, or continuously. The controlled volume and/or rate of fluid may remain the same throughout a procedure, or the volume and/or rate may change depending on the patient, the location of the catheter/system within the vasculature, etc.

For example, the volume and/or rate of fluid injected may increase as the tip of the catheter gets closer to the heart. The volume and/or rate may be different for different sized vascular catheters or different sized lumens of vascular catheters, for example in catheters with multiple lumens.

The volume and/or rate of fluid injected may be controlled by a lead screw, cam, linear actuator motor, peristaltic pump, etc. The force of the injection requirements may also be controlled and/or monitored. For example, if an unusually high force is required to inject the fluid, an alert may tell the user that a possible catheter blockage situation exists, including a catheter kink, a blood clot, the catheter tip up against a vessel wall, or within a small vessel, or other catheter patency situation. Higher or lower force injections may be used in different areas of the anatomy, or to confirm location within the anatomy. For example, a higher forced injection of a smaller volume and/or rate may provide different temperature curve information than a lower force, higher volume and/or rate injection. Small volume injections at a higher frequency may provide different information than larger volume injections at a lower frequency, etc.

The fluid injector may also be configured to withdraw fluid through the catheter/stylet/guidewire to determine injection lumen/tip patency. The controller may assess force to withdraw fluid to determine that fluid is flowing freely through the catheter/stylet/guidewire. If fluid is not flowing freely, a patency alert may alert the user. Alternatively the controller may have a sensor which senses the existence of blood in the system when the injector withdraws fluid through the catheter/stylet/guidewire. This may be done optically or otherwise.

Figure 51:
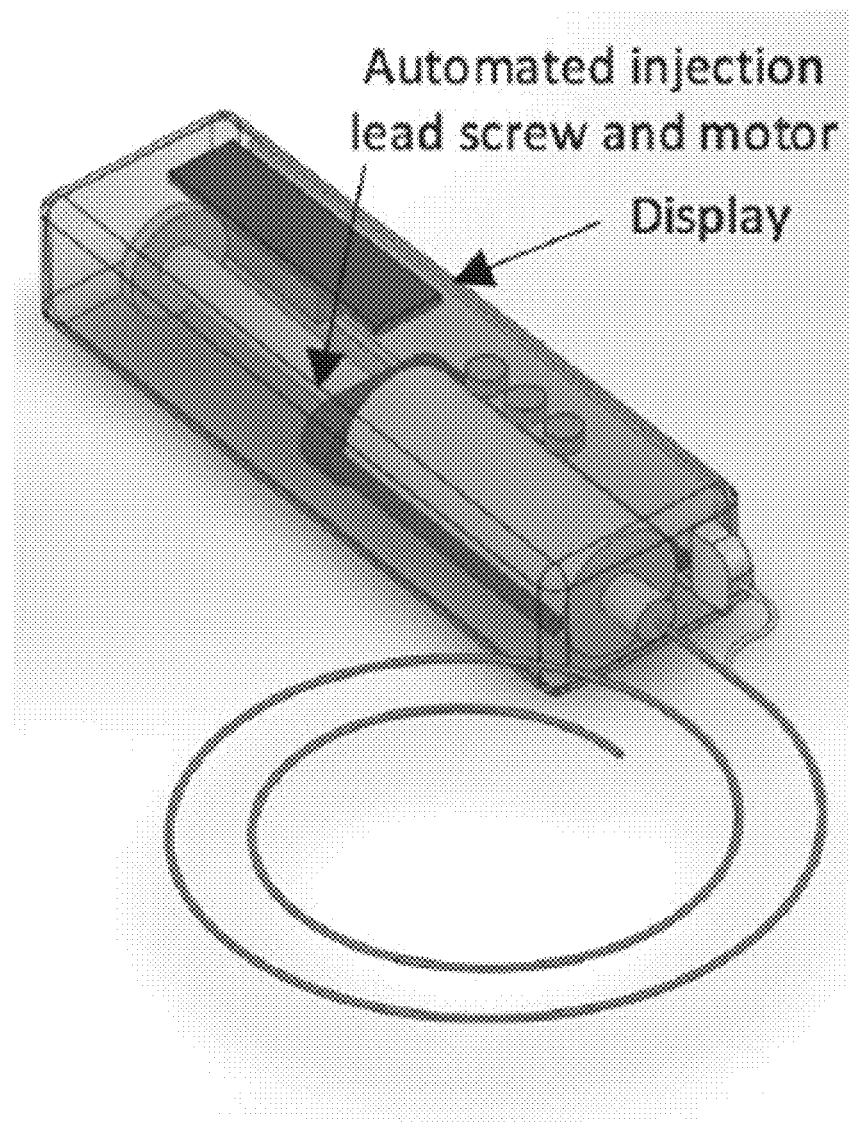
FIG. 51 shows an embodiment of the injection mechanism.

An embodiment of the injection mechanism is shown in FIG. 51. This embodiment may include an automated injection system for the cartridge/syringe/reservoir which may be a motor driving lead screw. The controller controls the infusion delivery parameters, including pressure, volume, frequency, rate, etc. The controller may also control the GUI. The buttons, shown in FIG. 51 may turn the device on and off, purge the catheter of air prior to insertion, and/or may stop operation of the device in case of a sensed problem situation. The unit may be fully disposable, partially disposable or non-disposable, and may reside in the sterile field or the unsterile field during the procedure.

The system may come packaged with a prefilled injection device, or a fillable injection device. Saline may be used as the fluid. Contrast medium may be used (which is a higher viscosity than saline). Fluids of differing viscosity may be used, or fluids may be mixed (such as contrast medium and saline) to achieve a desired viscosity or other desired properties. Fluids of different surface tension, different specific heat capacity, different acidity or other different attributes may be used. Fluids with properties that differ from those of blood will provide different temperature, or parameter, curves and therefor provide different information regarding the location of the catheter/guidewire/stylet tip in the vasculature. Some fluids may be soluble in blood and others less soluble. Since the injection fluid is injected into the blood stream, the fluid used will preferably be biocompatible.

Additives may be added to the injection fluid for different results. For example, salts, such as NaCl may be added. Different salts or other additives may improve an ECG signal in embodiments that include an ECG electrode. A different fluid (liquid or gas) may be introduced with the primary fluid to modify the fluid properties. For example, a biocompatible liquid or gas may be "bubbled" into saline.

More than one injection fluid may be used, either mixed and injected through the same lumen and exit port(s), or injected separately, through different lumens and different exit ports. One or more of the injection fluids may include a drug or medication.

A user interface controlled by the controller may include a display, alerts (auditory, visible, lights, vibrations etc.) and other information. The user interface may include a display of the anatomy with a virtual reality indicator of the location of the catheter/guidewire/stylet tip within the anatomy. For example, the display may be an image of the human vascular system, and a moving indicator, such as a light, may show where within the anatomy the catheter/guidewire/stylet tip is. The display may be actual size, and possibly even projected upon the patient, or it may be a smaller or larger size, for example, displayed on the controller, a tablet, or projected up on the wall. The controller and/or display may include a computer, laptop, tablet, mobile phone, virtual reality/augmented reality glasses, etc.

The system may be fully disposable. A fully disposable system primary package includes: syringe, syringe pump, the syringe filled with the fluid of choice, a controller, a user interface which can exist as any combination of display, alert, and lights, catheter, stylet/guidewire, and introduction mechanism. All of these elements may be fully disposable. By doing so, the chance of infection will be reduced.

Another embodiment includes all of the items listed above where the display is non-disposable. The display may be within the non-sterile field and communicate via cable or a wireless communications protocol such as Bluetooth. Alternatively, the display may be within the sterile field using a wired or wireless connection. Additionally/alternatively, the display may be projected on glasses—either virtual reality or augmented reality glasses. The glasses may be within the sterile or non-sterile field. Additionally, a projector may project the display on a surface of choice and the projector may be in sterile or non-sterile field.

Another embodiment consists of two subsystems. The disposable elements may include catheter, stylet/guidewire, and a fluid filled volume displacing device, such as a syringe. The non-disposable elements may include a controller in a housing, mechanics/motors to depress the lead screw on the syringe/cartridge, display, audio, and visual elements, as well as user interaction buttons, etc.

Any of the catheter/stylet/guidewire placement and/or patency techniques disclosed herein may be used while placing the device in the vasculature, as well as after placement, to determine that the device has not significantly strayed from its placement location over time.

Any of the embodiments disclosed herein may be used with any type of central vascular catheter including central venous lines, clavicle lines, midline, etc. In addition, any of the embodiments disclosed herein may be used with peripheral vascular catheters, dialysis catheters, and cardiac catheters including catheters used for: coronary arteries, patent foramen ovale, atrial septal defect, etc. Any of the embodiments disclosed herein may be used with any type of urinary catheters. Similar technology may be used in underwater navigation, mining, oil and gas exportation, utility fabrication or repair, transportation infrastructure fabrication and repair, etc.

Other technologies may also be used in conjunction with the sensor readings from the vascular catheter. For example ECG readings, ultrasound readings, Doppler readings, x-ray readings, inductive current technology, pressure readings, etc. Some, all or no readings may be augmented via a turbulence inducer. These, and other, other types of readings may be used in conjunction with the sensor readings by the controller to determine the location of the vascular catheter navigation device distal tip. Specific modalities may be better at identifying specific vascular landmarks or conditions.

For example, any of the conductive components of the vascular navigation device may be used as an ECG lead. Another ECG lead may be placed on the patient's skin. For example, the guidewire stylet stiffener, coil, enclosure, thermocouple leads, sensor leads, thermocouple, endcap, conduit, etc. may be used as an ECG lead or leads. Alternatively, a separate ECG lead may be added to the system.

Embodiments of the vascular navigation device may include the ability to measure cardiac output or cardiac flow rate. The parameter vs. time/location curve may be analyzed by the controller to determine cardiac output in addition to vascular location, either simultaneously, or at separate times. Cardiac output may also be used to help establish the location of the vascular navigation device within the vasculature.

Embodiments of the vascular navigation device may include the ability to measure blood flow rate in other areas of the body/vasculature.

Several embodiments have been disclosed herein. It will be understood that any of the features of any of the embodiments may be combined with any embodiment.

Some embodiments of the vascular access or vascular navigation device may be used in other applications. For example, the controller of the device may be equipped with logic to navigate, identify, and assess the health of various vascular or other anatomies. For example, some embodiments may be configured to identify the location of valves within the peripheral vascular (for example, venous) system. Valve location may be identified based on the flow characteristics near and within a valve. Valve health may be assessed based on flow characteristics near and within a valve. Valve function may be assessed based on flow characteristics near and within a valve. Valve closure may be assessed based on flow characteristics near and within a valve. Vascular flow characteristics may be used by the system to navigate near to, within, and/or past valves. Some embodiments of the vascular navigation device may be used in conjunction with treatment procedures. For example, the system may be used to aid in placement of valve prosthetics, valve repair etc. The system may be used to assess the success of such procedures, based on flow characteristics, placement location etc. The system may also be used to navigate to vessel stenting locations, and to assess the function of a vessel before and after a procedure. The system may be used to assess the function and/or location and/or health of a prosthetic (stent, valve etc.) before and after its placement.

In some embodiments, the system may be used to diagnose a stenosis, blockage, narrowings or disease of a blood vessel based on flow characteristics. The system may be used to classify a stenosis, blockage, narrowings or disease of a blood vessel based on flow characteristics. The system may be used to identify the location and quantity of spinal fluid leak.

In some embodiments of the system, the vascular system is accessed peripherally, via a leg, arm, groin, etc.

Some embodiments of the system may be used to diagnose other diseases or health based on flow characteristics of vessels or other organs (such as the bladder, lungs, etc.)

Some embodiments of the system may be used to assess health of, and navigate through, other vessels such as those in the brain. For example, the system may be used to identify, navigate to and assess the health of, aneurysms, blockages, narrowings, stenosis with the brain and elsewhere in the body.

Embodiments of the system may be used for any interventional radiology procedure including Angiography, Arteriovenous Malformations (AVM), Balloon Angioplasty, Biliary Drainage and Stenting, Bleeding Internally, Central Venous Access, Chemoembolization, Embolization, Gastrostomy Tube, Hemodialysis Access Maintenance, High Blood Pressure, Infection and Abscess Drainage, Needle Biopsy, Radiofrequency Ablation, Stent, Stent Graft, Thrombolysis, TIPS (Transjugular Intrahepatic Portosystemic Shunt), Urinary Tract Obstruction, Uterine Artery Embolization, Uterine Fibroid Embolization, Varicocele Embolization, Varicose Vein Treatment, Vena Cava Filter, Vertebroplasty, Deep Vein Thrombosis, etc.

Some embodiments of the system may be used to identify blood flow direction, speed, flow characteristics, etc. This may be useful not only for navigation of the venous system, but also in assessing venous or arterial flow conditions that are useful for identifying heart disease, chronic venous disorder, venous outflow obstructions, etc.

Some embodiments of the system may be used to identify the change in flow characteristics of the blood as it responds to drugs such blood thinners (heparin, etc.) acutely or over time. For example, blood thinness, viscosity, or other properties may be assessed based on the flow characteristics.

Some embodiments of the multi sensor technology may also be included in a permanent implant within the body rather than used as a temporary device. It may be used to measure the performance or health of the cardiovascular system over time, measure post intervention performance over time, etc. This type of intervention may be surgical only, such as when used in a bypass procedure, and may also include monitoring the results and/or performance, and/or success of interventions such as mechanical valves, stents, balloons, etc. It may also be used for the assessment of the need for interventions.

In any of the embodiments disclosed herein, in addition to or instead of measuring temperature of a fluid bolus or stream that is injected, the system may measure the electrical conductivity of a bolus or stream of fluid. As a stream or bolus of fluid fluctuates with various flow conditions and directions, variation in electrical conductivity can be detected. Additionally, fluid may be injected to optimize the electrical conductivity. For example, fluid containing one or more salts may be used to make the fluid more electrically conductive, or, for example, fluid which is less conductive than blood may be used, such as distilled water, or dextrose water.

This technology may also be used outside of the body on the surface of the skin in proximity to one or more veins. This may be done on the skin or just under the skin, across the skin or within the skin. For example, temperature sensors may be placed in several locations on top of the skin or vein. A heating or cooling event may be administered intravascularly to detect blockages, flow, or navigation requirements. Conversely, the heating and or cooling event may happen externally to the skin while the system senses the temperature intravascularly. Alternatively, pressure, or electrical conductivity may be used. Some embodiments may also detect flow characteristics, diagnose venous or arterial disease, challenges, and obstructions, in either acute or chronic events. Embodiments of the device on the surface of the body or vein may be a temporary assessment tool, or may be a more permanently worn biosensor such as a watch, ring, wristband, necklace, earing, contact lens, etc.

Example of Data Processing System

Figure 52:
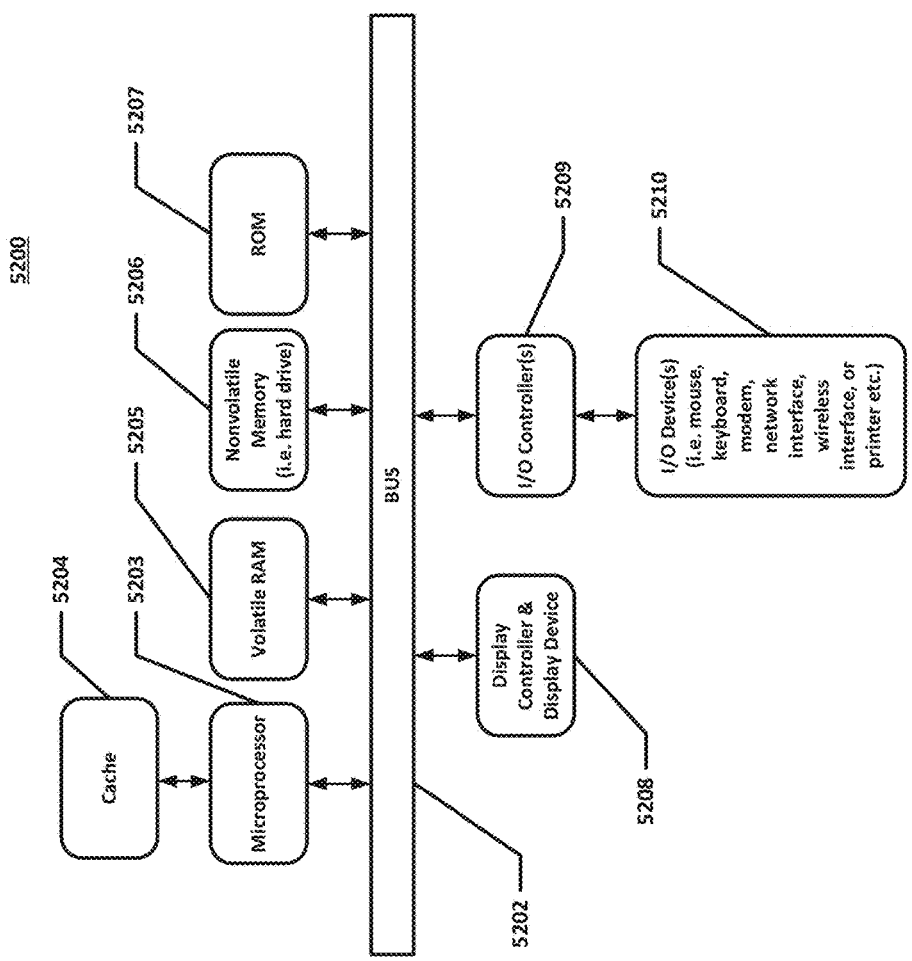
FIG. 52 is a block diagram of a data processing system, which may be used with any embodiments of the invention.

FIG. 52 is a block diagram of a data processing system, which may be used with any embodiment of the invention. For example, the system 5200 may be used as part of the controller. Note that while FIG. 52 illustrates various components of a computer system, it is not intended to represent any particular architecture or manner of interconnecting the components; as such details are not germane to the present invention. It will also be appreciated that network computers, handheld computers, mobile devices, tablets, cell phones and other data processing systems which have fewer components or perhaps more components may also be used with the present invention.

As shown in FIG. 52, the computer system 5200, which is a form of a data processing system, includes a bus or interconnect 5202 which is coupled to one or more microprocessors 5203 and a ROM 5207, a volatile RAM 5205, and a non-volatile memory 5206. The microprocessor 5203 is coupled to cache memory 5204. The bus 5202 interconnects these various components together and also interconnects these components 5203, 5207, 5205, and 5206 to a display controller and display device 5208, as well as to input/output (I/O) devices 5210, which may be mice, keyboards, modems, network interfaces, printers, and other devices which are well-known in the art.

Typically, the input/output devices 5210 are coupled to the system through input/output controllers 5209. The volatile RAM 5205 is typically implemented as dynamic RAM (DRAM) which requires power continuously in order to refresh or maintain the data in the memory. The non-volatile memory 5206 is typically a magnetic hard drive, a magnetic optical drive, an optical drive, or a DVD RAM or other type of memory system which maintains data even after power is removed from the system. Typically, the non-volatile memory will also be a random access memory, although this is not required.

While FIG. 52 shows that the non-volatile memory is a local device coupled directly to the rest of the components in the data processing system, the present invention may utilize a non-volatile memory which is remote from the system; such as, a network storage device which is coupled to the data processing system through a network interface such as a modem or Ethernet interface. The bus 5202 may include one or more buses connected to each other through various bridges, controllers, and/or adapters, as is well-known in the art. In one embodiment, the I/O controller 5209 includes a USB (Universal Serial Bus) adapter for controlling USB peripherals. Alternatively, I/O controller 5209 may include IEEE-1394 adapter, also known as FireWire adapter, for controlling FireWire devices, SPI (serial peripheral interface), I2C (inter-integrated circuit) or UART (universal asynchronous receiver/transmitter), or any other suitable technology. Wireless communication protocols may include Wi-Fi, Bluetooth, ZigBee, near-field, cellular and other protocols.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The techniques shown in the Figures can be implemented using code and data stored and executed on one or more electronic devices. Such electronic devices store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The processes or methods depicted in the preceding Figs may be performed by processing logic that comprises hardware (e.g. circuitry, dedicated logic, etc.), firmware, software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

As mentioned herein, vascular location using fluid injection can also be determined through conductivity sensing, for example, where the sensor(s) include one or more electrodes. In these embodiments, the sensor(s), or electrode(s), measure the conductivity (or impedance) of the blood/medium mix, where the medium has a conductivity which is different than that of blood. For example the medium infused into the vessel may have a higher or lower conductivity than that of blood.

Salts are conductive, thus the salinity of the blood/medium mixture may be determined by the voltage drop across a pair of electrodes. For example, if a fluid that is less conductive than blood (such as a lower salinity saline solution (for example, 0.45% NaCl saline) or a solution without salt, such as H2O or a dextrose solution) is the medium which is introduced into the blood stream, a conductivity sensor can measure the presence of that fluid in the blood stream by measuring the conductivity of the blood/medium mixture within the blood flow. The measurement of conductivity over time/device position within the vessel can be used to determine laminar flow, turbulent flow, flow direction, etc. at the device tip or at the sensor(s) location. As a reference, the salinity of blood is around 0.9%.

Alternatively, a medium with a higher conductivity than that of blood may be used. For example, a 3% NaCl solution may be used to detect the fluid flow characteristics. In addition, a hypertonic solutions may increase the signal strength of measured ECG signals. All of the configurations described herein using temperature sensors or other sensors may alternatively use conductivity or impedance sensors. In some embodiments, the electrodes that serve as sensors may detect an ECG signal without an exterior (i.e. skin) ground electrode.

Figure 53:
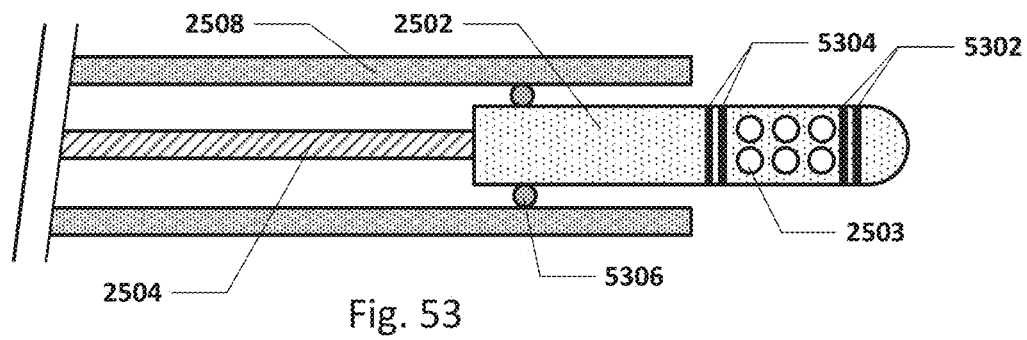
FIG. 53 shows an embodiment of the vascular catheter navigation device which includes sensors, or electrodes, and a diffuse exit port, for measuring conductivity.
Figure 54:
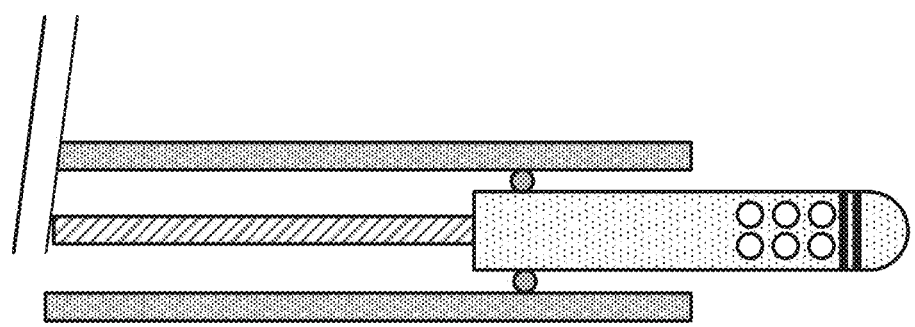
FIG. 54 shows an embodiment with one pair of electrode sensors, and a diffuse exit port.

FIG. 53 shows an embodiment of the vascular catheter navigation device which includes sensors, or electrodes, for measuring conductivity. Shown here are distal electrode pair 5302, proximal electrode pair 5304, fluid exit point 2503, conduit 5202, seal 5306, catheter 2508, and guidewire/stylet 2504. A single sensor may comprise a pair of electrodes. For example, distal electrode pair 5302 may represent a distal sensor and proximal electrode pair 5304 may represent a proximal sensor. Seal 5306 may provide an essentially fluid tight seal between the conduit and the catheter. Electrodes may be on the surface of the device, or may be solid discs in some embodiments. In some embodiments, fluid exit point 2503 may include multiple small openings in the conduit. The fluid exit point may be forward facing as shown in some embodiments herein, or side/laterally facing, as shown here. The multiple small openings allow for a more diffuse infusion of medium fluid, as opposed to a more directed stream which may occur with a single openings. Multiple openings may run essentially circumferentially (360 degrees) around the device or may exist less than essentially 360 degrees around the device. FIG. 53 shows an embodiment with 2 pairs of electrodes and a diffuse exit port. FIG. 54 shows an embodiment with only one pair of electrodes. In some embodiments, the sensor, or electrode pair, is close (between 0.05 mm and 1 mm) to the fluid exit port/holes as this increases the sensitivity of the sensor.

In embodiments which use conductivity or impedance to determine the location of the vascular navigation device, a current is applied to an electrode of a sensor and the conductivity or impedance of the blood/medium mixture between two electrodes is sensed by the second electrode of a sensor. The driving frequency of the signal may be around 10,000 Hz. Alternatively the driving frequency may be around 500 Hz to around 100,000 Hz. Alternatively the driving frequency may be higher than around 100,000 Hz. The sampling frequency may be around 50 Hz. Alternatively, the sampling frequency may be around 25 Hz to around 100 Hz. The sampling frequency may be fixed, or may be variable and may depend on the frequencies within the detected conductivity or impedance signal.

Figure 55:
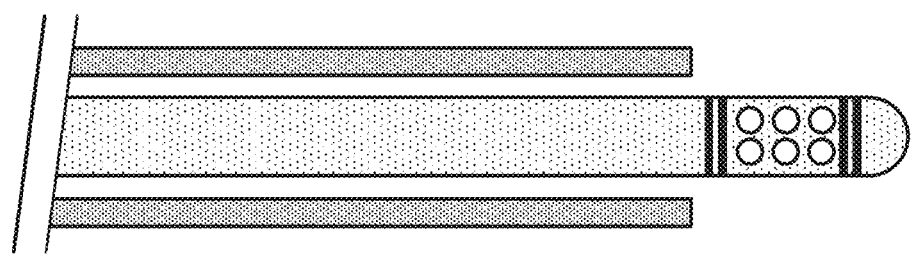
FIG. 55 shows an embodiment with a diffuse exit port, where the medium infusion lumen runs the length of the guidewire/stylet.

FIG. 55 shows an embodiment where the medium infusion lumen runs the length of the guidewire/stylet.

Figure 56:
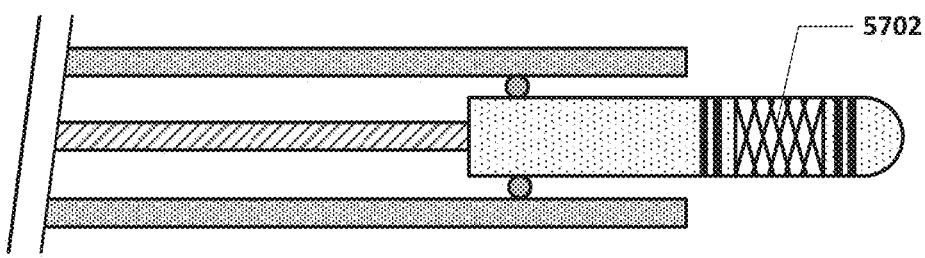
FIG. 56 shows an embodiment of the vascular catheter navigation device which includes a mesh or braid as a component of the diffuse fluid exit point.

FIG. 56 shows an embodiment of the vascular catheter navigation device which includes open mesh or braid 5702 as a component of the fluid exit point. The mesh/braid may encompass essentially 360 degrees of the conduit or may encompass less than essentially 360 degrees of the conduit. The mesh/braid may be metal, polymer or other suitable material.

Figure 57:
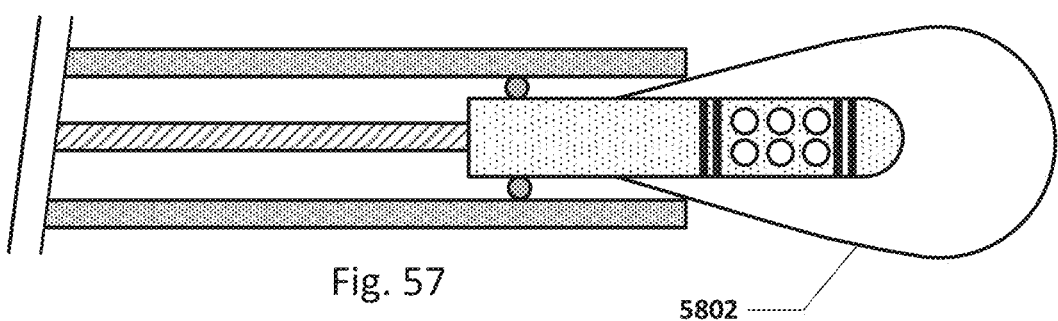
FIG. 57 shows an embodiment with a diffuse exit port and which includes a spacer.
Figure 58:
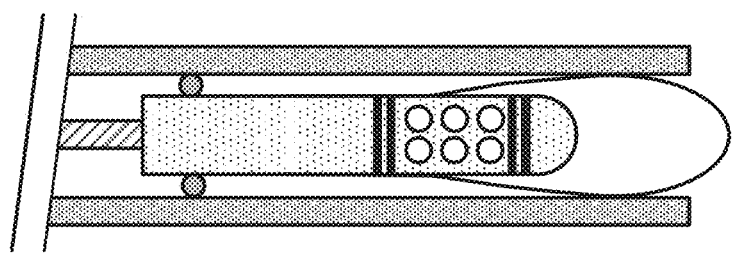
FIG. 58 shows an embodiment with a diffuse exit port and which includes a spacer.

FIGS. 57 and 58 show an embodiment which includes spacer 5802 which maintains a space between the vessel wall and the electrode sensor(s) so that the sensors don't directly touch the vessel wall. The spacer may be a simple wire loop as shown here, or may have 2 or more loops, like a whisk, or may be of other suitable configurations. Preferably, the spacer may be compressed for introduction into and removal from the vessel. For example, the spacer may be compressed by pulling the guidewire/stylet into the catheter as shown in FIG. 58.

Figure 59A:
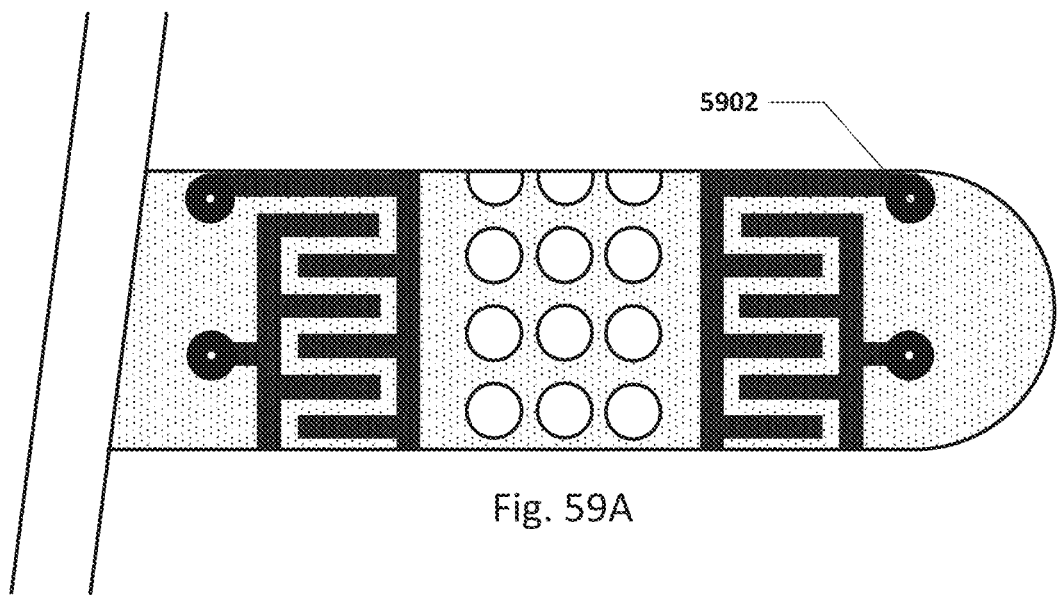
FIGS. 59A and 59B show some possible embodiments of electrode pairs.
Figure 59B:
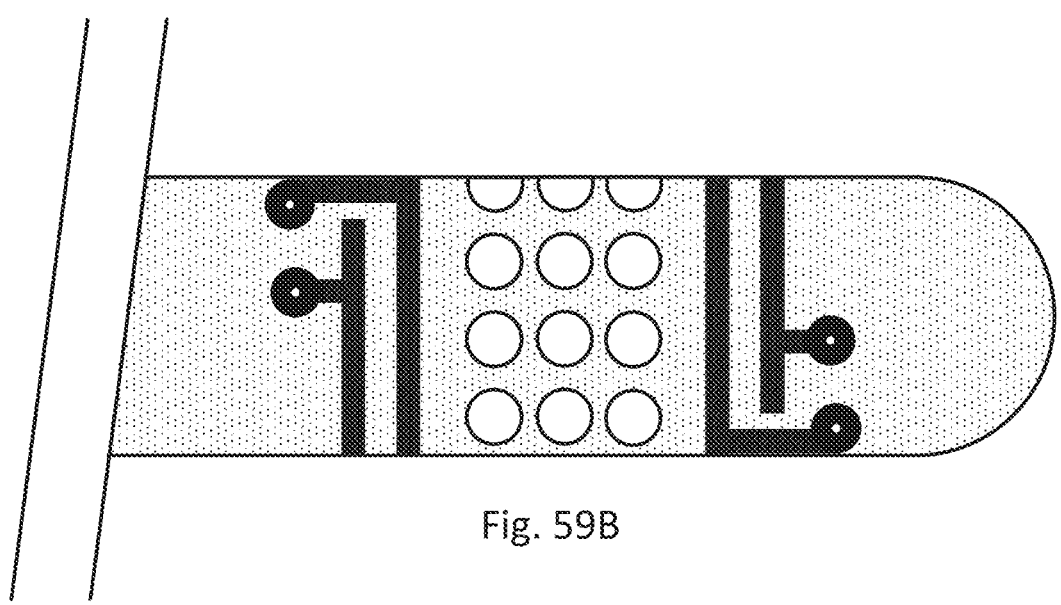

FIGS. 59A and 59B show some possible embodiments of the electrode pairs at the distal end of the device. A serpentine or other suitable pattern is shown in FIG. 59A to increase the surface area of the two electrodes in an electrode pair. The distance between the electrodes within an electrode pair may also be altered to optimize the signal. Connectors 5902 are used to connect the electrodes to wires/leads, or other conduction mechanisms within the device, back to the controller. For example, connectors 5902 may connect to a wire underlying the electrodes which runs the length of the device back to the controller. Alternatively, connectors 5902 may connect to tracings on the inside or the outside of the device.

Disclosed herein are various embodiments of the vascular catheter navigation device which rely on injecting an injectate, or medium, into the blood stream, where the injectate has a parameter, the value of which differs from that of blood. For example, the injectate may have a different temperature or conductance or impedance than the temperature, conductance or impedance of blood. Because these embodiments are sensing and analyzing the injectate parameter to determine the flow characteristics of the blood within a vessel, it is important that the flow characteristics of the injectate be repeatable and meaningful. Different injectate exit port designs result in different injectate flow characteristics, and impact the data collected by and analyzed by the controller.

It is also desirable that the injectate flow in proximity to the sensors on the device so that the sensors can measure the changes in the sensed parameter. It may be desirable for the injectate flow to surround the navigation device essentially 360 degrees or as close to 360 degrees as possible, particularly in laminar, or less turbulent blood flow.

To achieve this, some embodiments include an injectate exit or port which diffuses the exit flow of injectate, to control and/or minimize the injectate exit velocity. These types of injectate port exit designs are termed "diffuse" exit port designs. Such a diffusing exit port may incorporate multiple openings or a mesh, similar to those shown in FIGS. 53-59B. To further illustrate this type of fluid exit point or port, please refer to FIGS. 60A-C.

Figure 60A:
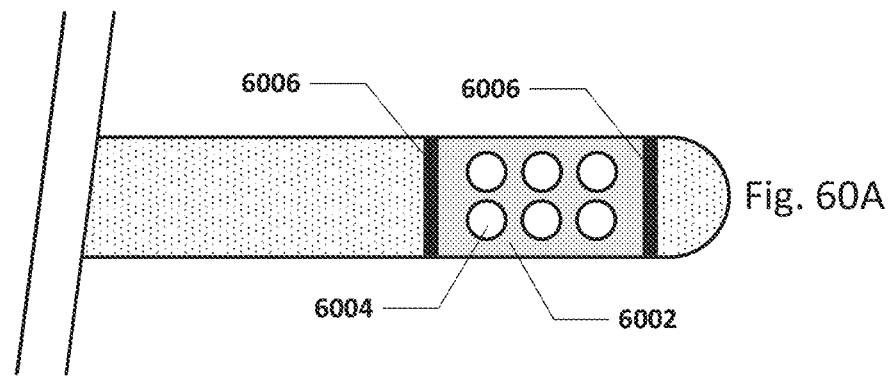
FIG. 60A shows the distal end of a vascular catheter navigation device with a diffuse exit port area.
Figure 60B:
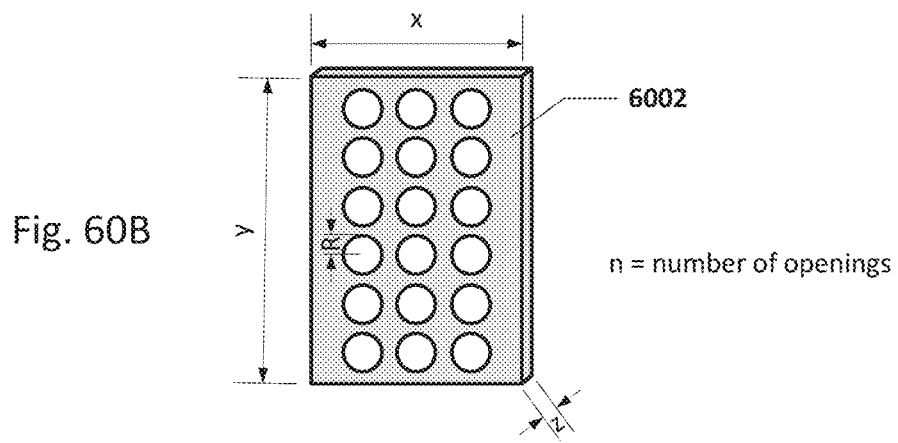
FIG. 60B shows a porous sheet used to manufacture an embodiment of the catheter with a diffuse exit port area.

FIG. 60A shows the distal end of a vascular catheter navigation device with diffuse exit port area 6002. The exit port includes openings 6004 and in this embodiment, is between two sensors 6006, each of which may be a pair of electrodes. The exit port 6002 shown in this embodiment is manufactured by wrapping a thin perforated sheet around an opening in the device, creating the diffuse exit port. An example of the sheet is shown in FIG. 60B. The sheet may be made from polyimide or any other suitable thin and strong material, such as a polymer, a metal, etc.

Figure 60C:
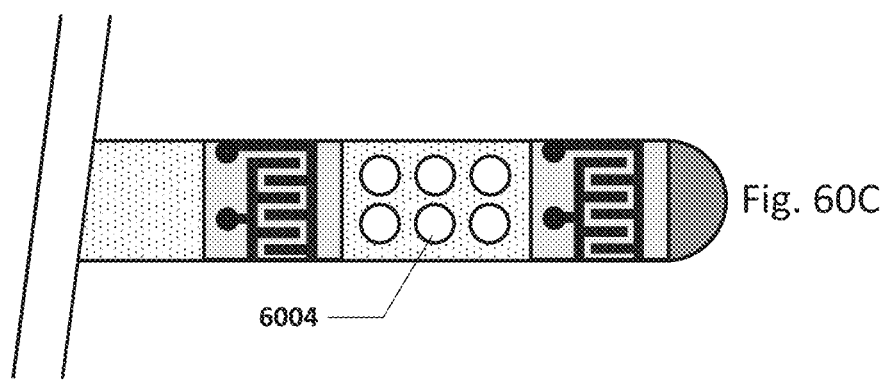
FIG. 60C shows the distal end of a vascular catheter navigation device with a diffuse exit port area.

FIG. 60C shows an embodiment where openings 6004 are incorporated into the surface of a conduit. The conduit may run through essentially the entire length of the catheter inner lumen or a portion of the catheter inner lumen. For example, the vascular access device may include an elongated polyimide, or other material, tube with openings 6004 cut into the wall of the tube near the distal end of the tube. Sensors may be sheets which are wrapped around the tube as shown here, or may be other types of sensors as disclosed herein. The sensor leads (not shown) may be wires or tracings on either the inside or outside of the tube.

By showing the flattened diffuse exit port we can see that the exit port has a surface area, X times Y. It also has a percentage of opening area which is the surface area of the sheet minus the total surface area of the openings. If the openings are circular, the area of each opening is $\pi R^2$. If the openings are circular, then the total surface area of the openings is n times $\pi R^2$. The sheet shown here also has a thickness shown as z. in some embodiments, the resistance to exit port flow can also be increased to minimize and/or control the injectate exit port velocity. Flow resistance can be increased by increasing the number of openings (for a given open area) and/or increasing the perimeter of the openings (for a given open area), and/or increasing the thickness (z) of the openings (for a given open area). For example, a mesh with small openings will have a higher resistance to flow than a single opening of the same opening area.

A diffuse exit port design may include multiple holes in the conduit, holes in a secondary material that is attached the conduit, a mesh (polymer, metal, etc.) that is incorporated into the conduit, a break, or opening, in the conduit which is supported by other structures, such as a core wire, a sponge (Polymer, sintered or 3D printed metal or polymer), etc.

FIGS. 61A-D show some embodiments of diffuse exit port designs including a mesh (FIG. 61A), a porous polymer (FIG. 61B), a large exit port opening spanned by struts 6102 (FIG. 61C), a large exit port opening spanned by central core wire 6104 (FIG. 61D) and a spiral exit port opening (FIG. 61E). The materials of the exit port areas may be rigid, flexible, or semi-rigid.

Exit port design and distance from port to sensors are variables in the design and are optimized such that the sensor functions well in a wide range of conditions, including a range of blood flow velocities (1 cm/sec-200 cm/sec in either direction), a wide range of vessel and organ diameters, both small and large (0.5 mm diameter to 100 mm in diameter), and a wide range of infusion flow rates of the injectate (0.001 cc/min to 100 cc/minute, or more optimally 0.5 cc/min-5 cc/min), etc.

It may be desirable in some embodiments to limit the velocity of the injectate as it exits the injectate exit port. This can be done by limiting the injectate rate on the proximal end of the device, and can also be done by increasing the area of the opening(s) of the injectate exit port. Increasing the area of the openings of the exit port can be done by increasing the percentage of area that is open within the injectate exit port, and/or increasing the surface area of the injectate exit port.

Figure 62A:
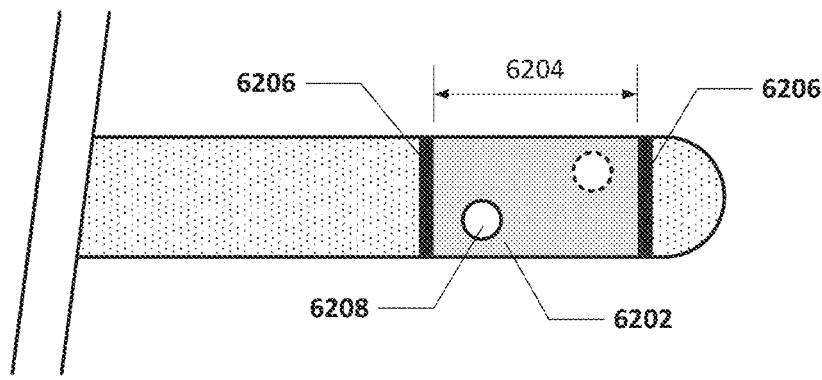
FIGS. 62A-C show some more examples of diffuse exit port designs.
Figure 62B:
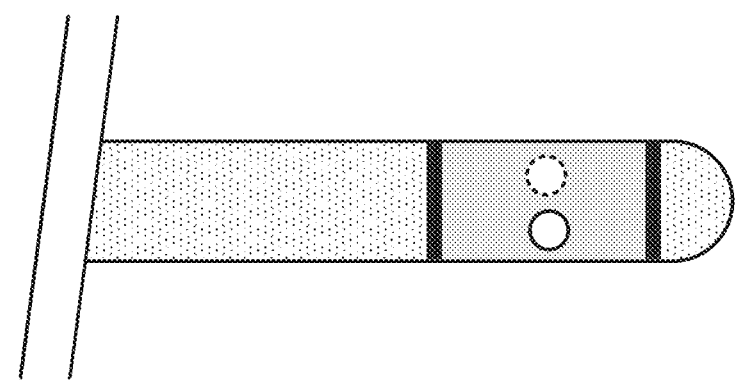
Figure 62C:
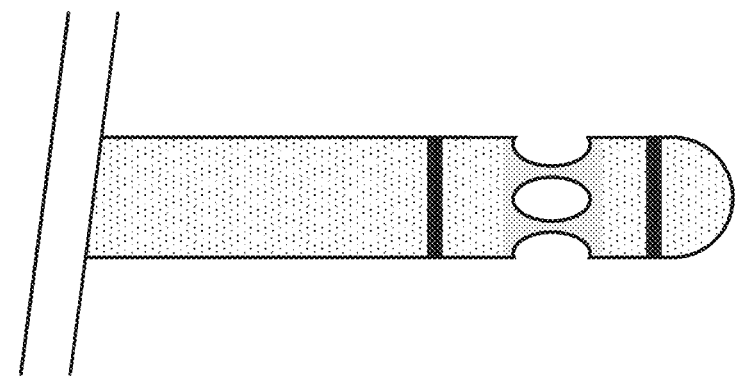

Some embodiments of a diffuse injectate exit port may include multiple openings circumferentially. FIGS. 62A-C show embodiments of the vascular catheter navigation device which includes diffuse exit port area 6202, sensor(s) 6206, which may be electrode pairs or other sensors, diffuse exit port area length 6204, and openings 6208. Note that openings outlined with a dotted line are on the back side of the device. FIG. 62A, for example, shows 2 openings circumferentially within exit port area length 6204. FIG. 62B also shows 2 openings circumferentially within exit port area length 6204, however in FIG. 62B, the openings are aligned circumferentially, where in FIG. 62A, the openings are staggered circumferentially.

As an example, the exit port may have two or more openings within about a 0.5 cm length. As another example, the exit port may have two or more openings aligned circumferentially within the exit port. As an example, the exit port may have three or more openings within about a 0.5 cm length. As another example, the exit port may have three or more openings aligned circumferentially within the exit port.

FIG. 62C shows an embodiment where the exit port openings cover more than 40% of the circumference of the diffuse exit port. In other embodiments, exit port openings cover more than 30% of the circumference of the diffuse exit port. In other embodiments, exit port openings cover more than 50% of the circumference of the diffuse exit port. In other embodiments, the exit port openings cover more than 30% of the area of the diffuse exit port. In other embodiments, the exit port openings cover more than 40% of the area of the diffuse exit port. In other embodiments, the exit port openings cover more than 50% of the area of the diffuse exit port. In other embodiments, the exit port openings cover more than 60% of the area of the diffuse exit port. The percentage of open area of a diffuse exit port may range from 10% to 99%, although more optimally 30% to 80% by area.

In some embodiments, the length 6204 of the diffuse exit port is greater than about 0.10 cm. In some embodiments, the length 6204 of the diffuse exit port is greater than about 0.25 cm. In some embodiments, the length 6204 of the diffuse exit port is greater than about 0.5 cm. In some embodiments, the length 6204 of the diffuse exit port is greater than about 0.75 cm. In some embodiments, the length 6204 of the diffuse exit port is greater than about 1.0 cm.

Figure 63A:
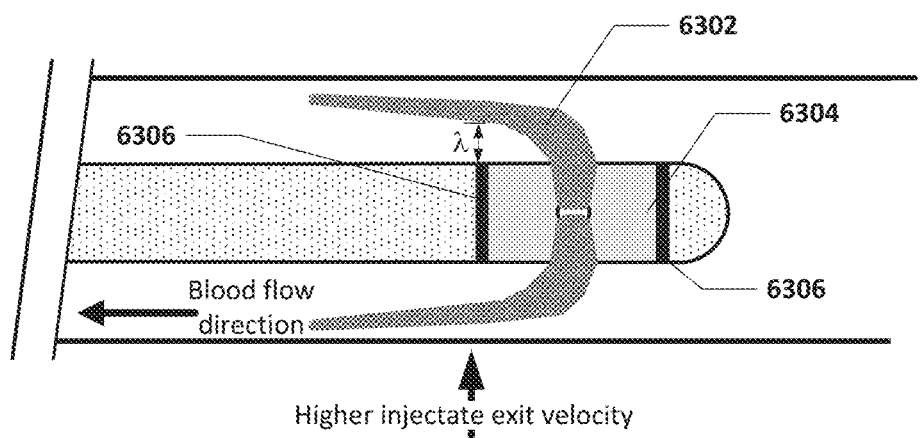
FIGS. 63A-D show how the injectate exit velocity impacts the sensor's ability to sense the injectate parameter within the vessel blood flow.
Figure 63B:
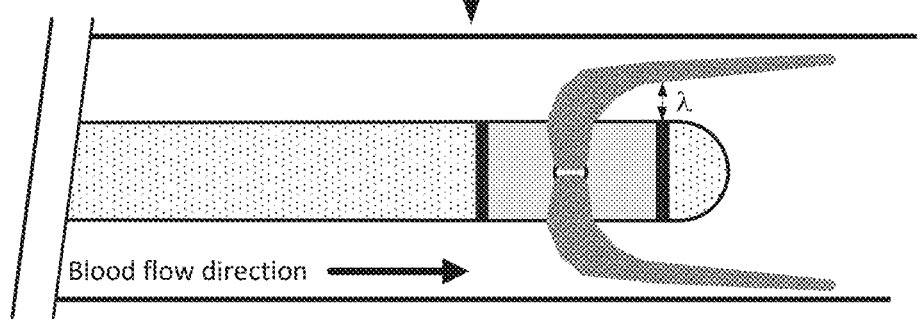
Figure 63C:
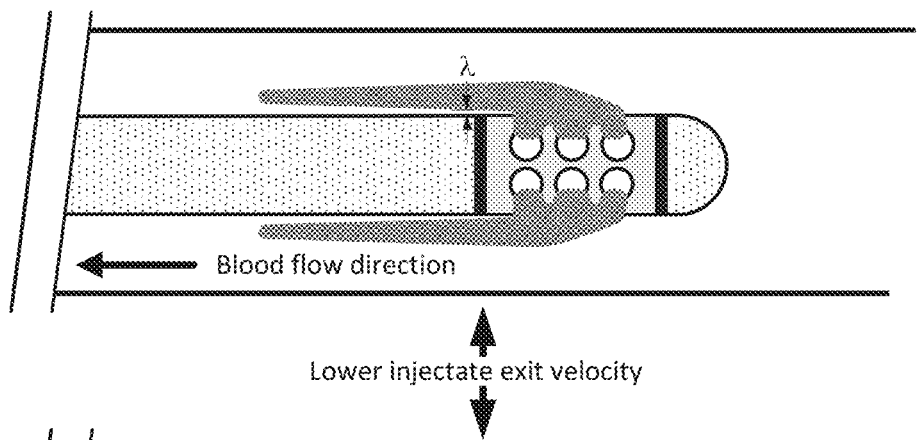
Figure 63D:
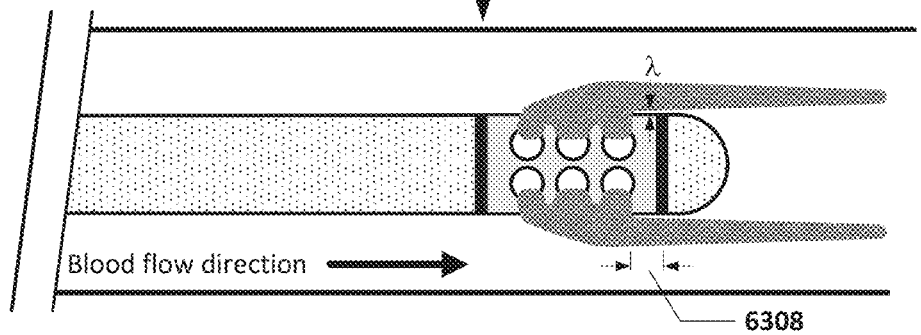

FIGS. 63A-D show that the injectate exit velocity impacts the sensor's ability to sense the injectate parameter within the vessel blood flow. FIGS. 63A and 63B show a 2 dimensional representation of the flow characteristics of injectate fluid 6302 as it exits injectate exit port area 6304 at a higher exit velocity. FIGS. 63A and B show the flow of the injectate fluid, at a given infusion flow rate, in opposing blood flow scenarios. The distance, $\lambda$, is the approximate distance between the exiting injectate fluid and sensor 6306, within the plane of the sensor. This distance may also be referred to as the boundary distance. FIGS. 63C and 63D show the fluid flow of the injectate, at the same infusion flow rate, exiting the device in a lower injectate exit velocity, for example via a diffuse exit port. Note that the boundary distance, $\lambda$, is much smaller in the low injectate exit velocity scenarios. To optimize sensor sensitivity, it is desirable to design the exit port so that $\lambda$ is at or near zero in laminar or less turbulent blood flow situations, and may be greater than zero in turbulent blood flow situations. Utilizing a diffuse exit port design as shown in FIGS. 63C and 63D allows one to control the boundary distance, $\lambda$, for any given proximal injectate injection rate, as well as bringing it close to zero in laminar or low turbulence blood flow situations. By choosing the appropriate exit port configuration for a given injectate injection rate, the sensor can perform under a range of blood velocities. The sensors, along with the analytical capabilities of the controller, can detect inline and opposing flow and can detect the difference between laminar and turbulent blood flow conditions.

For example, at an injectate infusion rate of 3 ml/min, the injectate inlet velocity may be around 6 cm/sec and the injectate exit velocity exiting the exit port may be around 1.5 cm/sec. This represents a ratio of inlet velocity:outlet velocity ratio of around 4. Alternatively, at an injection infusion rate of 5 ml/min, the injectate inlet velocity may be around 10 cm/sec and the injectate exit velocity exiting the exit port may be around 2.5 cm/sec. This represents a ratio of inlet velocity:outlet velocity ratio of around 4. Alternatively, the outlet velocity may be in the range of around 0 to 1 cm/sec. Alternatively, the outlet velocity may be in the range of around 1 to 3 cm/sec. Alternatively, the outlet velocity may be in the range of around 1 to 4 cm/sec. Alternatively, the outlet velocity may be in the range of around 1 to 6 cm/sec. Alternatively, the outlet velocity may be in the range of around 1 to 8 cm/sec. The inlet velocity:outlet velocity ratio may be around 4. Alternatively, the inlet velocity:outlet velocity ratio may be around 2-5. Alternatively, the inlet velocity:outlet velocity ratio may be around 1-6. Alternatively, the inlet velocity:outlet velocity ratio may be around 5-10. Alternatively, the inlet velocity:outlet velocity ratio may be greater than around 2. Alternatively, the inlet velocity:outlet velocity ratio may be greater than around 5. Alternatively, the inlet velocity:outlet velocity ratio may be greater than around 10.

In embodiments which include a diffuse exit port, the distance between the exit port and the sensor may be measured from the closest opening to the sensor. For example, in FIG. 63D, the distance between the exit port and the distal sensor would be length 6308.

In some embodiments of the vascular catheter navigation device, it is desirable to incorporate a sensor into or on the vascular catheter itself. This feature enables the user to detect whether the catheter has migrated over time, even after the guidewire/stylet has been removed. By including the sensor and infusion ports on the catheter itself, the need for a guidewire or stylet may also not be necessary. In some of these embodiments, the electrodes are designed such that the vascular catheter may be trimmed at the distal end without sacrificing the electrode and/or sensor function. For example, electrodes may be printed on the catheter with 3d printing technology, conductive ink may be used, metal bands may be attached, or flex circuits may be affixed to the catheter. Conductive plastics can also be co-extruded to create separate traces or electrode.

Figure 64A:
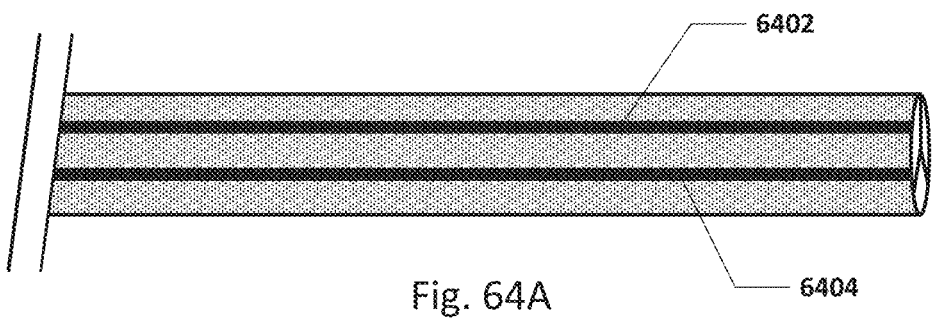
FIGS. 64A-64C show some embodiments of a trimmable vascular catheter with electrodes incorporated into the catheter.
Figure 64B:
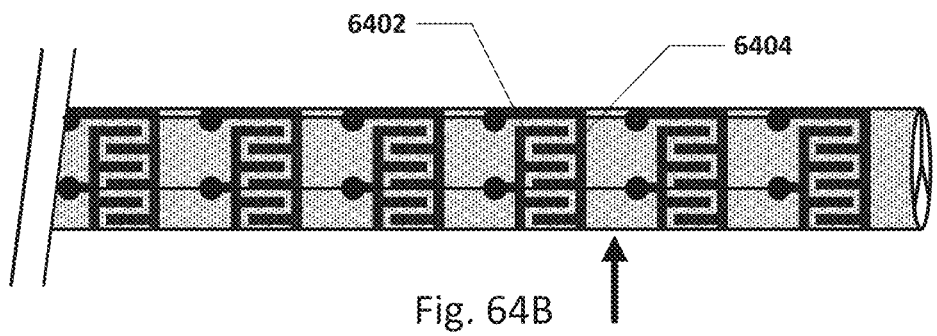
Figure 64C:
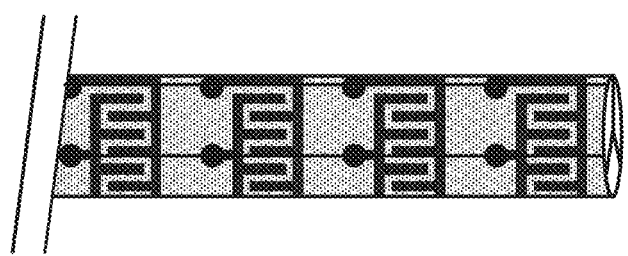

FIGS. 64A-64C show some embodiments of a trimmable vascular catheter with electrodes incorporated into the catheter. FIG. 64A shows electrode 6402 and electrode 6404 that run along the length of a catheter. FIG. 64B shows a vascular catheter with multiple electrode pair areas which can serve as a sensor. FIG. 64C shows the catheter in FIG. 64B after it has been trimmed at the arrow. The distal most sensor or sensors may be used for subsequent injectate parameter sensing during catheter placement. The controller can determine which sensor is the most distal based on the resistance of the sensor loop. The vascular catheter may range from about 42 to about 53 cm in length, and the length trimmed at the distal end may be up to around 6 cm.

Any of the conductivity sensor/electrodes disclosed herein may be incorporated into a rolled printed circuit board which may be wrapped around and attached to the device. Different manufacturing techniques may be used alone or in combination, including plating, masking, lithography, stamping, soldered etc.

The conductivity sensor may also be used to measure the ECG signal of a patient. The two technologies together may be used to identify the device distal tip location within the anatomy.

Figure 65:
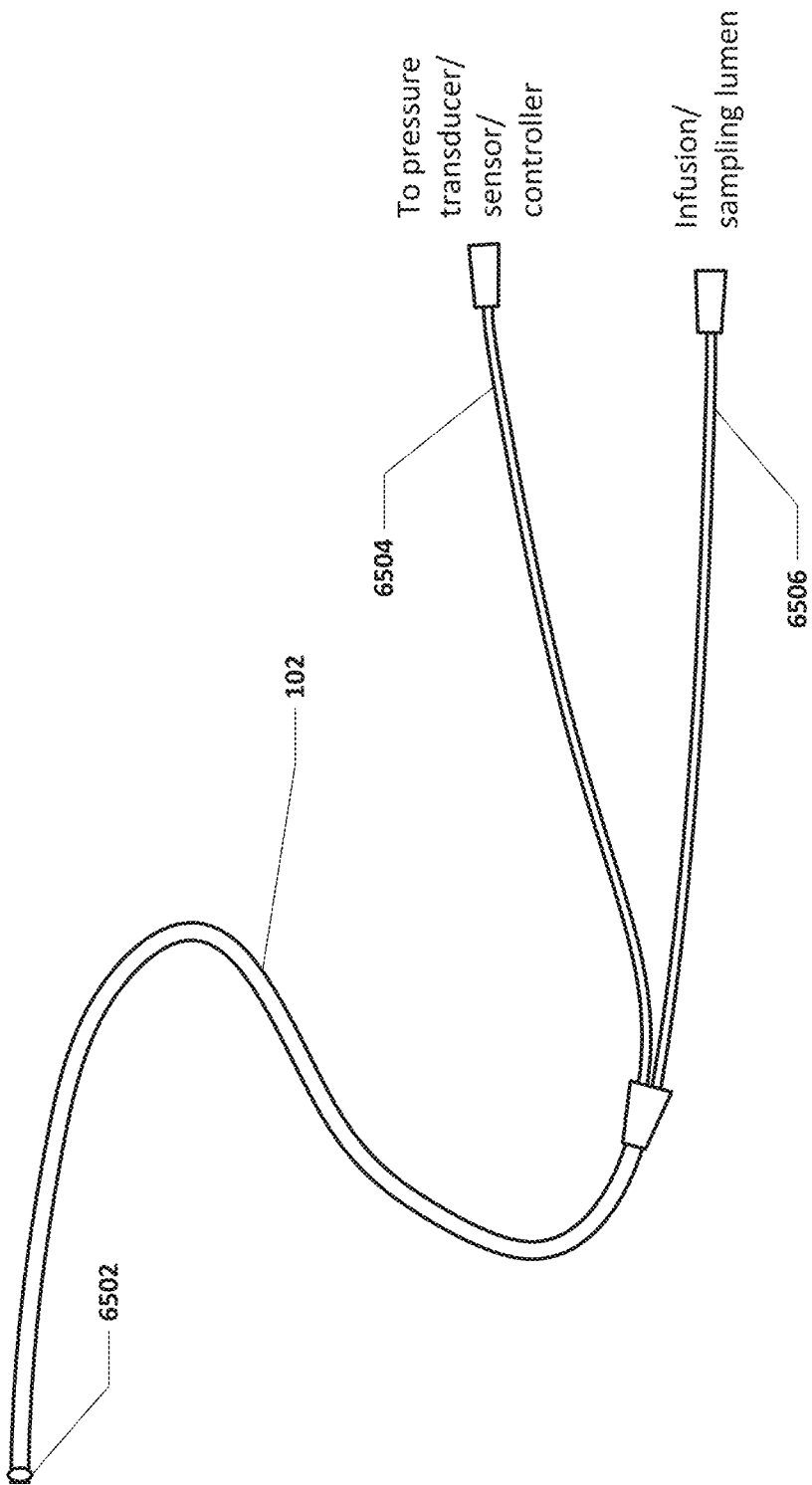
FIG. 65 shows an embodiment of the vascular navigation device.

FIG. 65 shows an embodiment of the vascular navigation device which uses pressure to navigate a vessel. The distal end of the vascular navigation device is inserted into the appropriate access vein, and advanced along the vein to its target location. These embodiments may not utilize an infused medium or injectate to determine device location. Alternatively, pressure-based vascular navigation embodiments may be combined with other embodiments disclosed herein.

After the vascular navigation device is inserted into the blood vessel, generally through a needle, or sheath, pressure sensing element, balloon or bladder 6502 senses pressures within the blood vessel. The pressure signals are communicated back to the controller where the pressure signal(s) are analyzed using a pressure transducer based on the pressure, pressure profile, pressure of more than one pressure bladder, or change in pressure over time and/or distance. For example, the controller can determine whether the distal end of the vascular navigation device is in an artery instead of a vein, based on magnitude and direction of blood flow around the vascular navigation device. If the controller determines that the distal end of the vascular navigation device is in an artery instead of a vein, a specific identifying signal may sound, including an audible, visual signal etc., instructing the user to remove the vascular navigation device, and any other device, such as sheaths, catheters etc., and apply pressure to the blood vessel.

Figure 66A:
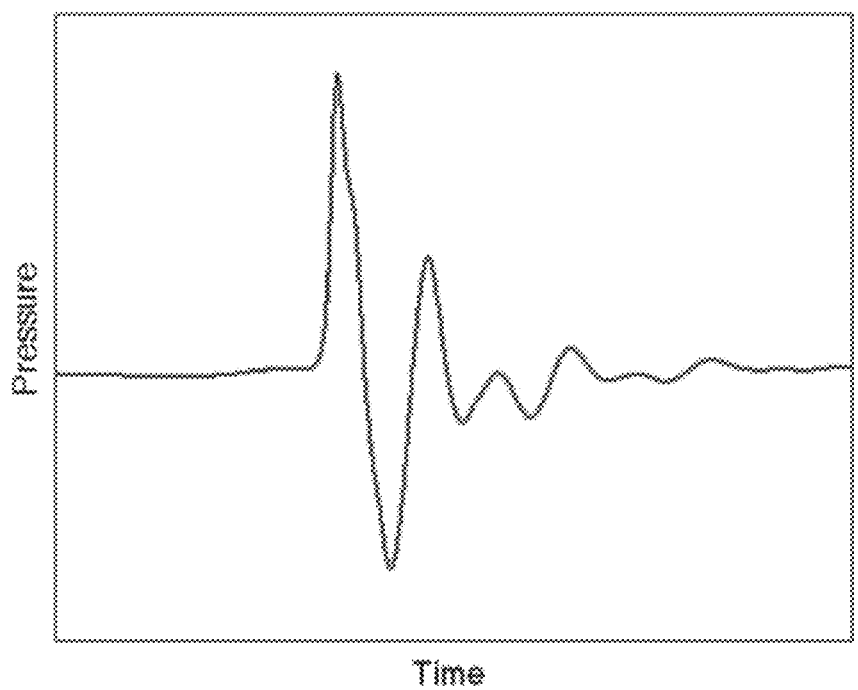
FIGS. 66A and 66B show pressure profiles for different blood flow directions.
Figure 66B:

Similarly, the pressure-based vascular navigation device can sense when the distal end is in the wrong branch of a vein, based on flow direction, and possibly flow profile and magnitude. When advancing the pressure-based vascular navigation device in the correct direction (toward the SVC-CAJ, in a vein), the pressure pulse advances over the vascular navigation device from the more proximal end to the distal end. Conversely, when moving the device away from the SVC-CAJ, the pressure pulse advances over the vascular navigation device from the distal end to the more proximal end. Some embodiments described herein make use of multiple pressure bladders to detect the directionality of flow. FIGS. 66A and 66B show the pressure profiles for these 2 flow different scenarios. The pressure shown is the pressure differential between the pressure in the sensing bladder (proximal to the reference bladder) and the reference bladder (closest to the distal tip of the vascular navigation device) measured by a differential pressure transducer. In FIG. 66A, as the pressure-based vascular navigation device is advancing in the same direction as flow, the sensing bladder sees the pressure wave before the reference bladder, resulting in an initial positive spike in pressure. In FIG. 66B, the catheter is advancing against flow, so the initial spike is negative. In this manner, vascular placement can be monitored to ensure it is being advanced in the direction of flow.

Figure 80:
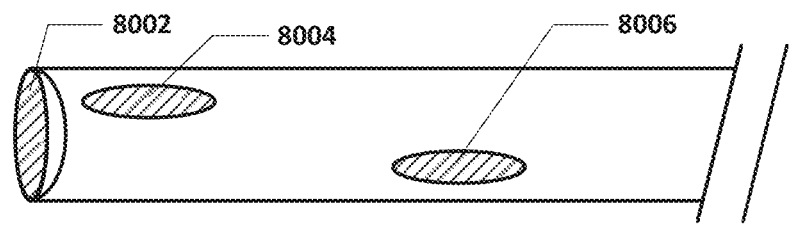
FIGS. 80-85 show embodiments of the vascular navigation device which include bladderless pressure sensing.
Figure 81:
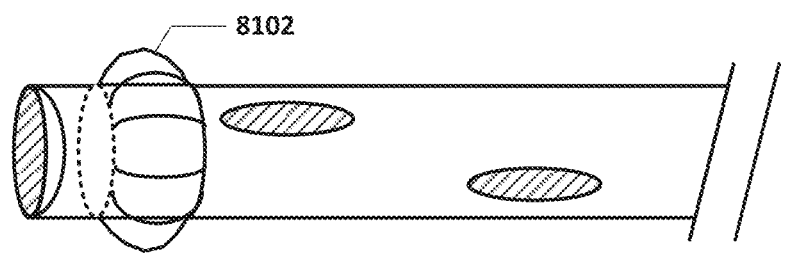
Figure 82:
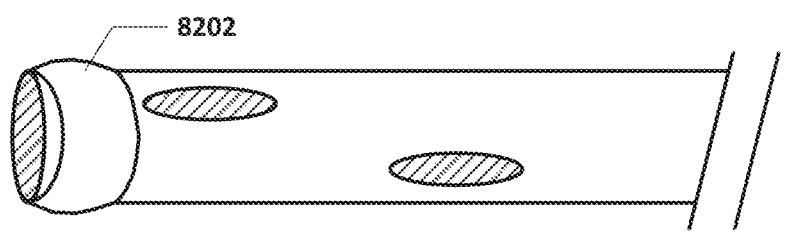

Although FIGS. 66A and 66B show pressure differential measurements between two pressure sensors, or two pressure lumens, it's possible that one lumen may be used and the data is analyzed to separate the readings from each pressure sensor. Pressure openings as shown in FIGS. 80-82, may also be used.

The vascular navigation device can sense when the distal end is up against a vessel wall based on a change in pressure sensed by one or more pressure bladders.

Spatial resolution of the pressure signals depend on positioning of the differential sensors or pressure openings. In certain embodiments, spatial resolution may be about 1-2 cm. Pressure readings may be taken about every 1 second. Alternatively, pressure readings may be taken about every 0.5 seconds. Alternatively, pressure readings may be taken about every 0.5-1.5 seconds.

The pressure-based vascular navigation device can detect the shape and magnitude of the heartbeat. The magnitude of the heart beat can be used to determine proximity to the heart, and thus location of the tip of the vascular navigation device.

FIG. 65 shows one pressure bladder 6502, one pressure lumen 6504 and one infusion/sampling lumen 6506. However, more than one infusion/sampling lumen and/or more than one pressure lumens/bladders may be present.

Figure 67:
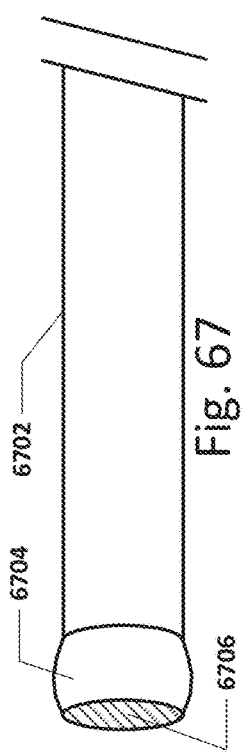
FIGS. 67-74 show various embodiments of the vascular navigation device

FIGS. 67-74 show the distal end of various embodiments of the pressure-based vascular navigation device. FIG. 67 shows a pressure-based vascular navigation device with a pressure bladder 6704 on the outside of pressure-based vascular navigation device 6702 at or near the distal end of the vascular navigation device. Infusion/sampling lumen opening 6706 allows fluids to be infused into the blood vessel, or samples taken from the blood vessel.

Figure 68:
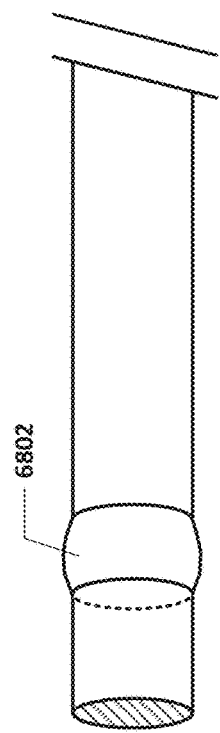

FIG. 68 shows a pressure-based vascular navigation device with pressure bladder 6802 near the distal end of the device. In this embodiment, the pressure bladder may be set back from the distal end of the vascular navigation device by around 1 mm to around 10 mm. Alternatively the pressure bladder may be set back from the distal end of the vascular navigation device by around 10 mm to around 30 mm.

Figure 69:
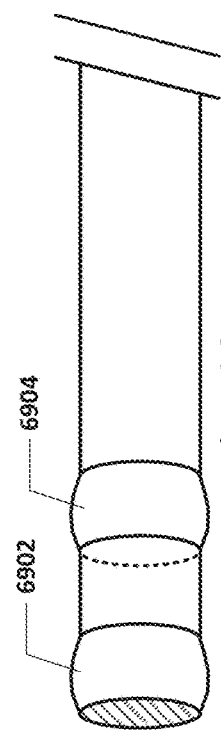

FIG. 69 shows a pressure-based vascular navigation device with more than one pressure bladder, including distal pressure bladder 6902 at or near the distal end of vascular navigation device, as well as second pressure bladder 6904 which is distanced from distal pressure bladder 6902 by around 1 mm to around 10 mm. Alternatively second pressure bladder 6904 may be distanced from distal pressure bladder 6902 by around 10 mm to around 30 mm. Two pressure bladders are shown here, but more than 2 pressure bladders may be present. They may be spaced from each other by the same distance, i.e. regularly spaced, or they may be spaced from each other by differing distances, i.e. irregularly spaced. The spacing between pressure bladders may be from around 1 mm to around 50 mm. Each pressure bladder may communicate with a separate pressure lumen.

Figure 70:
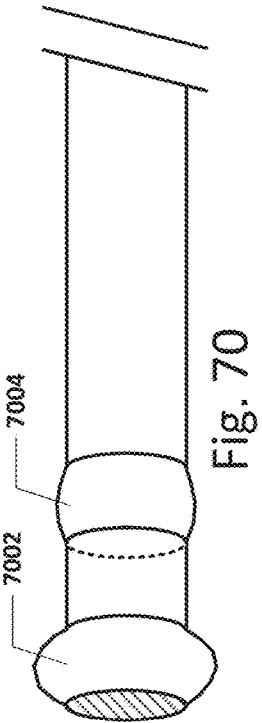

FIG. 70 shows a pressure-based vascular navigation device with more than one pressure bladder where the pressure bladders are of different sizes, including different lengths and/or diameters and/or volumes. Alternatively the pressure bladders may be of the same size, as shown in FIG. 69. More distal pressure bladder 7002 may be larger, or smaller than more proximal pressure bladder 7004.

Figure 71:
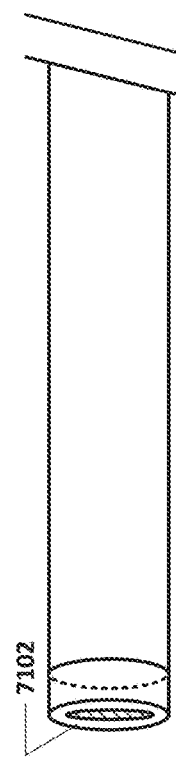

FIG. 71 shows a pressure-based vascular navigation device with pressure bladder 7102 on the inside of the vascular navigation device at or near the distal end of the device. This configuration may allow the pressure bladder to sense pressures within a blood vessel with less interference created by the pressure bladder contacting the vessel wall. Additionally, a second pressure bladder may be on the outside of the vascular navigation device to detect contact with the vessel wall and/or other pressures.

Figure 72:
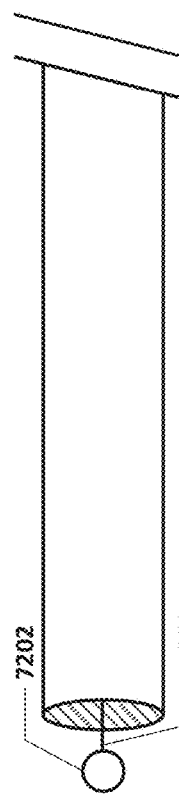

FIG. 72 shows an embodiment of a pressure-based vascular navigation device which includes pressure bladder 7202 on shaft 7204. Shaft 7204 may be a guidewire, other wire, small tube, stylet, small multi-lumen tube, or other elongated member which may pass through the inner lumen of a vascular catheter. Shaft 7204, in combination with bladder 7202, may be integrated with each other and may be separate from a vascular catheter, inserted into the vascular catheter either before insertion of a vascular catheter, or as needed. The shaft/bladder combination may be moveable within the lumen of a vascular catheter or may be fixed within a vascular catheter.

Figure 73:
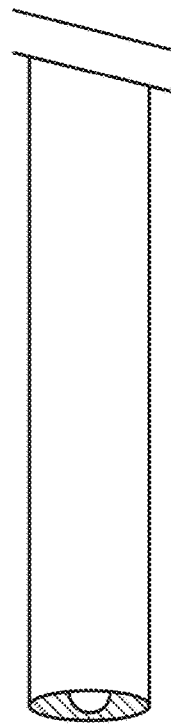

FIG. 73 shows a shaft/bladder combination located inside the distal opening of a vascular catheter. This arrangement may be achieved by moving the shaft/bladder combination within the vascular catheter or may be the shaft/bladder combination may be fixed to the vascular catheter in this or another position. This position inside the distal tip, as opposed to outside the distal tip as shown in FIG. 72, may allow the pressure bladder to sense pressures within a blood vessel with less interference created by the pressure bladder contacting the vessel wall. Additionally, a second pressure bladder may be on the outside of the vascular navigation device to detect contact with the vessel wall and/or other pressures.

Figure 74:
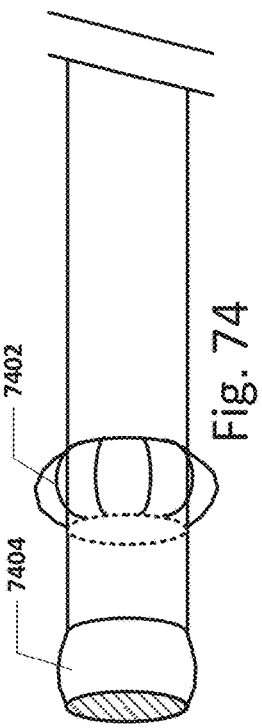

FIG. 74 shows an embodiment of a pressure-based vascular navigation device which incorporates spacer, or cage 7402 in addition to pressure bladder 7404. Spacer 7402 may help center the vascular navigation device within the blood vessel without disturbing blood flow past the device. Cage 7402 is shown here proximal to pressure bladder 7404, but other embodiments may include a cage more distal to a pressure bladder and/or multiple cages and/or pressure bladders. The embodiment shown here in FIG. 74 shows a cage, which allows blood to flow through it, however some embodiments may include a spacer which is in different configurations such as solid, perforated, grooved, etc. Different spacer configurations may be designed to affect blood flow in a predictable way. The spacer may also be inflatable or collapsible so that the vascular navigation device has a smaller diameter for introduction into the patient. A pressure bladder may also be located inside of a spacer.

In some embodiments a spacer and/or pressure bladder are slidable along the longitudinal axis of the outside or inside of the vascular navigation device shaft. In some embodiments a spacer and/or pressure bladder are able to be rotated around the outside or inside of the vascular navigation device shaft.

Priming

In embodiments that include a pressure bladder, obtaining sensitive, high resolution and accurate pressure measurements from a pressure bladder, it is important that the pressure bladder be adequately "primed". This means that the pressure bladder is pressurized to the optimal pressure to obtain the maximum magnitude pressure readings from blood flow, blood pressure and vessel pressure. Continual adjusting and maintaining of a balance of pressure on either side of the membrane of the pressure bladder may be necessary and controlled by the controller. This balance of pressure may be referred to as a pressure differential. In some embodiments the preferred pressure differential is at or around zero. In some embodiments the preferred pressure differential may be a different value. Pressure impinging on the external interface of the pressure bladder (facing the internal aspect of the blood vessel) is subject to change according to the physiology of the patient. Pressure on the internal interface of the pressure bladder (which is in fluid communication with a fluid column within the vascular navigation device which is in fluid communication with the controller) is subject to degradation because of fluid leakage and imperfect seals.

Upon first insertion of the vascular navigation device, external pressure is typically applied to the fluid column and against the pressure interface to a first approximation of pressure being exerted on the pressure interface from within the blood vessel. Pressure signals, as measured across a pressure interface, have a maximal amplitude when the pressure differential is about zero. Accordingly, the amplitude of a pressure signal can be used to tune the pressure being applied from the fluid column against the pressure interface. This process of applying an appropriate amount of pressure against the interface may be referred to as priming the fluid column or priming the pressure bladder. Inasmuch as pressures on either side of the pressure interface may change, as described above, the fluid column may need to be re-primed or re-tuned, from time to time. The necessity of re-priming can be monitored by testing small changes in pressure so as to achieve maximal amplitude of a pressure signal profile. Alternatively, the priming can automatically occur via the controller on a periodic basis.

Embodiments of the disclosed system and method include automatic pressure tuning by a controller. Accordingly, the tuning system can detect the optimum target pressure and volume to inflate the pressure bladder by monitoring sensed pressure signals and adding or removing air or fluid volume as needed. For example, upon insertion of the vascular navigation device, a pressure tuning circuit that regulates the pressure bladder volume and pressure may inflate the bladder until it detects a physiologic-sourced pressure rate, such as a heart rate. Upon sensing that rate, the pressure tuning controller may add or subtract minute amounts of air in a routinized sequence until the amplitude of the sensed wave is greatest. The control feedback loop between the optimally tuned pressure (manifesting as pressure bladder pressure and volume) and the sensed physiologic pressure profile iterates continuously and or as needed to ensure high fidelity measurement of the physiologic data. In some embodiments, automatic pressure tuning may be performed in the apparent background while the physiologic data is being transmitted and displayed; in other embodiments the system may suspend transmission of physiologic data during a pressure tuning sequence.

Embodiments of the disclosed technology include a gas delivery system that can deliver gas in a priming operation, whereby pressure can be applied to a fluid column proximal to the proximal-facing aspect of the pressure interface. A source of gas, such as compressed air or liquid is held in a storage tank. Using CO2 as an example, CO2 is controllably released from the storage tank through a pressure regulator that can step pressure in the tank (for example, pressure of about 850 psi) down to the range of about 1 psi to about 2 psi. Released gas passes through a filter and a pressure relief valve set at about 2.5 psi. The pressure relief valve is a safety feature that prevents flow through of gas at a level greater than 2.5 psi in the event of failure of the upstream regulator. CO2 exiting the pressure relief valve next passes through a first solenoid-controlled fill valve to enter the catheter line, ultimately filling the pressure bladder that comprises the pressure-sensing interface. Pressure within the pressure bladder is allowed to rise to a level as high as 30 mm Hg, whereupon the first solenoid-controlled valve closes. A second solenoid-controlled valve, distal to the first valve operates as a drain valve, which can release pressure to a target pressure. Alternatively, the drain valve may be activated until a pressure waveform is detected after which the pressure bladder will be optimally primed and the valve will be closed. The drain valve may be subject to proportional control, operably based on voltage or pulse-width modulation (PWM), which allows a drain rate sufficiently slow that the target pressure is reached and the valve can be closed prior to overshoot. Alternatively, a peristaltic or other air pump may be utilized to fill the pressure bladder with room air.

Figure 75:
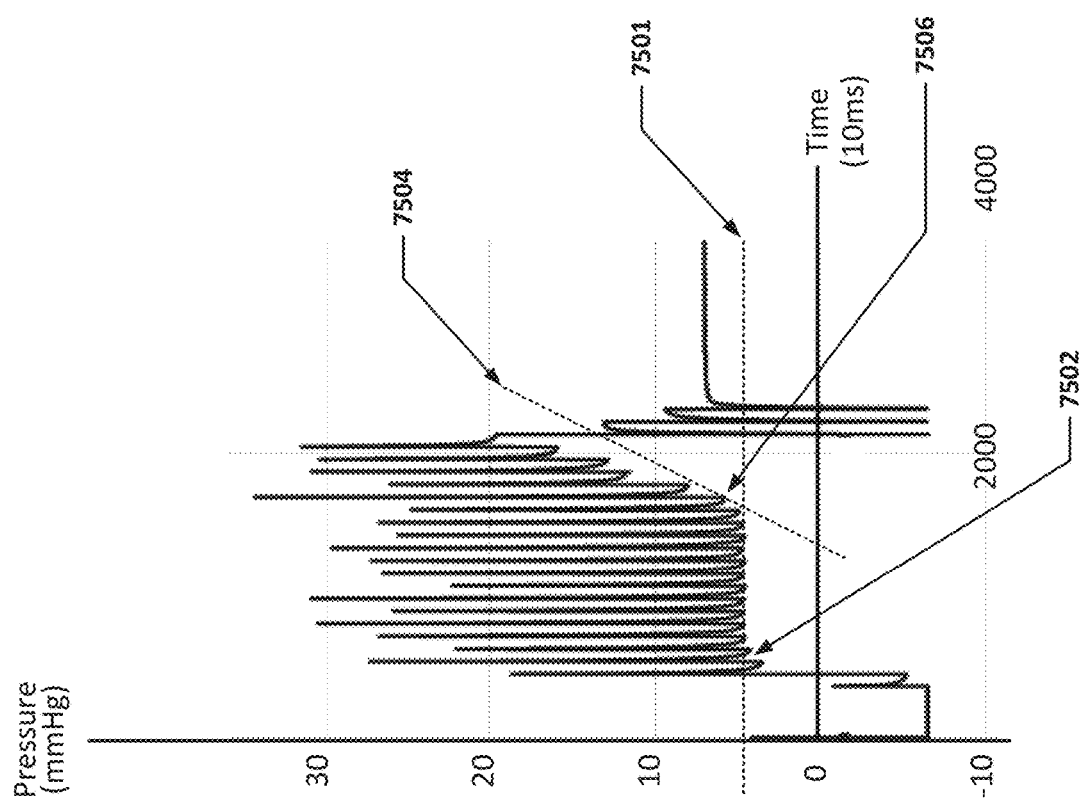
FIGS. 75 and 76 show graphs representing pressure balloon priming methods in some embodiments.
Figure 78:
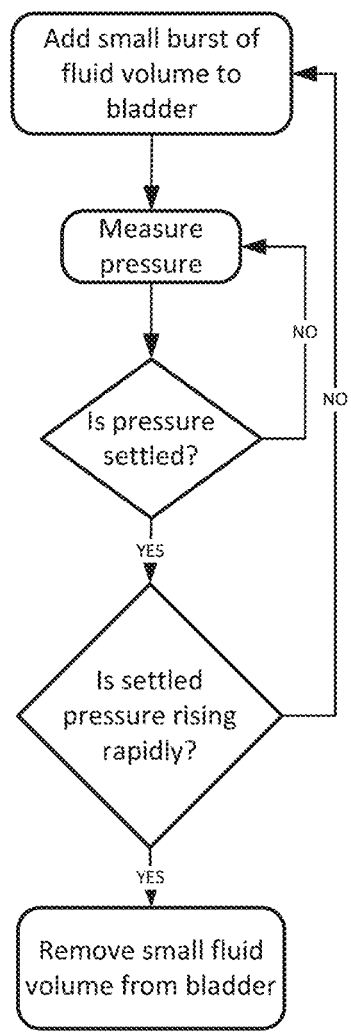

FIG. 75 shows a graph representing a pressure bladder priming method in some embodiments. Here, small volume bursts (roughly about 0.3 cc) of fluid volume are added to the pressure bladder and the pressure within the bladder is measured. Small volume bursts of fluid are introduced until the measured pressure within the bladder settles to a stable pressure 7501. This transition is shown at inflection point 7502. Volume bursts are introduced past this point until the measured pressure starts to rapidly increase (for example if slope 7504 of the curve is greater than about 2 mmHg/10 ms). This inflection point is shown at 7506. At this point the pressure within the bladder is reduced to a pressure around or slightly above stable pressure 7501. This pressure represents the prime pressure measuring pressure in some embodiments. This process is also represented in the flowchart in FIG. 78.

The small volume bursts of fluid may be from around 0.2 cc to around 0.4 cc. The small volume bursts of fluid may be from around 0.1 cc to around 0.5 cc. The small volume bursts of fluid may be up to around 0.5 cc. The small volume bursts of fluid may be up to around 1.0 cc.

Figure 76:
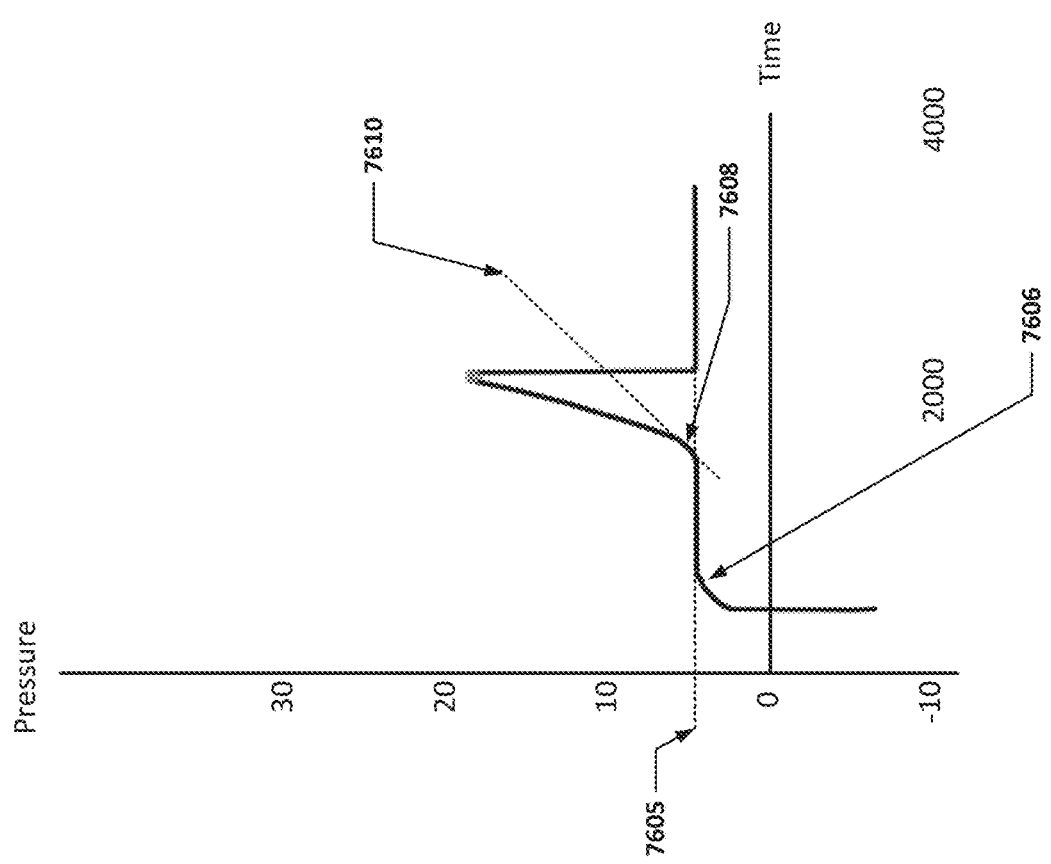
Figure 79:
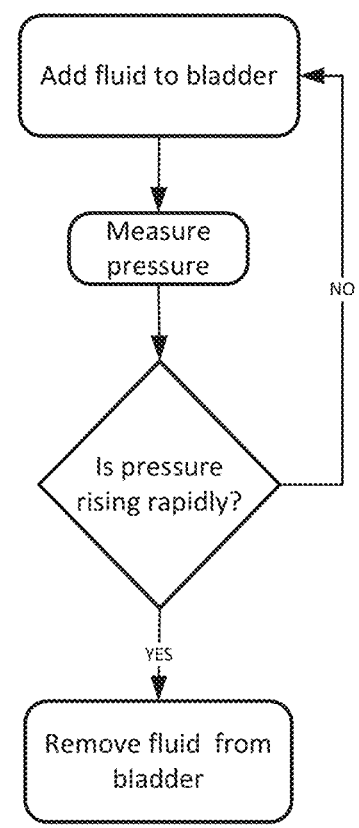

FIG. 76 shows a graph representing a pressure bladder priming method in some embodiments. This method is similar to that shown in FIG. 75, except that the pressure is increased within the pressure bladder more smoothly, without the bursts shown in FIG. 75. Fluid volume is added to the pressure bladder and the pressure within the bladder is measured. Bladder pressure is increased until the measured pressure within the pressure bladder settles to stable pressure 7605. This transition is shown at inflection point 7606. Bladder pressure is increased past this point until the measured pressure starts to rapidly increase (for example if slope 7610 of the curve is greater than about 2 mmHg/10 ms). This inflection point is shown at 7608. At this point the pressure within the bladder is reduced to a pressure around or slightly above stable pressure 7605. This pressure represents the prime pressure measuring pressure in some embodiments. This process is also represented in the flowchart in FIG. 79.

Figure 77:
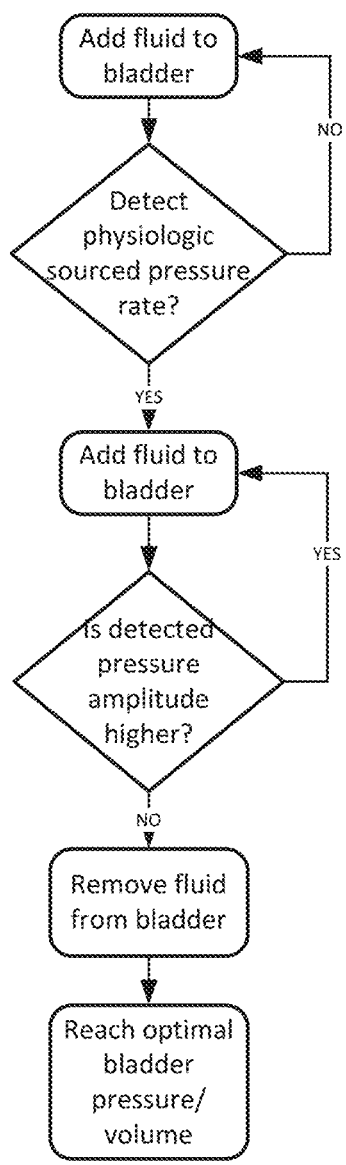
FIG. 77-79 show flow charts of possible logic in various embodiments of the invention.

FIG. 77 shows a flowchart of the pressure bladder priming process of certain embodiments. Embodiments of the disclosed system and method include automatic pressure tuning by a controller. Accordingly, the tuning system can detect the optimum target pressure and volume to inflate the bladder by monitoring sensed pressure signals and adding or removing air volume as needed. For example, upon insertion of the vascular navigation device, a pressure tuning circuit that regulates the pressure bladder volume and pressure will inflate the bladder until it detects a physiologic-sourced pressure rate. Upon sensing that rate, the pressure tuning controller will add or subtract minute amounts of air or fluid (roughly about 0.3 cc) in a routinized sequence until the amplitude of the sensed wave is greatest. The control feedback loop between the optimally tuned pressure (manifesting as pressure bladder pressure and volume) and the sensed physiologic pressure profile iterates continuously and or as needed to ensure high fidelity measurement of the physiologic data. In some embodiments, automatic pressure tuning may be performed in the apparent background while the physiologic data is being transmitted and displayed; in other embodiments the system may suspend transmission of physiologic data during a pressure tuning sequence.

The minute amounts of air or fluid may be from around 0.2 cc to around 0.4 cc. The minute amounts of air or fluid may be from around 0.1 cc to around 0.5 cc. The minute amounts of air or fluid may be up to around 0.5 cc. The minute amounts of air or fluid may be up to around 1.0 cc.

FIGS. 80-85 show embodiments of the pressure-based vascular navigation device which include bladderless pressure sensing. These embodiments may also include pressure bladders. One advantage of bladderless pressure sensing is that priming may not be required. FIG. 80 shows the distal end of a vascular navigation device with opening 8002 to the infusion or sampling lumen. Opening 8004 and opening 8006 connect to 2 separate pressure lumens, which connect to a differential pressure transducer via a fluid column. Instead of a pressure bladder as shown in other embodiments, the embodiment in FIG. 80 includes a pressure interface at openings 8004 and 8006. This interface may be the meniscus between a gas and a liquid, such as air and blood. Alternatively this interface may be the meniscus between two different fluids. Alternatively or additionally this interface may include a membrane which separates two fluids. The membrane may be loose so that the interface between the two fluids is free to move depending on pressures to which it is exposed. The membrane may be impermeable to one or both of the fluids involved.

For example, if a gas is used in the pressure lumen(s) of the pressure-based vascular navigation device, and the lumen is sufficiently small, the gas may not escape the lumen and enter the bloodstream. Instead, the interface between the blood and the gas will form a meniscus which serves as a pressure interface, similar to the pressure bladders disclosed herein, but without the need for priming. A liquid may alternatively be used in the pressure lumen(s), preferably a liquid with different properties, such as different viscosity from those of blood.

FIG. 81 shows an embodiment of the pressure-based vascular navigation device with 2 pressure lumens and cage 8102 which may help center the device in the blood vessel. Other centering mechanisms may be used, such as loops, wires, balloons, bumpers etc.

FIG. 82 shows an embodiment of the pressure-based vascular navigation device with 2 pressure lumens and pressure bladder 8202. The pressure bladder may serve both to center the device within the blood vessel, and also to sense pressure exerted by the vessel wall to aid in navigation. In this embodiment 3 pressure lumens may be present in the device.

Alternatively, the membrane may serve as a pressure bladder similar to other pressure bladders disclosed herein. In these embodiments, priming may still be necessary.

Figure 83:
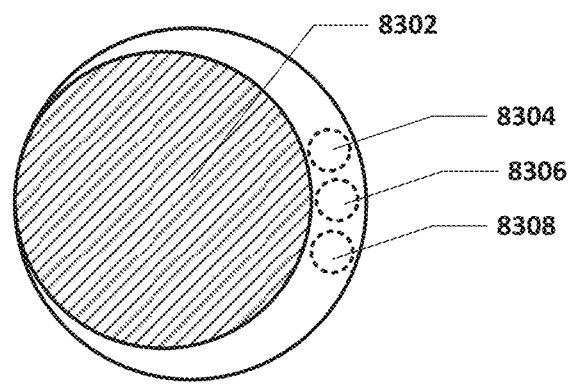
Figure 84:
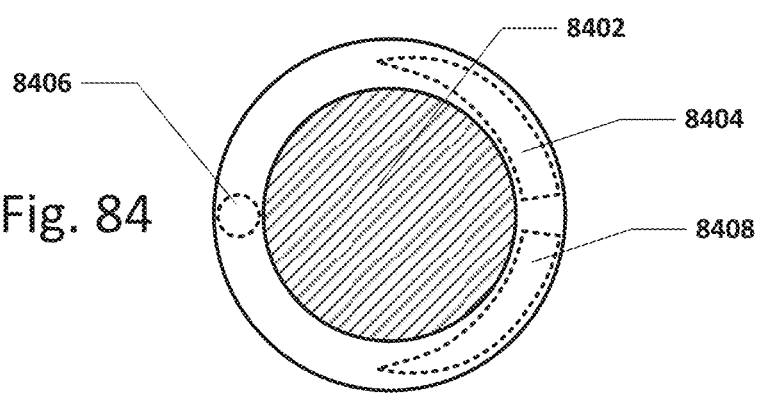
Figure 85:
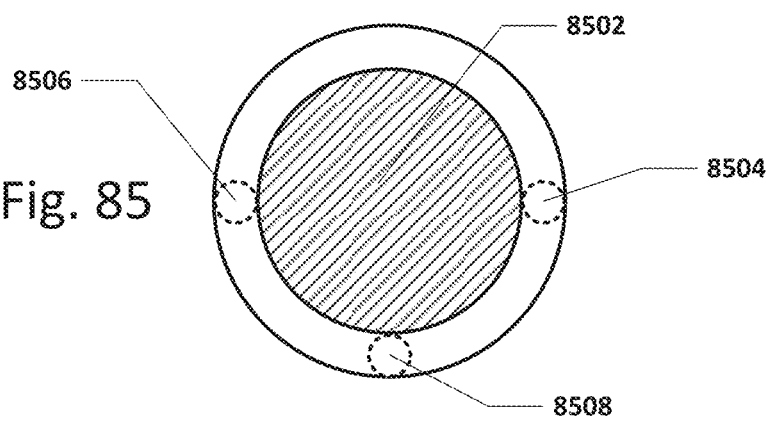

FIGS. 83-85 show various cross sections of the pressure-based vascular navigation device. These configurations may be utilized with any of the embodiments disclosed herein. FIG. 83 shows infusing/sampling lumen 8302, and pressure lumens 8304, 8306 and 8308. This configuration may be particularly useful in the embodiments shown in FIGS. 80-82, where it may be advantageous to have two pressure lumens close to each other on a side of the catheter wall. For example, the more than one pressure interface opening may be on the same half of the circumference of the vascular navigation device catheter shaft. This allows pressure differentials to be detected along one side of the catheter vs. between different sides of the catheter. For example, lumen 8304 may connect to one pressure interface opening and lumen 8306 may connect to another pressure interface opening. Optionally, pressure lumen 8308 may connect to a pressure bladder, such as is shown in FIG. 82. Alternatively, more than 2 pressure interfaces may be present on the vascular navigation device.

There are advantages to a pressure lumen with a small cross sectional area and/or a small volume. The smaller the volume, the less fluid/gas needs to be moved to transfer the pressure sensed at the catheter tip, through the fluid column in the device, to the pressure transducer connected to, or integrated with, the controller. In addition, the smaller the pressure interface opening, the more likely a meniscus will form between the fluid in the pressure lumen, and the blood in the blood vessel. To be clear, "fluid" may comprise either gas or liquid.

FIG. 84 shows infusing/sampling lumen 8402, and pressure lumens 8404, 8406 and 8408. In this example, pressure lumens 8404 and 8408 may be connected to pressure interface openings and pressure lumen 8406 may be connected to a pressure bladder. In this configuration, lumens 8404 and 8408 have a larger cross sectional area and volume than the configuration in FIG. 83, while still allowing the 2 pressure interface openings to be close to each other on a side of the catheter wall.

FIG. 85 shows another cross sectional view which may be used with any of the embodiments disclosed herein. This embodiment includes shows infusing/sampling lumen 8502, and pressure lumens 8504, 8506 and 8508.

Note that although many figures shown here incorporate the pressure lumens into the vascular catheter, the vascular navigation device may be a stand-alone device which fits inside a vascular catheter, and can be removed once vascular catheter placement has been completed. The vascular navigation device, for example, may serve as a stylet for a standard vascular catheter.

In some embodiments of the pressure-based vascular navigation device, one or multiple pressure bladders may be used, one or more pressure interface openings may be used, a combination of pressure bladders and pressure interface openings may be used, etc. Other pressure measuring mechanisms may also be used, including small pressure transducer(s) on the catheter, piezoelectric pressure sensors etc.

Embodiments with different types of sensors are disclosed herein. It is understood that any type of sensor may be used with any of the embodiments disclosed herein. For example, any of the embodiments disclosed herein may utilize sensors that sense electrical properties, such as conductance or resistance.

FIG. 86 shows an embodiment of the vascular navigation device which uses electrodes as sensors to sense conductance of blood and/or mixed blood/injectate flowing between electrode pairs, where an electrode pair may be considered one sensor. In this embodiment, stylet 8604 is configured to fit within catheter 8602. Stylet 8604 includes proximal electrode pair, or sensor, 8606 and distal electrode pair, or sensor, 8608. Injectate is injected through a lumen in the catheter or the stylet and exits the stylet via openings 8610 in diffuse exit port area 8612. Electrode leads 8614 in this embodiment are coiled around stiffener 8616 of the stylet. Also shown is stylet end plug 8618. The stylet end plug may have a blunt tip, as shown here, or may incorporate a soft protrusion. Four electrode leads are shown here, but fewer leads may be used. For example, a single lead may connect to both ground electrodes of the two sensors, resulting in three leads instead of four.

FIG. 87 shows an embodiment of the vascular navigation device where stiffener 8616 exits beyond end plug 9618. The stiffener may help with guidance of the device through the vasculature. The end plug may be made from adhesive, polymer, metal or other suitable material.

FIG. 88 shows an embodiment of the vascular navigation device where stiffener 8616 ends in a curved portion. The curved portion may be stiff, or more flexible than the more proximal section of the stiffener. The curved portion may be passive, i.e. a set curve in the device, or the curved portion may be active, where the user can change the shape of the curve or the amount of curvature in the tip of the device to help navigate the vasculature. The changing of the curve may be done from the proximal end during the procedure, or may be done prior to the procedure. The curve may be smooth or sharp, i.e. a bend. The curve may be any suitable angle, for example, around 120 degrees, or around 100 degrees to around 140 degrees.

Figure 89:
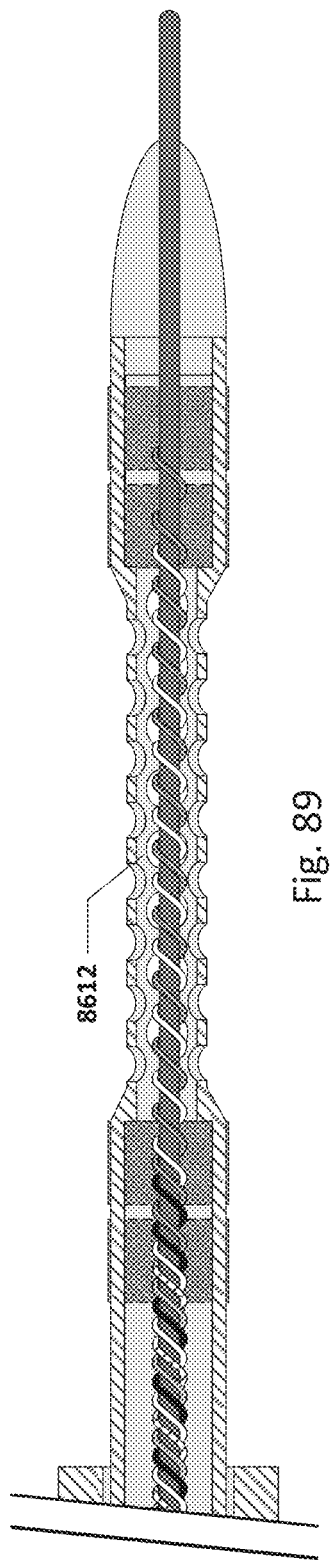
FIG. 89 shows an embodiment of the vascular navigation device with a reduced diameter exit port area.

FIG. 89 shows an embodiment of the vascular navigation device with reduced diameter exit port area 8612. For example, the outer diameter of exit port area 8612 may be smaller than the outer diameter of the electrode/sensor area of the device. This embodiment allows for different fluid flow dynamics of the injectate exiting the exit port via the openings. Alternatively, the outer diameter of the exit port area may be greater than the outer diameter of the electrode/sensor area of the device.

Figure 90A:
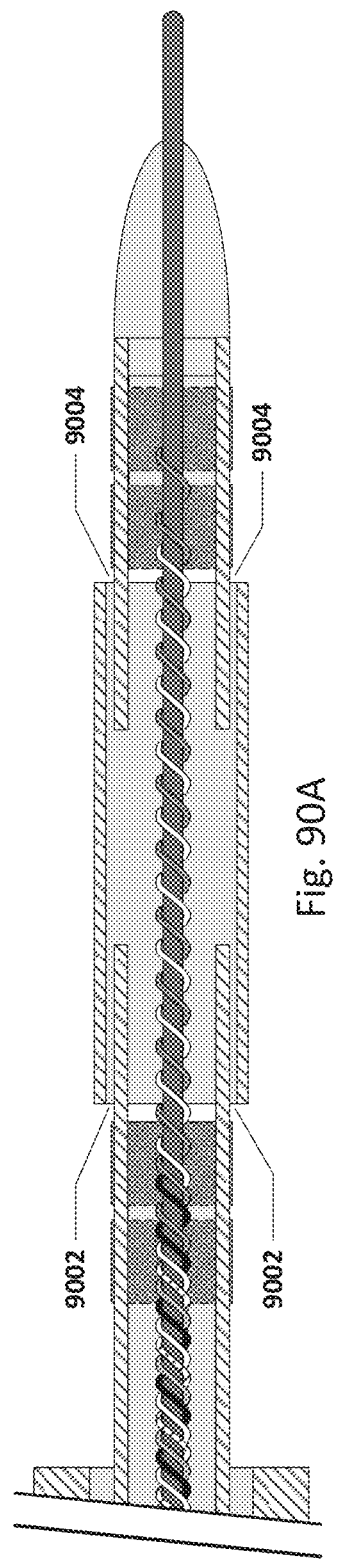
FIG. 90A shows an embodiment of the vascular navigation device with a sleeve style exit port area.

FIG. 90A shows an embodiment of the vascular navigation device with a sleeve style exit port area. In this embodiment, the injectate exits the stylet via proximal opening(s) 9002 and/or distal opening(s) 9004. The openings may be annular or comprise one or more openings around the circumference of the device. This embodiment allows for different fluid flow dynamics of the injectate exiting the exit port via the openings. Other embodiments may include baffle(s) or skirt(s) adjacent to the openings to direct the injectate flow as it exits the exit port.

Figure 90B:
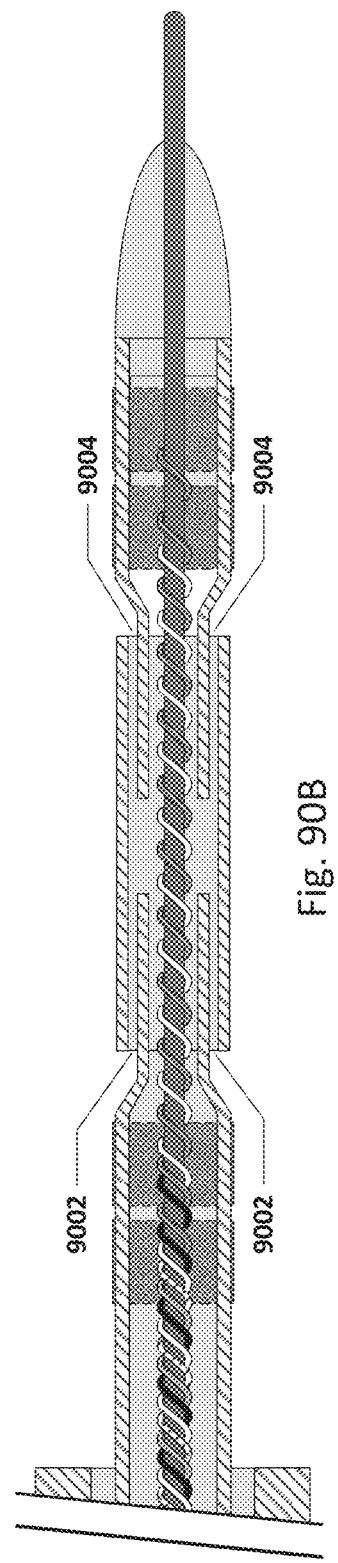
FIG. 90B shows an embodiment of the vascular navigation device with a sleeve style exit port area.

FIG. 90B shows an embodiment of the vascular navigation device with a reduced diameter sleeve style exit port area. In this embodiment, the exit ports are recessed. In other words, the fluid exiting the exit ports exits within a recess of the outer surface of the device. Similar to the embodiments shown in FIGS. 89 and 90A, this may allow the injectate fluid to exit the device in situations where the device is up against a wall of a vessel, or in other confining situations. Embodiments with recessed exit ports may also aid in reducing the boundary distance, $\lambda$, as shown in FIGS. 63A-63D. Embodiments with diffuse exit ports, sleeve exit ports and recessed exit ports may reduce the boundary distance, $\lambda$.

FIG. 91 shows an embodiment of the vascular navigation device with a double layer exit port area. Inner exit port area 9102 in this embodiment is coaxial with, and inside, outer exit port area 9104. This embodiment allows for different flow dynamics of the injectate exiting the exit port area.

FIG. 92 shows an embodiment of the vascular navigation device where the core, or stiffener, includes the leads for the sensors/electrodes. Shown here are 4 insulated leads 9202 within outer sheath 9204. An additional stiffening core may or may not be included in the bundle, which makes up the stiffener. In some embodiments, the insulated leads are stripped and coiled at their distal ends to create coiled electrodes 9206 on the outside of stylet.

FIG. 93 shows an embodiment of the vascular navigation device in which the stiffener is exposed at the distal end forming distal most electrode 9302.

In these, and other embodiments, the space between OD 9304 of the stiffening core wire and ID 9306 of the outer tube of the device may be important. This defines, at least along a portion of the device, the injection area for fluid injection. The ratio of tube ID to stiffener OD may be around 0.4. Alternatively, the ratio of tube ID to stiffener OD may be around 0.3-0.5. Alternatively, the ratio of tube ID to stiffener OD may be around 0.2-0.6. Alternatively, the ratio of tube ID to stiffener OD may be around 0.1-0.7. In some embodiments, the OD of the stiffening core wire is zero or essentially zero which would cause this ratio to be or approach infinity.

In these, and other embodiments, the ratio of exit port openings total area (for example, port length 6204*% port open area*tube ID 9306*$\pi$) to the cross sectional area defining the space between the stiffener OD and the tube ID ($\pi$(tube ID 9306/2)$^2$-$\pi$ (stiffener OD 9304/2)$^2$) may be important. This ratio may be around 4.5. Alternatively, this ratio may be around 1.8-14. Alternatively, this ratio may be around 1.4-20. Alternatively, this ratio may be around 1.2-30. In embodiments where the stiffener OD is zero, this ratio may be around 4. Alternatively, in embodiments where the stiffener OD is zero, this ratio may be around 1.6-13. Alternatively, in embodiments where the stiffener OD is zero, this ratio may be around 1.2-30.

Figure 94:
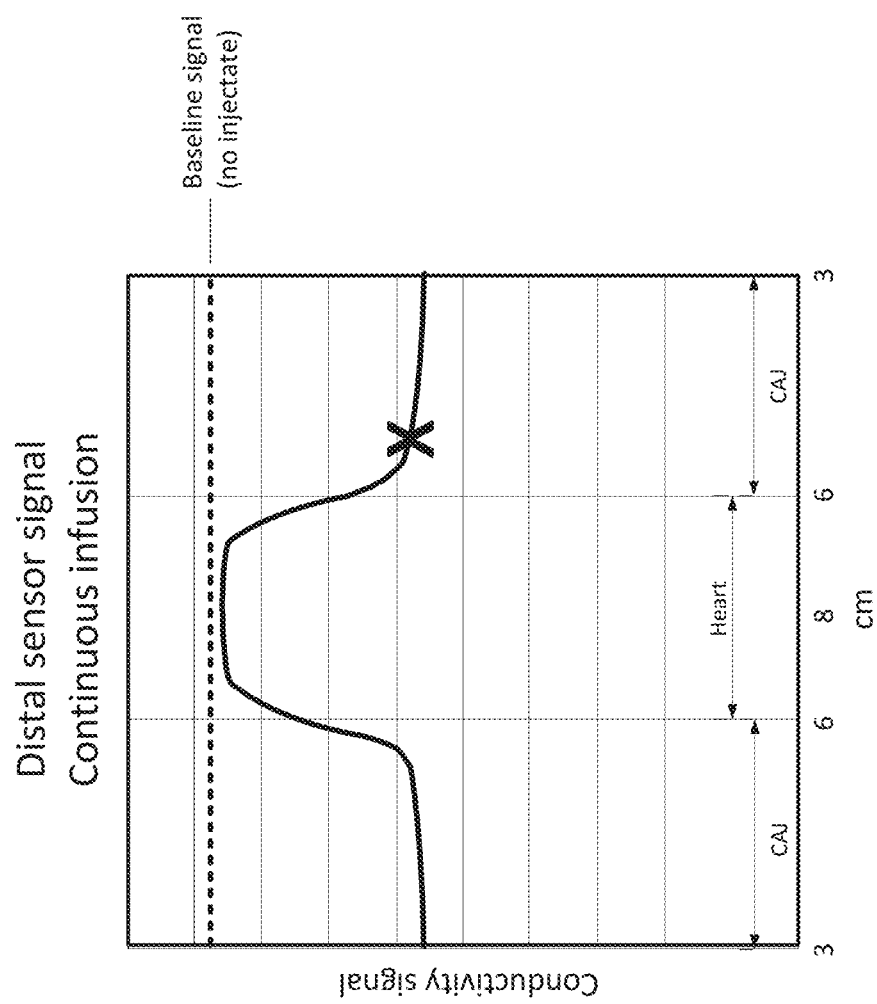
FIG. 94 shows the magnitude of the sensor signal within the anatomy.

FIG. 94 shows the relationship between the magnitude of the sensor signal and the location of the navigation device. FIG. 94 shows conductivity data collected from the distal sensor of a vascular navigation device which includes conductivity sensors. These data represent a signal from a vascular navigation device during constant infusion of the injectate fluid, as opposed to intermittent or bolus infusion of injectate fluid. In this case, the injectate fluid has a lower conductivity than blood.

This signal has been dampened/filtered to show more clearly the magnitude of the signal as the navigation device is navigated through the vasculature. The distal tip of the device is navigated through the SVC, into the CAJ, into the heart, and then retracted back through the CAJ and the SVC. The conductivity signal at baseline, with no infusion of injectate medium, is represented by the dotted line. This is generally what the conductivity signal would be if the device were advanced through the vasculature without the injection of any injectate. However, when injectate is continuously infused through the device, so that it exits the device openings near the distal tip, the sensors (in this case electrodes) detect a different conductivity signal depending on the location of the device within the anatomy.

While the device is in the upper part of the SVC, the conductivity is generally lower than baseline, because of the infusion of the injectate which has a lower conductivity than blood. Since there is less turbulence and less mixing in this area of the vasculature, the magnitude of the signal, or the difference between the signal and baseline, is relatively high in this area. The magnitude of this signal may vary with vessel size and/or anatomy. There is also a fairly large magnitude signal as the device enters the CAJ, as is shown here. As the device crosses the superior vena cava/cavo-atrial junction (SVC-CAJ), and enters the right atrium of the heart, the signal magnitude is reduced. In other words, the signal approaches baseline. This is due to the increased flow rate, turbulence and mixing of the blood in the atrium of the heart, which quickly dilutes and eliminates the lower conductivity injectate, so that the sensors do not sense the presence of the injectate. Since the ideal location for the catheter tip is within the CAJ, the user then withdraws the catheter until the magnitude of the conductivity signal again increases, to a point generally represented by the "X" on the curve. In this way, the magnitude of the conductivity signal may be used to locate the navigation device in the CAJ.

FIGS. 95 and 96 illustrate how the relative magnitude of the signal from the distal and proximal sensors can be used to determine direction of blood flow. FIG. 95 shows the conductivity signal of the vascular navigation device in the external jugular vein of a pig. FIG. 96 shows the conductivity signal of the vascular navigation device in the brachiocephalic vein of a pig. The signals from both the distal sensor and the proximal sensor are shown. Note that blood is flowing with the device, so in the same direction as the advancement of the device, in the brachiocephalic vein, and against the device in the external jugular vein. Blood flowing against the device is an indication that the device is in the wrong vessel and needs to be retracted, so it is important to be able to identify this situation.

In the situation where the device is in the wrong location, where blood is flowing against the device, the signal from the proximal sensor is a larger magnitude from baseline (lower conductivity) than the signal from the distal signal. This is shown in FIG. 95. In the situation where the device is in a blood vessel where blood is flowing with the device, the signal from the proximal sensor is a lower magnitude from baseline (higher conductivity) than the signal from the distal signal. This is shown in FIG. 96. By analyzing the relative magnitude of the distal and proximal sensor, the controller can determine whether the device is in a vessel with blood flowing in the wrong direction (either an incorrect vein or an artery).

FIG. 96 also clearly shows the pulsatile nature of the signal in some locations within the vasculature. Here, in the brachiocephalic vein, the pulsatile nature of both the proximal sensor signal and the distal sensor signal can be seen.

Both the respiratory pulse and the heart pulse can be seen in these signals, each having its own frequency. The heart rate frequency has pulse length 9602 and the respiratory frequency has pulse length 9604. Fourier transforms or other mathematical methods can be used by the controller to extract the various frequencies from the sensor signals to determine heart rate and respiratory rate, in addition to the magnitude and relative magnitude of the sensor signals.

A steady injection of the injectate was used to obtain these data in a pig. Steady, varying or intermittent injection of the injectate may be used.

The pulsatility of the sensor signal depends on the location of the device within the vasculature. For example, smaller vessels may produce a more pulsatile signal than very large vessels, or the heart. Therefore, the pulsatility of the sensor signal may also be used to locate the vascular navigation device. Signal pulsatility, signal magnitude and/or relative signal magnitude may be used to locate the device within the anatomy.

FIG. 97 shows the different types of flow that may be encountered in the vascular system when placing a vascular catheter: inline flow, counter flow, high turbulence bi-directional flow and high turbulence multi-directional flow. FIG. 97 also shows the different types of signals that the vascular navigation device may sense or monitor, including: signal magnitude, signal pulsatility, signal due to electrical activity and other signal types. The controller of the vascular navigation system uses one or more of these signal types to identify where the device is within the anatomy and also communicates to the user instructions based on the sensed location.

Some examples are provided herein, but it is understood that the signal signature may be different than the examples, and may incorporate fewer or more or different signal types. The controller may incorporate the one or more signal types as absolute values, or relative values. The relative values may be relative to another point in time, or relative to another signal type, or relative to the same signal type from a different sensor. For example, the controller of the vascular navigation device may determine that the distal tip of the device is in an artery based on a high proximal sensor signal magnitude. Alternatively or additionally, the determination may be based on an increase in the proximal sensor signal magnitude from a previous time/location of the device. Alternatively or additionally, the determination may be based on the proximal sensor signal magnitude relative to the distal sensor signal magnitude, where the proximal sensor signal magnitude may be higher in an artery. Any of the signal types disclosed herein may be analyzed similarly, either absolutely or relatively or both.

The anatomical diagram shows the location of an entry vein (A), the SVC (B), a vein with contralateral blood flow (C), an artery (D), the CAJ (E), and the right atrium (F). As the device is advanced through the vasculature, ideally, it passes through the entry vein, into the SVC, to the CAJ. The vascular navigating system may detect where the device tip is based on one or more signal signatures. The vascular navigation system may also be able to detect the transition of the location of the device from one anatomical area to another. For example, the vascular navigation system may detect when the device has traveled past the CAJ and has entered the right atrium as it is advanced from the CAJ and instruct the user to retract the catheter/device slightly so that it is again in or near the CAJ. The navigation system may detect when the device has passed back into or near the CAJ and indicates to the user that the device is now in its desired location.

It is also possible that during navigation the catheter/device may enter either an artery or a vein with contralateral blood flow, such as locations (C) or (D). If this occurs, the system may detect, based on one or more signal signatures, that the device is in the wrong location and indicate to the user that he/she should retract the device until the system signals that the device is no longer in the wrong location.

A representation of the vascular navigation device is shown with catheter 9702, proximal sensor 9704, distal sensor 9706 and infusion port area 9708.

The chart in FIG. 97 shows some different types of signals sensed by the sensors and received by the controller of the system at the different locations in the vasculature. These signal types include:

1. Signal Magnitude

The signal magnitude is the magnitude of the sensor signal relative to baseline. The signal magnitude used by the controller may be the absolute signal magnitude, or may be the relative signal magnitude. A relative signal magnitude may be relative to the signal magnitude at another time/location within the vasculature or relative to the magnitude signal of another sensor. For example the controller may use the absolute signal, or the increase or decrease of a signal as the device is advanced through the vasculature. The controller may alternatively or additionally use the relative magnitude of the signal between the distal and proximal sensors—in other words, whether one is a higher magnitude signal than the other and by how much.

2. Signal Pulsatility

The signal pulsatility used by the controller may be the absolute signal pulsatility, or may be the relative signal pulsatility. A relative signal pulsatility may be relative to the signal pulsatility at another time/location within the vasculature or relative to the pulsatility signal of another sensor.

3. Signal Due to Heart Electrical Activity

The signal due to heart electrical activity may be sensed by the sensors. Either one or more than one sensor may pick up the heart electrical activity. The relative signal due to heart electrical activity may be relative in time/location, or the relative signal between two sensors. In general, the signal due to heart electrical activity will be stronger nearer to sinoatrial node at the entryway to the heart.

Other signal types may alternatively or also be used. For example, signal phase (for example, the relative phase of the signal between two sensors) may be used.

The following is an example of how the vascular access device may use signal signatures to locate the device within the anatomy. As the device/catheter is being advanced properly through a vein and the SVC, the blood flow is inline, the proximal sensor signal magnitude may be small or negligible, and the distal sensor signal magnitude may be relatively large (although this may vary depending on the size of the vein). In other words, the ratio between the distal and proximal signal magnitudes shifts to a ratio of generally greater than 1. The pulsatility of the sensor signals may also be relatively large. The signal due to heart electrical activity may be relatively low. The controller may determine from one, or a combination of more than one, of these signal types that the device is in a proper vein and indicate to the user to continue advancing the device.

As the device enters an incorrect vessel, such as an artery or a vein with contralateral blood flow, the proximal sensor signal magnitude may become relatively large, while the distal sensor signal magnitude may become relatively small, in other words, the ratio between the distal and proximal signal magnitudes shifts to a ratio of generally less than 1. The pulsatility of the signals may be large if the device is in an artery, or small if the device is in a contralateral flow vein. The signal due to heart electrical activity may remain relatively low. Based on one or more of these signals, the controller of the vascular navigation system may determine that the device is in an incorrect location, and may be able to determine whether the device is in an artery or vein. The controller indicates to the user that the device should not be advanced further and should be retracted until the sensor signals again indicate that the device is in a vein with inline blood flow.

As the user continues to advance the device through the SVC and into the CAJ, the system will instruct the user to continue advancing until the CAJ or the right atrium is detected. In the CAJ, the magnitude of the distal sensor signal may be relatively high, while the magnitude of the proximal sensor signal may vary. The pulsatility of the signals may be relatively high and the signal due to heart electrical activity may be relatively high. The controller may be able to identify that the device is in the CAJ at this point and instruct the user to stop advancing. Alternatively, the user may be instructed to continue advancing the device as it enters the right atrium of the heart.

The blood flow in the right atrium of the heart is highly turbulent and multi-directional, causing much mixing and quick dilution of the injectate. In this area, the magnitudes of both the distal and proximal sensors signals may be reduced, and the pulsatility of the signals may be reduced. The signal due to heart electrical activity may be relatively low. One or more of these signals may be used by the controller to determine that the device has entered the heart. At this point, the controller will signal the user to stop advancing the device, retract the device until the controller detects that the device is again approximately in, or near the CAJ. The vascular navigation system may automatically control the distance that the device/catheter is retracted to ensure proper location of the distal catheter tip in or near the CAJ. In some embodiments, the vascular navigation device extends a known distance beyond the tip of the catheter, and in this case, the device/catheter may not need to be retracted, as the distal tip of the catheter may be in the CAJ when the distal tip of the vascular navigation device is in the heart.

After the navigation device/catheter have been properly placed, the navigation device may be disengaged from, and removed from the lumen of the catheter.

The controller may determine device location within the vasculature based on signal signatures. One or more than one of the signal types may be used to locate the device. The signal type or combination of signal types used in one location may be different than that used in another location in the anatomy. The controller may also or additionally analyze the signals for particular frequencies representing heart rate, respiratory rate or other factors. This information may also be factored into the controller logic used to locate the device or for other purposes.

Embodiments of the vascular navigation device may use a constant infusion rate of the injectate, an intermittent injection, a varying infusion rate, or various infusion rates, depending on anatomy, patient, location within the anatomy etc. For example, a steady injection rate may be used for navigation, until the device detects turbulent flow. The device may then either signal the user to, or automatically, increase or otherwise change the injectate infusion rate. The resulting sensor data may be used to confirm the location of the device in the heart, vs. the thoracic junction or other bifurcation or elsewhere in the anatomy.

In some embodiments, the infusion rate of the injectate may be constantly varied so that more data at different injection rates may be constantly collected and analyzed. For example, the injection rate may vary in a sine wave, a constant increase or a constant decrease or other function.

In some embodiments, the infusion rate of the injectate may be automatically tuned so that the sensor signals are maximized. This "tuned" infusion rate may be determined by patient, by anatomy, by location in anatomy or any combination of these.

In some embodiments, the infusion rate of the injectate may be varied and tracked so that the signal from the sensors is constant. In this way, the infusion rate may be used to determine vessel parameters including diameter, location of the device, etc.

In some embodiments, the signal signature, and/or the signal magnitude may be used to determine vessel diameter, where a larger signal magnitude generally indicates a vessel of a smaller diameter.

In some embodiments, the health of the vessel may be determined based on sensor signals, infusion rate, or both.

In some embodiments, the controller of the vascular navigation system may use sensor data to collect health data on the patient. For example, the system may be able to assess the hydration level of the patient based on the salinity of the patient's blood. The device can also determine respiratory rate, heart rate, blood flow rate based on the sensor data.

Some embodiments of the vascular navigation system may use data collected to assess the health of the patient, for example the presence or absence or status of heart arrhythmias, valve issues, pulmonary hypertension, deep vein thrombosis, bradycardia or heat block, congenital heart disease of various sorts, ventricular arrhythmias, supraventricular tachycardia, atrial fibrillation, atrial flutter, tachycardia, tre-entrant tachycardia, premature atrial contractions (PACs), premature ventricular contractions, junctional arrhythmias, tricuspid regurgitation, tricuspid stenosis, pulmonary regurgitation, pulmonary stenosis, mitral or aortic stenosis, mitral or aortic regurgitation, atrial septal defect, patient ductus arteriosus, systolic heart failure (or HFrEF), diastolic heart failure (HFpEF), right heart failure, cardiogenic shock, distributive shock, hypovolemic shock, obstructive shock, pulmonary embolism, cardiac effusion, cardiac tamponade, perivalvular leak, subclavian stenosis, jugular vein stenosis, pulmonary vascular shunts, hepatorenal syndrome, hypokalemia, hyperkalemia, digitalis toxicity, superior vena cava syndrome, inferior vena cava syndrome, pneumothorax, lung or mediastinal masses, pleural disease or effusion, diaphragmatic paralysis, compartment syndrome, cirrhosis, angioplasty, aortic aneurysm, arterial bypass, cardiac catheterization, cardiac devic monitoring, cardiomyopathy, carotid artery stenting, carotid endarterectomy, computed tomography, congestive heart failure (CHF), constrictive pericarditis, coronary artery bypass surgery, dilated cardiomyopathy, echocardiography, heart transplant, hypertrophic cardiomyopathy, implantable cardioverter-defibrillator (ICD), varicose vein treatment, mitral prolapse, pericardial effusion, restrictive cardiomyopathy, stroke, thrombectomy, ventricular assist devices (VAD) etc. machine learning and or neural networks may be used within one patient or using data from more than one patient to correlate signature signals received and analyzed by the controller with particular disease states or risks.

Some embodiments of the vascular navigation system may help identify positioning or malpositioning of devices such as pacemakers, ECMO (Extracorporeal membrane oxygenation) circuits, intraaortic balloon pumps, impellor based heart pumps, IVC filter placement, umbilical vessel catheters, etc.

Some embodiments of the vascular navigation system are designed to automatically calibrate the system. For example, when first inserted, the device may be able to assess the relative salinity of the patient's blood, the relative vasculature size, blood flow rate, blood viscosity of the patient, etc. The system may automatically run through a range of injectate infusion rates to maximize the sensor signal in a given patient. The system may collect sensor data with zero injectate infusion, and at set or varying rates of injectate infusion. The calibration process may be performed at the beginning of the procedure, or at any time during the procedure. The calibration process may also be performed manually, with or without prompts from the controller.

Some embodiments of the vascular navigation system use device vibration data to help determine device location. Some embodiments control for device vibration.

Some embodiments disclosed herein may be used to determine fluid levels, or hydration level, of a patient. Fluid levels are particularly important when a patient has congestive heart challenges. A lower fluid level may result in lower amplitude pulses in the blood flow, where a higher fluid level may result in greater amplitude blood flow pulses. Other flow patterns may be different between a hydrated patient and a less hydrated patient. These flow patterns can be detected using embodiments disclosed herein. Hydration level can be monitored in a patient over time or compared among patients.

Some embodiments of the vascular navigation system use controller logic to identify signal signatures specific to certain conditions, including the condition where the sensor area of the device is up against a wall of a vessel or in a curve of a vessel. In this condition, it is possible that the sensors are not adequately or circumferentially being exposed to the injectate fluid. It is also possible that the sensors may sense the tissue of the wall of the vessel itself instead of the fluid within the vessel. The controller may identify these situations based on changes of any of the sensor signals disclosed herein and may perform one or more of several functions to change the condition, such as: indicating to the user to move the device forward, backward or rotationally, moving the device automatically, moving the device with respect to the catheter, increasing or decreasing the injectate infusion flow rate, changing the injectate infusion flow rate from pulsatile to continuous or from continuous to pulsatile, changing the sampling and/or driving frequency, etc.

Some embodiments of the vascular navigation system include sensors to sense other patient parameters, such as chemical sensors ($O_2$, glucose, electrolytes, etc.), temperature sensors, viscosity sensors, blood thickness sensors, pressure sensors, ECG, etc. For example, blood clotting time may be able to be determined after the introduction of blood thinning drugs. These sensors may sense these parameters in real time.

Some embodiments of the vascular navigation system may include algorithms that use different types of signals and/or determinations. For example, by measuring vessel diameter and blood flow rates, as well as determining device position, some embodiments may perform real time estimates of how well drugs are mixing in, or infusing into, the blood stream. In some embodiments, the drug(s), may be the injectate fluid. Midline catheter placement, which may be more affordable and easier to place than PICCS and Central catheter lines, but are different than PICC lines in that they are not placed at the CAJ. By determining the mixing rate, or mixing result of two infusion mediums, the vascular navigation system may determine the device location based on this mixing outside of the CAJ.

The infusion fluid in embodiments which use conductance/resistance sensors/electrodes may be of a higher or lower salinity (i.e. higher or lower conductivity) than blood. For example, the infusion fluid may be distilled water, Dextrose 5% in Water (D5 W), etc.

The controller may also integrate with other systems, such as electronic medical systems, electronic health systems etc. The integration may be wired or wireless and may be local or remote. The integration may be via "EMR sniffers".

From the foregoing, it will be appreciated that specific embodiments of the invention have been described herein for purposes of illustration, but that various modifications may be made without deviating from the spirit and scope of the various embodiments of the invention. For example, several embodiments may include various suitable combinations of components, devices and/or systems from any of the embodiments described herein. Further, while various advantages associated with certain embodiments of the invention have been described above in the context of those embodiments, other embodiments may also exhibit such advantages, and not all embodiments need necessarily exhibit such advantages to fall within the scope of the invention.

What is claimed is:

1. A location detection system, comprising:
an elongate body defining a lumen at least partially along a length of the elongate body;
one or more sensors positioned near or at a distal tip of the elongate body;
one or more openings defined along the elongate body in proximity to the one or more sensors;
a fluid with a parameter of a known initial value when emitted from the one or more openings; and
a controller in communication with the one or more sensors, wherein the controller is configured to track a change in the parameter relating to concentration of the fluid after being emitted from the one or more openings and passing over the one or more sensors and wherein the controller is further configured to determine a position of the one or more sensors within a body of a subject based upon the dilution of the fluid after being emitted.

2. The system of claim 1 wherein the one or more openings comprise a diffuse exit port.

3. The system of claim 1 wherein the one or more openings comprise a plurality of openings which are adjacent to one another.

4. The system of claim 1 further comprising a stiffening member extending at least partially through the lumen.

5. The system of claim 4 wherein a ratio of an internal diameter of the elongate body relative to an outer diameter of the stiffening member ranges from 0.1 to 0.7.

6. The system of claim 4 wherein the one or more openings are defined such that a ratio of the exit port openings total area relative to a cross-sectional area between the internal diameter of the elongate body and an outer diameter of the stiffening member ranges from 1.2 to 30.

7. The system of claim 4 wherein the one or more openings are defined such that a ratio of the exit port openings total area relative to a cross-sectional area of the internal diameter of the elongate body ranges from 1.2 to 30.

8. The system of claim 1 further comprising a sleeve positioned in proximity to the one or more sensors such that the one or more openings define annular or circumferential openings.

9. The system of claim 1 wherein the one or more openings are defined along a portion having a reduced diameter relative to the one or more sensors.

10. The system of claim 9 further comprising a sleeve positioned in proximity to the one or more sensors such that the one or more openings define annular or circumferential openings along the reduced diameter.

11. The system of claim 1 wherein the known initial value of the fluid comprises conductivity.

12. The system of claim 11 wherein the conductivity of the fluid is selected to be lower than a conductivity of a second fluid surrounding the one or more sensors.

13. The system of claim 1 wherein the one or more sensors comprise at least two sensors.

14. The system of claim 1 wherein the one or more openings are positioned between at least two sensors along the elongate body.

15. The system of claim 1 wherein the one or more openings are sized and positioned to minimize the boundary distance when the fluid is emitted at a predetermined flow rate.

16. A location detection system, comprising:
    an elongate body defining a lumen at least partially along a length of the elongate body;
    one or more sensors positioned near or at a distal tip of the elongate body;
    one or more openings defined along the elongate body in proximity to the one or more sensors;
    a fluid with a parameter of a known initial value when the fluid is emitted at a predetermined flow rate; and
    a controller in communication with the one or more sensors, wherein the controller is configured to track a change in the parameter relating to concentration of the fluid after being emitted from the one or more openings and passing over the one or more sensors and determine a position of the one or more sensors within a body of a subject based upon the dilution of the fluid after being emitted.

17. The system of claim 16 wherein the one or more openings comprise a diffuse exit port.

18. The system of claim 16 wherein the one or more openings comprise a plurality of openings which are adjacent to one another.

19. The system of claim 16 further comprising a stiffening member extending at least partially through the lumen.

20. The system of claim 19 wherein a ratio of an internal diameter of the elongate body relative to an outer diameter of the stiffening member ranges from 0.1 to 0.7.

21. The system of claim 19 wherein the one or more openings are defined such that a ratio of the exit port openings total area relative to a cross-sectional area between the internal diameter of the elongate body and an outer diameter of the stiffening member ranges from 1.2 to 30.

22. The system of claim 19 wherein the one or more openings are defined such that a ratio of the exit port openings total area relative to a cross-sectional area of the internal diameter of the elongate body ranges from 1.2 to 30.

23. The system of claim 16 further comprising a sleeve positioned in proximity to the one or more sensors such that the one or more openings define annular or circumferential openings.

24. The system of claim 16 wherein the one or more openings are defined along a portion having a reduced diameter relative to the one or more sensors.

25. The system of claim 24 further comprising a sleeve positioned in proximity to the one or more sensors such that the one or more openings define annular or circumferential openings along the reduced diameter.

26. The system of claim 16 wherein the known initial value of the fluid comprises conductivity.

27. The system of claim 26 wherein the conductivity of the fluid is selected to be lower than a conductivity of a second fluid surrounding the one or more sensors.

28. The system of claim 16 wherein the one or more sensors comprise at least two sensors.

29. The system of claim 16 wherein the one or more openings are positioned between at least two sensors along the elongate body.

30. The system of claim 16 wherein the one or more openings are sized and positioned to minimize the boundary distance when the fluid is emitted at a predetermined flow rate.

31. A method of determining a location within a body of a subject, comprising:
    emitting a fluid with a parameter of a known initial value through one or more openings defined along an elongate body;
    sensing a change in the parameter of the fluid relating to concentration of the fluid after being emitted from the one or more openings and passing over one or more sensors positioned near or at a distal tip of the elongate body and in proximity to the one or more openings; and
    determining a position of the one or more sensors within the body of the subject based upon a dilution of the fluid after being emitted.

32. The method of claim 31 further comprising advancing the elongate body intravascularly within the body of the subject.

33. The method of claim 31 wherein emitting a fluid comprises emitting the fluid such that the fluid diffuses when emitted through the one or more openings.

34. The method of claim 31 wherein emitting a fluid comprises emitting the fluid through the one or more openings which define an annular or circumferential opening.

35. The method of claim 31 wherein emitting a fluid comprises emitting the fluid through the one or more openings which are positioned along a portion having a reduced diameter relative to the one or more sensors.

36. The method of claim 31 wherein sensing a change in the parameter comprises sensing a change in conductivity.

37. The method of claim 31 wherein sensing the change in the parameter of the fluid comprises sensing via at least two sensors.

38. The method of claim 31 wherein emitting a fluid comprises emitting the fluid at a predetermined flow rate through the one or more openings which are sized and positioned to minimize the boundary distance.

* * * * *